US008709418B2

(12) United States Patent
Okano et al.

(10) Patent No.: US 8,709,418 B2
(45) Date of Patent: Apr. 29, 2014

(54) PHARMACEUTICAL COMPOSITION FOR TREATING CAPRIN-1 EXPRESSING CANCER

(75) Inventors: Fumiyoshi Okano, Kanagawa (JP); Takanori Saito, Kanagawa (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 13/576,955

(22) PCT Filed: Feb. 4, 2011

(86) PCT No.: PCT/JP2011/052384
§ 371 (c)(1), (2), (4) Date: Aug. 3, 2012

(87) PCT Pub. No.: WO2011/096519
PCT Pub. Date: Aug. 11, 2011

(65) Prior Publication Data

US 2012/0321641 A1 Dec. 20, 2012

(30) Foreign Application Priority Data

Feb. 4, 2010 (JP) ................................ 2010-023452

(51) Int. Cl.
*A61K 39/395* (2006.01)
*C07K 16/30* (2006.01)
*A61K 35/02* (2006.01)

(52) U.S. Cl.
USPC .................. 424/130.1; 424/133.1; 424/135.1; 424/136.1; 424/138.1; 424/142.1; 530/389.7; 514/19.3; 514/19.4; 514/19.6

(58) Field of Classification Search
None
See application file for complete search history.

(56) References Cited

U.S. PATENT DOCUMENTS

| | | | |
|---|---|---|---|
| 5,698,396 | A | 12/1997 | Pfreundschuh |
| 6,335,170 | B1 | 1/2002 | Orntoft |
| 6,444,425 | B1 | 9/2002 | Reed et al. |
| 7,449,184 | B2 | 11/2008 | Allison et al. |
| 7,485,302 | B2 | 2/2009 | Adams et al. |
| 7,745,391 | B2 | 6/2010 | Mintz et al. |
| 8,008,431 | B2 | 8/2011 | Weinschenk et al. |
| 8,211,634 | B2 | 7/2012 | DePinho et al. |
| 2003/0118599 | A1 | 6/2003 | Algate et al. |
| 2003/0190640 | A1 | 10/2003 | Faris et al. |
| 2004/0029114 | A1 | 2/2004 | Mack et al. |
| 2004/0236091 | A1 | 11/2004 | Chicz et al. |
| 2005/0003390 | A1 | 1/2005 | Axenovich et al. |
| 2005/0032113 | A1 | 2/2005 | Tanaka et al. |
| 2006/0019256 | A1 | 1/2006 | Clarke et al. |
| 2006/0069054 | A1 | 3/2006 | Houghton et al. |
| 2006/0275305 | A1 | 12/2006 | Bryant |
| 2007/0048301 | A1 | 3/2007 | Bodary-Winter et al. |
| 2007/0154931 | A1 | 7/2007 | Radich et al. |
| 2008/0075722 | A1 | 3/2008 | DePinho et al. |
| 2008/0107668 | A1 | 5/2008 | Philip et al. |
| 2010/0029573 | A1 | 2/2010 | Weinschenk et al. |
| 2010/0068724 | A1 | 3/2010 | Fung et al. |
| 2011/0123492 | A1 | 5/2011 | Okano et al. |
| 2011/0136121 | A1 | 6/2011 | Okano et al. |
| 2011/0189700 | A1 | 8/2011 | Moses et al. |
| 2011/0256144 | A1 | 10/2011 | Okano et al. |
| 2012/0294860 | A1 | 11/2012 | Ido et al. |
| 2012/0301471 | A1 | 11/2012 | Kobayashi et al. |
| 2012/0301476 | A1 | 11/2012 | Okano et al. |
| 2013/0045210 | A1 | 2/2013 | Kobayashi et al. |
| 2013/0071398 | A1 | 3/2013 | Saito et al. |

FOREIGN PATENT DOCUMENTS

| | | | |
|---|---|---|---|
| CN | 1678338 | A | 10/2005 |
| CN | 1705676 | A | 12/2005 |
| CN | 101120252 | A | 2/2008 |
| CN | 101189516 | A | 5/2008 |
| EP | 1557172 | A1 | 7/2005 |
| JP | 2002-540790 | A | 12/2002 |
| JP | 2003-528587 | A | 9/2003 |
| JP | 2006-316040 | A | 11/2006 |
| WO | WO 00/60077 | A2 | 10/2000 |
| WO | WO 01/32910 | A2 | 5/2001 |
| WO | WO 01/72295 | A2 | 10/2001 |
| WO | WO 02/078524 | A2 | 10/2002 |
| WO | WO 02/083070 | A2 | 10/2002 |
| WO | WO 02/092001 | A2 | 11/2002 |
| WO | WO 2004/076682 | A2 | 9/2004 |
| WO | WO 2004/097051 | A2 | 11/2004 |
| WO | WO 2005/007830 | A2 | 1/2005 |
| WO | WO 2005/100998 | A2 | 10/2005 |
| WO | WO 2005/116051 | A2 | 12/2005 |
| WO | WO 2006/002378 | A2 | 1/2006 |

(Continued)

OTHER PUBLICATIONS

International Search Report issued in PCT/JP2011/052384 dated Mar. 15, 2011.
Kolobova, et al. "Microtubule-dependent association of AKAP350A and CCAR 1 with RNA stress granules", Experimental Cell Research, 2009, vol. 315, pp. 542-555.
Chinese Office Action issued in Chinese Patent Application No. 200980139037.X on Mar. 29, 2013.

(Continued)

*Primary Examiner* — Elly-Gerald Stoica
(74) *Attorney, Agent, or Firm* — Birch, Stewart, Kolasch & Birch, LLP

(57) ABSTRACT

According to the present invention, a cancer antigen protein to be specifically expressed on the surfaces of cancer cells is identified and thus the use of an antibody targeting the cancer antigen protein as an agent for treating and/or preventing a cancer is provided. Specifically, the present invention provides a pharmaceutical composition for treating and/or preventing a cancer, which comprises an antibody comprising a heavy chain variable region that comprises SEQ ID NOS: 39, 40, and 41 and a light chain variable region that comprises SEQ ID NOS: 43, 44, and 45 or a fragment thereof as an active ingredient and having immunological reactivity with a CAPRIN-1 protein.

14 Claims, 3 Drawing Sheets

(56) References Cited

FOREIGN PATENT DOCUMENTS

| | | | |
|---|---|---|---|
| WO | WO 2007/150077 | A2 | 12/2007 |
| WO | WO 2008/031041 | A2 | 3/2008 |
| WO | WO 2008/059252 | A2 | 5/2008 |
| WO | WO 2008/073162 | A2 | 6/2008 |
| WO | WO 2008/088583 | A2 | 7/2008 |
| WO | WO 2010/016525 | A1 | 2/2010 |
| WO | WO 2010/016526 | A1 | 2/2010 |
| WO | WO 2010/016527 | A1 | 2/2010 |
| WO | WO 2011/096517 | A1 | 8/2011 |
| WO | WO 2011/096528 | A1 | 8/2011 |
| WO | WO 2011/096533 | A1 | 8/2011 |
| WO | WO 2011/096534 | A1 | 8/2011 |
| WO | WO 2011/096535 | A1 | 8/2011 |
| WO | WO 2013/018885 | A1 | 2/2013 |
| WO | WO 2013/018886 | A1 | 2/2013 |
| WO | WO 2013/018894 | A1 | 2/2013 |

OTHER PUBLICATIONS

Lu et al., "Targeting serum antibody for cancer diagnosis: a focus on colorectal cancer," Oncologic, Endocrine & Metabolic, Expert Opinion on Therapeutic Targets, vol. 11, No. 2, Feb. 2007, pp. 235-244.

NCBI Reference Sequence, caprin-1 [*Bos taurus*], Feb. 23, 2013. Accession No. NP001069530, XP615677, 1 page.

NCBI Reference Sequence, caprin-1 [*Gallus gallus*], Feb. 22, 2013, Accession No. NP001026536, XP423820, 1 page.

NCBI Reference Sequence, caprin-1 isoform 1 [*Homo sapiens*], Mar. 17, 2013, Accession No. NP005889, 3 pages.

NCBI Reference Sequence, caprin-1 isoform 2 [*Homo sapiens*], Mar. 3, 2013, Accession No. NP976240, 3 pages.

NCBI Reference Sequence, caprin-1 isoform a [*Mus musculus*], Mar. 23, 2013, Accession No. NP058019, 3 pages.

NCBI Reference Sequence, caprin-1 isoform b [*Mus musculus*], Mar. 23, 2013, Accession No. NP001104760, 3 pages.

NCBI Reference Sequence, caprin-1 isoform c [*Mus musculus*], Mar. 23, 2013, Accession No. NP001104761,4 pages.

NCBI Reference Sequence, Predicted: caprin-1 [*Equus caballus*], Jun. 27, 2011, Accession No. XP001492799, 1 page.

NCBI Reference Sequence, Predicted: caprin-1 isoform 2 [*Canis lupus familiaris*], Dec. 2, 2011, Accession No. XP858109, 1 page.

Scanlan et al., "Cancer-related Serological Recognition of Human Colon Cancer: Identification of Potential Diagnostic and Immunotherapeutic Targets," Cancer Research, vol. 62, Jul. 15, 2002, pp. 4041-4047.

Akiyoshi, "Cancer Vaccine Therapy Using Peptides Derived from Tumor-rejection Antigens," Jpn. J. Cancer Chemother., vol. 24, No. 5, Mar. 1997, pp. 511-519, with English Abstract (p. 519).

Bodey et al., "Failure of Cancer Vaccines: The Significant Limitations of this Approach to Immunotherapy," Anticancer Research, vol. 20, 2000, pp. 2665-2676.

Brass et al., "Translation initiation factor eIF-4gamma is encoded by an amplified gene and induces an immune response in squamous cell lung carcinoma," Human Molecular Genetics, vol. 6, No. 1, 1997, pp. 33-39.

Chamberlain et al., "Innovations and strategies for the development of anticancer vaccines," Expert Opinion on Pharmacotherapy, vol. 1, No. 4, 2000, pp. 603-614.

Ellis et al., "Identification and Characterization of a Novel Protein (p137) Which Transcytoses Bidirectionally in Caco-2 Cells," The Journal of Biological Chemistry, vol. 270, No. 35, Sep. 1, 1995, pp. 20717-20723.

Grill et al., "Activation/Division of Lymphocytes Results in Increased Levels of Cytoplasmic Activation/Proliferation-Associated Protein-1: Prototype of a New Family of Proteins," The Journal of Immunology, vol. 172, 2004, pp. 2389-2400.

Güre et al., "Human Lung Cancer Antigens Recognized by Autologous Antibodies: Definition of a Novel cDNA Derived from the Tumor Suppressor Gene Locus on Chromosome 3p21.3," Cancer Research, vol. 58, Mar. 1, 1998, pp. 1034-1041.

Gure et al., "SSX: A Multigene Family with Several Members Transcribed in Normal Testis and Human Cancer," Int. J. Cancer, vol. 72, 1997, pp. 965-971.

Hugo Gene Nomenclature Committee, Gene Symbol Report, CAPRIN1, Approved Name: Cell Cycle Associated Protein 1, HGNC ID: HGNC:6743, Nov. 3, 2012, 2 pages.

Itoh et al., "HUB1 is an autoantigen frequently eliciting humoral immune response in patients with adult T cell leukemia," Int. J. Oncol., vol. 14, 1999, pp. 703-708 (Abstract only provided).

Jang et al., "Antihypertensive Angiotensin I-Converting Enzyme Inhibitory Activity and Antioxidant Activity of Vitis hybrid-Vitis coignetiae Red Wine Made with *Saccharomyces cerevisiae*," Mycobiology, vol. 39, No. 2, 2011, pp. 137-139.

Kaddar et al., "Two new miR-16 targets: caprin-1 and HMGA1, proteins implicated in cell proliferation," Biology of the Cell, vol. 101, No. 9, 2009, pp. 511-524.

Kajiji et al., "Six Monoclonal Antibodies to Human Pancreatic Cancer Antigens," Cancer Research, vol. 47, Mar. 1, 1987, pp. 1367-1376.

Katsafanas et al., "Colocalization of Transcription and Translation within Cytoplasmic Poxvirus Factories Coordinates Viral Expression and Subjugates Host Functions," Cell Host & Microbe, vol. 2, Oct. 2007, pp. 221-228.

Katsafanas et al., "Vaccinia Virus Intermediate Stage Transcription is Complemented by Ras-GTPase-activating Protein SH3 Domain-binding Protein (G3BP) . . . ," Jour. of Biol. Chem., vol. 279, No. 50, Dec. 10, 2004, pp. 52210-52217.

Lu et al., "Identification of an immunological signature of tumor rejection in the neu transgenic mouse," 2007 AARC Annual Meeting, Proceedings Abstract No. 4131, Apr. 14-18, 2007 (Presentation conducted on Apr. 17, 2007) (Abstract only provided).

Müller-Pillasch et al., "Identification of a new tumour-associated antigen TM4SF5 and its expression in human cancer," Gene, vol. 208, 1998, pp. 25-30.

Rauch et al., "SEREX, Proteomex, AMIDA, and beyond; Serological screening technologies for target identification," Proteomics Clin. Appl., vol. 2, 2008, pp. 355-371.

Sahin et al., "Human neoplasms elicit multiple specific immune responses in the autologous host," Proc. Natl. Acad. Sci. USA, vol. 92, Dec. 1995, pp. 11810-11813.

Scanlan et al., "Characterization of Human Colon Cancer Antigens Recognized by Autologous Antibodies," Int. J. Cancer, vol. 76, 1998, pp. 652-658.

Solomon et al., "Distinct Structural Features of Caprin-1 Mediate its Interaction with G3BP-1 and Its Induction of Phosphorylation of Eukaryotic Translation Initiation Factor 2$\alpha$, Entry to Cytoplasmic Stress Granules . . . ," Molecular and Cellular Biology, vol. 27, No. 6, Mar. 2007, pp. 2324-2342.

Türeci et al., "The SSX-2 Gene, Which Is Involved in the t(X; 18) Translocation of Synovial Sarcomas, Codes for the Human Tumor Antigen HOM-MEL-40," Cancer Research, vol. 56, Oct. 15, 1996, pp. 4766-4772.

Van Der Bruggen et al., "A Gene Encoding an Antigen Recognized by Cytolytic T Lymphocytes on a Human Melanoma," Science, vol. 254, No. 5038, Dec. 13, 1991, pp. 1649-1647 (Also published in J. Immunol., vol. 178, 2007, pp. 2617-2621).

Wang et al., "Absence of Caprin-1 Results in Defects in Cellular Proliferation," The Journal of Immunology, vol. 175, 2005, pp. 4274-4282.

Yanai et al., "Dlk-1, a cell surface antigen on foetal hepatic stem/progenitor cells, is expressed in hepatocellular, colon, pancreas and breast carcinomas at a high frequency," The Journal of Biochemistry, vol. 148, No. 1, 2010 (Publ. online Mar. 30, 2010), pp. 85-92.

GeneCards, "Cell Cycle Associated Protein 1—Biological research products for CAPRIN 1", updated Mar. 19, 2013, 10 pages.

Karauzum et al., "Caprin 1 is Frequently Overexpressed in Human Lymphomas," American Society of Human Genetics, Cancer Genetics, Program No. 1190W, Oct. 12, 2011, Abstract only.

United States Office Action, dated Jul. 1, 2013, for U.S. Appl. No. 13/577,212.

United States Office Action, dated Jul. 16, 2013, for U.S. Appl. No. 13/057,709.

Dog normal tissues
Muscle
Lung
Thymus
Spleen
Pancreas
Kidney
Liver
Eye
Heart
Testis
Peripheral blood
1
2
Dog breast cancer tissues
A
B
C
D
E
F
1
2
Human breast cancer cell lines
A
B
C
D
E
F
G
H
1
2
Human cancer cell lines
Brain tumor
A
B
C
D
Leukemia
A
B
C
Lung cancer
Esophageal cancer
A
B
1
2

Size of tumor ($mm^3$)
600
0
Days after administration of antibody (days)
1
3
5
7
9
11
13
15
5
6

SEQUENCE LISTING

```
<160> NUMBER OF SEQ ID NOS: 53

<210> SEQ ID NO 1
<211> LENGTH: 5562
<212> TYPE: DNA
<213> ORGANISM: Homo sapiens
<220> FEATURE:
<221> NAME/KEY: CDS
<222> LOCATION: (190)..(2319)
<223> OTHER INFORMATION:

<400> SEQUENCE: 1

cagagggctg ctggctggct aagtccctcc cgctcccggc tctcgcctca ctaggagcgg      60

ctctcggtgc agcgggacag ggcgaagcgg cctgcgccca cggagcgcgc gacactgccc     120

ggaagggacc gccacccttg ccccctcagc tgcccactcg tgatttccag cggcctccgc     180

gcgcgcacg atg ccc tcg gcc acc agc cac agc ggg agc ggc agc aag tcg     231
          Met Pro Ser Ala Thr Ser His Ser Gly Ser Gly Ser Lys Ser
          1               5                   10

tcc gga ccg cca ccg ccg tcg ggt tcc tcc ggg agt gag gcg gcc gcg      279
Ser Gly Pro Pro Pro Pro Ser Gly Ser Ser Gly Ser Glu Ala Ala Ala
15                  20                  25                  30

gga gcc ggg gcc gcc gcg ccg gct tct cag cac ccc gca acc ggc acc      327
Gly Ala Gly Ala Ala Ala Pro Ala Ser Gln His Pro Ala Thr Gly Thr
```

```
                35                  40                  45

ggc gct gtc cag acc gag gcc atg aag cag att ctc ggg gtg atc gac      375
Gly Ala Val Gln Thr Glu Ala Met Lys Gln Ile Leu Gly Val Ile Asp
            50                  55                  60

aag aaa ctt cgg aac ctg gag aag aaa aag ggt aag ctt gat gat tac      423
Lys Lys Leu Arg Asn Leu Glu Lys Lys Lys Gly Lys Leu Asp Asp Tyr
        65                  70                  75

cag gaa cga atg aac aaa ggg gaa agg ctt aat caa gat cag ctg gat      471
Gln Glu Arg Met Asn Lys Gly Glu Arg Leu Asn Gln Asp Gln Leu Asp
    80                  85                  90

gcc gtt tct aag tac cag gaa gtc aca aat aat ttg gag ttt gca aaa      519
Ala Val Ser Lys Tyr Gln Glu Val Thr Asn Asn Leu Glu Phe Ala Lys
95                  100                 105                 110

gaa tta cag agg agt ttc atg gca cta agt caa gat att cag aaa aca      567
Glu Leu Gln Arg Ser Phe Met Ala Leu Ser Gln Asp Ile Gln Lys Thr
                115                 120                 125

ata aag aag aca gca cgt cgg gag cag ctt atg aga gaa gaa gct gaa      615
Ile Lys Lys Thr Ala Arg Arg Glu Gln Leu Met Arg Glu Glu Ala Glu
            130                 135                 140

cag aaa cgt tta aaa act gta ctt gag cta cag tat gtt ttg gac aaa      663
Gln Lys Arg Leu Lys Thr Val Leu Glu Leu Gln Tyr Val Leu Asp Lys
        145                 150                 155

ttg gga gat gat gaa gtg cgg act gac ctg aaa caa ggt ttg aat gga      711
Leu Gly Asp Asp Glu Val Arg Thr Asp Leu Lys Gln Gly Leu Asn Gly
    160                 165                 170

gtg cca ata ttg tcc gaa gag gag ttg tca ttg ttg gat gaa ttc tat      759
Val Pro Ile Leu Ser Glu Glu Glu Leu Ser Leu Leu Asp Glu Phe Tyr
175                 180                 185                 190

aag cta gta gac cct gaa cgg gac atg agc ttg agg ttg aat gaa cag      807
Lys Leu Val Asp Pro Glu Arg Asp Met Ser Leu Arg Leu Asn Glu Gln
                195                 200                 205

tat gaa cat gcc tcc att cac ctg tgg gac ctg ctg gaa ggg aag gaa      855
Tyr Glu His Ala Ser Ile His Leu Trp Asp Leu Leu Glu Gly Lys Glu
            210                 215                 220

aaa cct gta tgt gga acc acc tat aaa gtt cta aag gaa att gtt gag      903
Lys Pro Val Cys Gly Thr Thr Tyr Lys Val Leu Lys Glu Ile Val Glu
        225                 230                 235

cgt gtt ttt cag tca aac tac ttt gac agc acc cac aac cac cag aat      951
Arg Val Phe Gln Ser Asn Tyr Phe Asp Ser Thr His Asn His Gln Asn
    240                 245                 250

ggg ctg tgt gag gaa gaa gag gca gcc tca gca cct gca gtt gaa gac      999
Gly Leu Cys Glu Glu Glu Glu Ala Ala Ser Ala Pro Ala Val Glu Asp
255                 260                 265                 270

cag gta cct gaa gct gaa cct gag cca gca gaa gag tac act gag caa     1047
Gln Val Pro Glu Ala Glu Pro Glu Pro Ala Glu Glu Tyr Thr Glu Gln
                275                 280                 285

agt gaa gtt gaa tca aca gag tat gta aat aga cag ttc atg gca gaa     1095
Ser Glu Val Glu Ser Thr Glu Tyr Val Asn Arg Gln Phe Met Ala Glu
            290                 295                 300

aca cag ttc acc agt ggt gaa aag gag cag gta gat gag tgg aca gtt     1143
Thr Gln Phe Thr Ser Gly Glu Lys Glu Gln Val Asp Glu Trp Thr Val
        305                 310                 315

gaa acg gtt gag gtg gta aat tca ctc cag cag caa cct cag gct gca     1191
Glu Thr Val Glu Val Val Asn Ser Leu Gln Gln Gln Pro Gln Ala Ala
    320                 325                 330

tcc cct tca gta cca gag ccc cac tct ttg act cca gtg gct cag gca     1239
Ser Pro Ser Val Pro Glu Pro His Ser Leu Thr Pro Val Ala Gln Ala
335                 340                 345                 350

gat ccc ctt gtg aga aga cag cga gta caa gac ctt atg gca caa atg     1287
Asp Pro Leu Val Arg Arg Gln Arg Val Gln Asp Leu Met Ala Gln Met
```

```
                355                 360                 365

cag ggt ccc tat aat ttc ata cag gat tca atg ctg gat ttt gaa aat      1335
Gln Gly Pro Tyr Asn Phe Ile Gln Asp Ser Met Leu Asp Phe Glu Asn
            370                 375                 380

cag aca ctt gat cct gcc att gta tct gca cag cct atg aat cca aca      1383
Gln Thr Leu Asp Pro Ala Ile Val Ser Ala Gln Pro Met Asn Pro Thr
        385                 390                 395

caa aac atg gac atg ccc cag ctg gtt tgc cct cca gtt cat tct gaa      1431
Gln Asn Met Asp Met Pro Gln Leu Val Cys Pro Pro Val His Ser Glu
    400                 405                 410

tct aga ctt gct cag cct aat caa gtt cct gta caa cca gaa gcg aca      1479
Ser Arg Leu Ala Gln Pro Asn Gln Val Pro Val Gln Pro Glu Ala Thr
415                 420                 425                 430

cag gtt cct ttg gta tca tcc aca agt gag ggg tac aca gca tct caa      1527
Gln Val Pro Leu Val Ser Ser Thr Ser Glu Gly Tyr Thr Ala Ser Gln
                435                 440                 445

ccc ttg tac cag cct tct cat gct aca gag caa cga cca cag aag gaa      1575
Pro Leu Tyr Gln Pro Ser His Ala Thr Glu Gln Arg Pro Gln Lys Glu
            450                 455                 460

cca att gat cag att cag gca aca atc tct tta aat aca gac cag act      1623
Pro Ile Asp Gln Ile Gln Ala Thr Ile Ser Leu Asn Thr Asp Gln Thr
        465                 470                 475

aca gca tca tca tcc ctt cct gct gcg tct cag cct caa gta ttt cag      1671
Thr Ala Ser Ser Ser Leu Pro Ala Ala Ser Gln Pro Gln Val Phe Gln
    480                 485                 490

gct ggg aca agc aaa cct tta cat agc agt gga atc aat gta aat gca      1719
Ala Gly Thr Ser Lys Pro Leu His Ser Ser Gly Ile Asn Val Asn Ala
495                 500                 505                 510

gct cca ttc caa tcc atg caa acg gtg ttc aat atg aat gcc cca gtt      1767
Ala Pro Phe Gln Ser Met Gln Thr Val Phe Asn Met Asn Ala Pro Val
                515                 520                 525

cct cct gtt aat gaa cca gaa act tta aaa cag caa aat cag tac cag      1815
Pro Pro Val Asn Glu Pro Glu Thr Leu Lys Gln Gln Asn Gln Tyr Gln
            530                 535                 540

gcc agt tat aac cag agc ttt tct agt cag cct cac caa gta gaa caa      1863
Ala Ser Tyr Asn Gln Ser Phe Ser Ser Gln Pro His Gln Val Glu Gln
        545                 550                 555

aca gag ctt cag caa gaa cag ctt caa aca gtg gtt ggc act tac cat      1911
Thr Glu Leu Gln Gln Glu Gln Leu Gln Thr Val Val Gly Thr Tyr His
    560                 565                 570

ggt tcc cca gac cag tcc cat caa gtg act ggt aac cac cag cag cct      1959
Gly Ser Pro Asp Gln Ser His Gln Val Thr Gly Asn His Gln Gln Pro
575                 580                 585                 590

cct cag cag aac act gga ttt cca cgt agc aat cag ccc tat tac aat      2007
Pro Gln Gln Asn Thr Gly Phe Pro Arg Ser Asn Gln Pro Tyr Tyr Asn
                595                 600                 605

agt cgt ggt gtg tct cgt gga ggc tcc cgt ggt gct aga ggc ttg atg      2055
Ser Arg Gly Val Ser Arg Gly Gly Ser Arg Gly Ala Arg Gly Leu Met
            610                 615                 620

aat gga tac cgg ggc cct gcc aat gga ttc aga gga gga tat gat ggt      2103
Asn Gly Tyr Arg Gly Pro Ala Asn Gly Phe Arg Gly Gly Tyr Asp Gly
        625                 630                 635

tac cgc cct tca ttc tct aac act cca aac agt ggt tat aca cag tct      2151
Tyr Arg Pro Ser Phe Ser Asn Thr Pro Asn Ser Gly Tyr Thr Gln Ser
    640                 645                 650

cag ttc agt gct ccc cgg gat tac tct ggc tat caa cgg gat gga tat      2199
Gln Phe Ser Ala Pro Arg Asp Tyr Ser Gly Tyr Gln Arg Asp Gly Tyr
655                 660                 665                 670

cag cag aat ttc aag cga ggc tct ggg cag agt gga cca cgg gga gcc      2247
Gln Gln Asn Phe Lys Arg Gly Ser Gly Gln Ser Gly Pro Arg Gly Ala
```

-continued

```
                675                 680                 685

cca cga ggt cgt gga ggg ccc cca aga ccc aac aga ggg atg ccg caa     2295
Pro Arg Gly Arg Gly Gly Pro Pro Arg Pro Asn Arg Gly Met Pro Gln
            690                 695                 700

atg aac act cag caa gtg aat taa tctgattcac aggattatgt ttaatcgcca    2349
Met Asn Thr Gln Gln Val Asn
        705

aaaacacact ggccagtgta ccataatatg ttaccagaag agttattatc tatttgttct   2409

ccctttcagg aaacttattg taaagggact gttttcatcc cataaagaca ggactacaat   2469

tgtcagcttt ctattacctg gatatggaag gaaactattt ttactctgca tgttctgtcc   2529

taagcgtcat cttgagcctt gcacatgata ctcagattcc tcacccttgc ttaggagtaa   2589

aacaatatac tttacagggt gataataatc tccatagtta tttgaagtgg cttgaaaaag   2649

gcaagattga cttttatgac attggataaa atctacaaat cagccctcga gttattcaat   2709

gataactgac aaactaaatt atttccctag aaaggaagat gaaaggagtg gagtgtggtt   2769

tggcagaaca actgcatttc acagcttttc cagttaaatt ggagcactga acgttcagat   2829

gcataccaaa ttatgcatgg gtcctaatca cacatataag gctggctacc agctttgaca   2889

cagcactgtt catctggcca aacaactgtg gttaaaaaca catgtaaaat gctttttaac   2949

agctgatact gtataagaca aagccaagat gcaaaattag gctttgattg gcactttttg   3009

aaaaatatgc aacaaatatg ggatgtaatc cggatggccg cttctgtact taatgtgaaa   3069

tatttagata ccttttttgaa cacttaacag tttctttgag acaatgactt ttgtaaggat   3129

tggtactatc tatcattcct tatgacatgt acattgtctg tcactaatcc ttggattttg   3189

ctgtattgtc acctaaattg gtacaggtac tgatgaaaat ctctagtgga taatcataac   3249

actctcggtc acatgttttt ccttcagctt gaaagctttt ttttaaaagg aaaagatacc   3309

aaatgcctgc tgctaccacc cttttcaatt gctatctttt gaaaggcacc agtatgtgtt   3369

ttagattgat ttccctgttt cagggaaatc acggacagta gtttcagttc tgatggtata   3429

agcaaaacaa ataaaacgtt tataaaagtt gtatcttgaa acactggtgt tcaacagcta   3489

gcagcttatg tgattcaccc catgccacgt tagtgtcaca aattttatgg tttatctcca   3549

gcaacatttc tctagtactt gcacttatta tcttttgtct aatttaacct taactgaatt   3609

ctccgtttct cctggaggca tttatattca gtgataattc cttcccttag atgcataggg   3669

agagtctcta aatttgatgg aaatggacac ttgagtagtg acttagcctt atgtactctg   3729

ttggaatttg tgctagcagt ttgagcacta gttctgtgtg cctaggaagt taatgctgct   3789

tattgtctca ttctgacttc atggagaatt aatcccacct ttaagcaaag gctactaagt   3849

taatggtatt ttctgtgcag aaattaaatt ttattttcag catttagccc aggaattctt   3909

ccagtaggtg ctcagctatt taaaaacaaa actattctca aacattcatc attagacaac   3969

tggagttttt gctggttttg taacctacca aaatggatag gctgttgaac attccacatt   4029

caaaagtttt gtagggtggt gggaaatggg ggatcttcaa tgtttatttt aaaataaaat   4089

aaaataagtt cttgactttt ctcatgtgtg gttgtggtac atcatattgg aagggttaac   4149

ctgttacttt ggcaaatgag tatttttttg ctagcacctc cccttgcgtg ctttaaatga   4209

catctgcctg ggatgtacca caaccatatg ttacctgtat cttaggggaa tggataaaat   4269

atttgtggtt tactgggtaa tccctagatg atgtatgctt gcagtcctat ataaaactaa   4329

atttgctatc tgtgtagaaa ataatttcat gacatttaca atcaggactg aagtaagttc   4389

ttcacacagt gacctctgaa tcagtttcag agaagggatg ggggagaaaa tgccttctag   4449
```

```
gttttgaact tctatgcatt agtgcagatg ttgtgaatgt gtaaaggtgt tcatagtttg   4509

actgtttcta tgtatgtttt ttcaaagaat tgttcctttt tttgaactat aatttttctt   4569

tttttggtta ttttaccatc acagtttaaa tgtatatctt ttatgtctct actcagacca   4629

tatttttaaa ggggtgcctc attatggggc agagaacttt tcaataagtc tcattaagat   4689

ctgaatcttg gttctaagca ttctgtataa tatgtgattg cttgtcctag ctgcagaagg   4749

ccttttgttt ggtcaaatgc atattttagc agagtttcaa ggaaatgatt gtcacacatg   4809

tcactgtagc ctcttggtgt agcaagctca catacaaaat acttttgtat atgcataata   4869

taaatcatct catgtggata tgaaacttct tttttaaaac ttaaaaaggt agaatgttat   4929

tgattacctt gattagggca gttttatttc cagatcctaa taattcctaa aaaatatgga   4989

aaagtttttt ttcaatcatt gtaccttgat attaaaacaa atatccttta agtatttcta   5049

atcagttagc ttctacagtt cttttgtctc cttttatatg cagctcttac gtgggagact   5109

tttccactta aaggagacat agaatgtgtg cttattctca gaaggttcat taactgaggt   5169

gatgagttaa caactagttg agcagtcagc ttcctaagtg ttttaggaca tttgttcatt   5229

atattttccg tcatataact agaggaagtg gaatgcagat aagtgccgaa ttcaaaccct   5289

tcattttatg tttaagctcc tgaatctgca ttccacttgg gttgttttta agcattctaa   5349

attttagttg attataagtt agatttcaca gaatcagtat tgcccttgat cttgtccttt   5409

ttatggagtt aacggggagg aagacccctc aggaaaacga aagtaaattg ttaaggctca   5469

tcttcatacc tttttccatt ttgaatccta caaaaatact gcaaaagact agtgaatgtt   5529

taaaattaca ctagattaaa taatatgaaa gtc                                5562


<210> SEQ ID NO 2
<211> LENGTH: 709
<212> TYPE: PRT
<213> ORGANISM: Homo sapiens

<400> SEQUENCE: 2

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Gly Ala Ala Ala Pro Ala Ser Gln His Pro Ala Thr Gly Thr Gly Ala
        35                  40                  45

Val Gln Thr Glu Ala Met Lys Gln Ile Leu Gly Val Ile Asp Lys Lys
    50                  55                  60

Leu Arg Asn Leu Glu Lys Lys Lys Gly Lys Leu Asp Asp Tyr Gln Glu
65                  70                  75                  80

Arg Met Asn Lys Gly Glu Arg Leu Asn Gln Asp Gln Leu Asp Ala Val
                85                  90                  95

Ser Lys Tyr Gln Glu Val Thr Asn Asn Leu Glu Phe Ala Lys Glu Leu
            100                 105                 110

Gln Arg Ser Phe Met Ala Leu Ser Gln Asp Ile Gln Lys Thr Ile Lys
        115                 120                 125

Lys Thr Ala Arg Arg Glu Gln Leu Met Arg Glu Glu Ala Glu Gln Lys
    130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
                165                 170                 175

Ile Leu Ser Glu Glu Glu Leu Ser Leu Leu Asp Glu Phe Tyr Lys Leu
```

```
            180                 185                 190

Val Asp Pro Glu Arg Asp Met Ser Leu Arg Leu Asn Glu Gln Tyr Glu
        195                 200                 205

His Ala Ser Ile His Leu Trp Asp Leu Leu Glu Gly Lys Glu Lys Pro
    210                 215                 220

Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
                245                 250                 255

Cys Glu Glu Glu Glu Ala Ala Ser Ala Pro Ala Val Glu Asp Gln Val
            260                 265                 270

Pro Glu Ala Glu Pro Glu Pro Ala Glu Glu Tyr Thr Glu Gln Ser Glu
        275                 280                 285

Val Glu Ser Thr Glu Tyr Val Asn Arg Gln Phe Met Ala Glu Thr Gln
    290                 295                 300

Phe Thr Ser Gly Glu Lys Glu Gln Val Asp Glu Trp Thr Val Glu Thr
305                 310                 315                 320

Val Glu Val Val Asn Ser Leu Gln Gln Gln Pro Gln Ala Ala Ser Pro
                325                 330                 335

Ser Val Pro Glu Pro His Ser Leu Thr Pro Val Ala Gln Ala Asp Pro
            340                 345                 350

Leu Val Arg Arg Gln Arg Val Gln Asp Leu Met Ala Gln Met Gln Gly
        355                 360                 365

Pro Tyr Asn Phe Ile Gln Asp Ser Met Leu Asp Phe Glu Asn Gln Thr
    370                 375                 380

Leu Asp Pro Ala Ile Val Ser Ala Gln Pro Met Asn Pro Thr Gln Asn
385                 390                 395                 400

Met Asp Met Pro Gln Leu Val Cys Pro Pro Val His Ser Glu Ser Arg
                405                 410                 415

Leu Ala Gln Pro Asn Gln Val Pro Val Gln Pro Glu Ala Thr Gln Val
            420                 425                 430

Pro Leu Val Ser Ser Thr Ser Glu Gly Tyr Thr Ala Ser Gln Pro Leu
        435                 440                 445

Tyr Gln Pro Ser His Ala Thr Glu Gln Arg Pro Gln Lys Glu Pro Ile
    450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
                485                 490                 495

Thr Ser Lys Pro Leu His Ser Ser Gly Ile Asn Val Asn Ala Ala Pro
            500                 505                 510

Phe Gln Ser Met Gln Thr Val Phe Asn Met Asn Ala Pro Val Pro Pro
        515                 520                 525

Val Asn Glu Pro Glu Thr Leu Lys Gln Gln Asn Gln Tyr Gln Ala Ser
    530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
                565                 570                 575

Pro Asp Gln Ser His Gln Val Thr Gly Asn His Gln Gln Pro Pro Gln
            580                 585                 590

Gln Asn Thr Gly Phe Pro Arg Ser Asn Gln Pro Tyr Tyr Asn Ser Arg
        595                 600                 605
```

```
Gly Val Ser Arg Gly Gly Ser Arg Gly Ala Arg Gly Leu Met Asn Gly
    610                 615                 620

Tyr Arg Gly Pro Ala Asn Gly Phe Arg Gly Gly Tyr Asp Gly Tyr Arg
625                 630                 635                 640

Pro Ser Phe Ser Asn Thr Pro Asn Ser Gly Tyr Thr Gln Ser Gln Phe
                645                 650                 655

Ser Ala Pro Arg Asp Tyr Ser Gly Tyr Gln Arg Asp Gly Tyr Gln Gln
            660                 665                 670

Asn Phe Lys Arg Gly Ser Gly Gln Ser Gly Pro Arg Gly Ala Pro Arg
        675                 680                 685

Gly Arg Gly Gly Pro Pro Arg Pro Asn Arg Gly Met Pro Gln Met Asn
    690                 695                 700

Thr Gln Gln Val Asn
705


<210> SEQ ID NO 3
<211> LENGTH: 3553
<212> TYPE: DNA
<213> ORGANISM: Homo sapiens
<220> FEATURE:
<221> NAME/KEY: CDS
<222> LOCATION: (190)..(2274)
<223> OTHER INFORMATION:

<400> SEQUENCE: 3

cagagggctg ctggctggct aagtccctcc cgctcccggc tctcgcctca ctaggagcgg     60

ctctcggtgc agcgggacag ggcgaagcgg cctgcgccca cggagcgcgc gacactgccc    120

ggaagggacc gccacccttg ccccctcagc tgcccactcg tgatttccag cggcctccgc    180

gcgcgcacg atg ccc tcg gcc acc agc cac agc ggg agc ggc agc aag tcg    231
          Met Pro Ser Ala Thr Ser His Ser Gly Ser Gly Ser Lys Ser
          1               5                   10

tcc gga ccg cca ccg ccg tcg ggt tcc tcc ggg agt gag gcg gcc gcg      279
Ser Gly Pro Pro Pro Pro Ser Gly Ser Ser Gly Ser Glu Ala Ala Ala
15                  20                  25                  30

gga gcc ggg gcc gcc gcg ccg gct tct cag cac ccc gca acc ggc acc      327
Gly Ala Gly Ala Ala Ala Pro Ala Ser Gln His Pro Ala Thr Gly Thr
                35                  40                  45

ggc gct gtc cag acc gag gcc atg aag cag att ctc ggg gtg atc gac      375
Gly Ala Val Gln Thr Glu Ala Met Lys Gln Ile Leu Gly Val Ile Asp
            50                  55                  60

aag aaa ctt cgg aac ctg gag aag aaa aag ggt aag ctt gat gat tac      423
Lys Lys Leu Arg Asn Leu Glu Lys Lys Lys Gly Lys Leu Asp Asp Tyr
        65                  70                  75

cag gaa cga atg aac aaa ggg gaa agg ctt aat caa gat cag ctg gat      471
Gln Glu Arg Met Asn Lys Gly Glu Arg Leu Asn Gln Asp Gln Leu Asp
    80                  85                  90

gcc gtt tct aag tac cag gaa gtc aca aat aat ttg gag ttt gca aaa      519
Ala Val Ser Lys Tyr Gln Glu Val Thr Asn Asn Leu Glu Phe Ala Lys
95                  100                 105                 110

gaa tta cag agg agt ttc atg gca cta agt caa gat att cag aaa aca      567
Glu Leu Gln Arg Ser Phe Met Ala Leu Ser Gln Asp Ile Gln Lys Thr
                115                 120                 125

ata aag aag aca gca cgt cgg gag cag ctt atg aga gaa gaa gct gaa      615
Ile Lys Lys Thr Ala Arg Arg Glu Gln Leu Met Arg Glu Glu Ala Glu
            130                 135                 140

cag aaa cgt tta aaa act gta ctt gag cta cag tat gtt ttg gac aaa      663
Gln Lys Arg Leu Lys Thr Val Leu Glu Leu Gln Tyr Val Leu Asp Lys
        145                 150                 155

ttg gga gat gat gaa gtg cgg act gac ctg aaa caa ggt ttg aat gga      711
```

-continued

```
Leu Gly Asp Asp Glu Val Arg Thr Asp Leu Lys Gln Gly Leu Asn Gly
    160                 165                 170

gtg cca ata ttg tcc gaa gag gag ttg tca ttg ttg gat gaa ttc tat      759
Val Pro Ile Leu Ser Glu Glu Glu Leu Ser Leu Leu Asp Glu Phe Tyr
175                 180                 185                 190

aag cta gta gac cct gaa cgg gac atg agc ttg agg ttg aat gaa cag      807
Lys Leu Val Asp Pro Glu Arg Asp Met Ser Leu Arg Leu Asn Glu Gln
                195                 200                 205

tat gaa cat gcc tcc att cac ctg tgg gac ctg ctg gaa ggg aag gaa      855
Tyr Glu His Ala Ser Ile His Leu Trp Asp Leu Leu Glu Gly Lys Glu
            210                 215                 220

aaa cct gta tgt gga acc acc tat aaa gtt cta aag gaa att gtt gag      903
Lys Pro Val Cys Gly Thr Thr Tyr Lys Val Leu Lys Glu Ile Val Glu
        225                 230                 235

cgt gtt ttt cag tca aac tac ttt gac agc acc cac aac cac cag aat      951
Arg Val Phe Gln Ser Asn Tyr Phe Asp Ser Thr His Asn His Gln Asn
    240                 245                 250

ggg ctg tgt gag gaa gaa gag gca gcc tca gca cct gca gtt gaa gac      999
Gly Leu Cys Glu Glu Glu Glu Ala Ala Ser Ala Pro Ala Val Glu Asp
255                 260                 265                 270

cag gta cct gaa gct gaa cct gag cca gca gaa gag tac act gag caa     1047
Gln Val Pro Glu Ala Glu Pro Glu Pro Ala Glu Glu Tyr Thr Glu Gln
                275                 280                 285

agt gaa gtt gaa tca aca gag tat gta aat aga cag ttc atg gca gaa     1095
Ser Glu Val Glu Ser Thr Glu Tyr Val Asn Arg Gln Phe Met Ala Glu
            290                 295                 300

aca cag ttc acc agt ggt gaa aag gag cag gta gat gag tgg aca gtt     1143
Thr Gln Phe Thr Ser Gly Glu Lys Glu Gln Val Asp Glu Trp Thr Val
        305                 310                 315

gaa acg gtt gag gtg gta aat tca ctc cag cag caa cct cag gct gca     1191
Glu Thr Val Glu Val Val Asn Ser Leu Gln Gln Gln Pro Gln Ala Ala
    320                 325                 330

tcc cct tca gta cca gag ccc cac tct ttg act cca gtg gct cag gca     1239
Ser Pro Ser Val Pro Glu Pro His Ser Leu Thr Pro Val Ala Gln Ala
335                 340                 345                 350

gat ccc ctt gtg aga aga cag cga gta caa gac ctt atg gca caa atg     1287
Asp Pro Leu Val Arg Arg Gln Arg Val Gln Asp Leu Met Ala Gln Met
                355                 360                 365

cag ggt ccc tat aat ttc ata cag gat tca atg ctg gat ttt gaa aat     1335
Gln Gly Pro Tyr Asn Phe Ile Gln Asp Ser Met Leu Asp Phe Glu Asn
            370                 375                 380

cag aca ctt gat cct gcc att gta tct gca cag cct atg aat cca aca     1383
Gln Thr Leu Asp Pro Ala Ile Val Ser Ala Gln Pro Met Asn Pro Thr
        385                 390                 395

caa aac atg gac atg ccc cag ctg gtt tgc cct cca gtt cat tct gaa     1431
Gln Asn Met Asp Met Pro Gln Leu Val Cys Pro Pro Val His Ser Glu
    400                 405                 410

tct aga ctt gct cag cct aat caa gtt cct gta caa cca gaa gcg aca     1479
Ser Arg Leu Ala Gln Pro Asn Gln Val Pro Val Gln Pro Glu Ala Thr
415                 420                 425                 430

cag gtt cct ttg gta tca tcc aca agt gag ggg tac aca gca tct caa     1527
Gln Val Pro Leu Val Ser Ser Thr Ser Glu Gly Tyr Thr Ala Ser Gln
                435                 440                 445

ccc ttg tac cag cct tct cat gct aca gag caa cga cca cag aag gaa     1575
Pro Leu Tyr Gln Pro Ser His Ala Thr Glu Gln Arg Pro Gln Lys Glu
            450                 455                 460

cca att gat cag att cag gca aca atc tct tta aat aca gac cag act     1623
Pro Ile Asp Gln Ile Gln Ala Thr Ile Ser Leu Asn Thr Asp Gln Thr
        465                 470                 475

aca gca tca tca tcc ctt cct gct gcg tct cag cct caa gta ttt cag     1671
```

```
Thr Ala Ser Ser Ser Leu Pro Ala Ala Ser Gln Pro Gln Val Phe Gln
    480                 485                 490

gct ggg aca agc aaa cct tta cat agc agt gga atc aat gta aat gca      1719
Ala Gly Thr Ser Lys Pro Leu His Ser Ser Gly Ile Asn Val Asn Ala
495                 500                 505                 510

gct cca ttc caa tcc atg caa acg gtg ttc aat atg aat gcc cca gtt      1767
Ala Pro Phe Gln Ser Met Gln Thr Val Phe Asn Met Asn Ala Pro Val
                515                 520                 525

cct cct gtt aat gaa cca gaa act tta aaa cag caa aat cag tac cag      1815
Pro Pro Val Asn Glu Pro Glu Thr Leu Lys Gln Gln Asn Gln Tyr Gln
            530                 535                 540

gcc agt tat aac cag agc ttt tct agt cag cct cac caa gta gaa caa      1863
Ala Ser Tyr Asn Gln Ser Phe Ser Ser Gln Pro His Gln Val Glu Gln
        545                 550                 555

aca gag ctt cag caa gaa cag ctt caa aca gtg gtt ggc act tac cat      1911
Thr Glu Leu Gln Gln Glu Gln Leu Gln Thr Val Val Gly Thr Tyr His
    560                 565                 570

ggt tcc cca gac cag tcc cat caa gtg act ggt aac cac cag cag cct      1959
Gly Ser Pro Asp Gln Ser His Gln Val Thr Gly Asn His Gln Gln Pro
575                 580                 585                 590

cct cag cag aac act gga ttt cca cgt agc aat cag ccc tat tac aat      2007
Pro Gln Gln Asn Thr Gly Phe Pro Arg Ser Asn Gln Pro Tyr Tyr Asn
                595                 600                 605

agt cgt ggt gtg tct cgt gga ggc tcc cgt ggt gct aga ggc ttg atg      2055
Ser Arg Gly Val Ser Arg Gly Gly Ser Arg Gly Ala Arg Gly Leu Met
            610                 615                 620

aat gga tac cgg ggc cct gcc aat gga ttc aga gga gga tat gat ggt      2103
Asn Gly Tyr Arg Gly Pro Ala Asn Gly Phe Arg Gly Gly Tyr Asp Gly
        625                 630                 635

tac cgc cct tca ttc tct aac act cca aac agt ggt tat aca cag tct      2151
Tyr Arg Pro Ser Phe Ser Asn Thr Pro Asn Ser Gly Tyr Thr Gln Ser
    640                 645                 650

cag ttc agt gct ccc cgg gat tac tct ggc tat caa cgg gat gga tat      2199
Gln Phe Ser Ala Pro Arg Asp Tyr Ser Gly Tyr Gln Arg Asp Gly Tyr
655                 660                 665                 670

cag cag aat ttc aag cga ggc tct ggg cag agt gga cca cgg gga gcc      2247
Gln Gln Asn Phe Lys Arg Gly Ser Gly Gln Ser Gly Pro Arg Gly Ala
                675                 680                 685

cca cga ggt aat att ttg tgg tgg tga tcctagctcc taagtggagc            2294
Pro Arg Gly Asn Ile Leu Trp Trp
            690

ttctgttctg gccttggaag agctgttaat agtctgcatg ttaggaatac atttatcctt   2354

tccagacttg ttgctaggga ttaaatgaaa tgctctgttt ctaaaactta atcttggacc   2414

caaattttaa tttttgaatg atttaatttt ccctgttact atataaactg tcttgaaaac   2474

tagaacatat tctcttctca gaaaaagtgt tttttccaact gaaaattatt tttcaggtcc   2534

taaaacctgc taaatgtttt taggaagtac ttactgaaac atttttgtaa gacatttttg   2594

gaatgagatt gaacatttat ataaatttat tattcctctt tcattttttt gaaacatgcc   2654

tattatattt tagggccaga caccctttaa tggccggata agccatagtt aacatttaga   2714

gaaccattta gaagtgatag aactaatgga atttgcaatg ccttttggac ctctattagt   2774

gatataaata tcaagttatt tctgactttt aaacaaaact cccaaattcc taacttattg   2834

agctatactt aaaaaaaatt acaggtttag agagtttttt gtttttcttt tactgttgga   2894

aaactacttc ccattttggc aggaagttaa cctatttaac aattagagct agcatttcat   2954

gtagtctgaa attctaaatg gttctctgat ttgagggagg ttaaacatca aacaggtttc   3014

ctctattggc cataacatgt ataaaatgtg tgttaaggag gaattacaac gtactttgat   3074
```

ttgaatacta gtagaaactg gccaggaaaa aggtacattt ttctaaaaat taatggatca 3134 cttgggaatt actgacttga ctagaagtat caaaggatgt ttgcatgtga atgtgggtta 3194 tgttctttcc caccttgtag catattcgat gaaagttgag ttaactgata gctaaaaatc 3254 tgttttaaca gcatgtaaaa agttatttta tctgttaaaa gtcattatac agttttgaat 3314 gttatgtagt ttctttttaa cagtttaggt aataaggtct gttttcattc tggtgctttt 3374 attaattttg atagtatgat gttacttact actgaaatgt aagctagagt gtacactaga 3434 atgtaagctc catgagagca ggtaccttgt ctgtcttctc tgctgtatct attcccaacg 3494 cttgatgatg gtgcctggca catagtaggc actcaataaa tatttgttga atgaatgaa 3553

<210> SEQ ID NO 4
<211> LENGTH: 694
<212> TYPE: PRT
<213> ORGANISM: Homo sapiens

<400> SEQUENCE: 4

Met Pro Ser Ala Thr Ser His Ser Gly Ser Gly Ser Lys Ser Ser Gly
1 5 10 15

Pro Pro Pro Pro Ser Gly Ser Ser Gly Ser Glu Ala Ala Ala Gly Ala
20 25 30

Gly Ala Ala Ala Pro Ala Ser Gln His Pro Ala Thr Gly Thr Gly Ala
35 40 45

Val Gln Thr Glu Ala Met Lys Gln Ile Leu Gly Val Ile Asp Lys Lys
50 55 60

Leu Arg Asn Leu Glu Lys Lys Lys Gly Lys Leu Asp Asp Tyr Gln Glu
65 70 75 80

Arg Met Asn Lys Gly Glu Arg Leu Asn Gln Asp Gln Leu Asp Ala Val
85 90 95

Ser Lys Tyr Gln Glu Val Thr Asn Asn Leu Glu Phe Ala Lys Glu Leu
100 105 110

Gln Arg Ser Phe Met Ala Leu Ser Gln Asp Ile Gln Lys Thr Ile Lys
115 120 125

Lys Thr Ala Arg Arg Glu Gln Leu Met Arg Glu Glu Ala Glu Gln Lys
130 135 140

Arg Leu Lys Thr Val Leu Glu Leu Gln Tyr Val Leu Asp Lys Leu Gly
145 150 155 160

Asp Asp Glu Val Arg Thr Asp Leu Lys Gln Gly Leu Asn Gly Val Pro
165 170 175

Ile Leu Ser Glu Glu Glu Leu Ser Leu Leu Asp Glu Phe Tyr Lys Leu
180 185 190

Val Asp Pro Glu Arg Asp Met Ser Leu Arg Leu Asn Glu Gln Tyr Glu
195 200 205

His Ala Ser Ile His Leu Trp Asp Leu Leu Glu Gly Lys Glu Lys Pro
210 215 220

Val Cys Gly Thr Thr Tyr Lys Val Leu Lys Glu Ile Val Glu Arg Val
225 230 235 240

Phe Gln Ser Asn Tyr Phe Asp Ser Thr His Asn His Gln Asn Gly Leu
245 250 255

Cys Glu Glu Glu Glu Ala Ala Ser Ala Pro Ala Val Glu Asp Gln Val
260 265 270

Pro Glu Ala Glu Pro Glu Pro Ala Glu Glu Tyr Thr Glu Gln Ser Glu
275 280 285

Val Glu Ser Thr Glu Tyr Val Asn Arg Gln Phe Met Ala Glu Thr Gln

```
    290                 295                 300

Phe Thr Ser Gly Glu Lys Glu Gln Val Asp Glu Trp Thr Val Glu Thr
305                 310                 315                 320

Val Glu Val Val Asn Ser Leu Gln Gln Gln Pro Gln Ala Ala Ser Pro
                325                 330                 335

Ser Val Pro Glu Pro His Ser Leu Thr Pro Val Ala Gln Ala Asp Pro
            340                 345                 350

Leu Val Arg Arg Gln Arg Val Gln Asp Leu Met Ala Gln Met Gln Gly
        355                 360                 365

Pro Tyr Asn Phe Ile Gln Asp Ser Met Leu Asp Phe Glu Asn Gln Thr
    370                 375                 380

Leu Asp Pro Ala Ile Val Ser Ala Gln Pro Met Asn Pro Thr Gln Asn
385                 390                 395                 400

Met Asp Met Pro Gln Leu Val Cys Pro Pro Val His Ser Glu Ser Arg
                405                 410                 415

Leu Ala Gln Pro Asn Gln Val Pro Val Gln Pro Glu Ala Thr Gln Val
            420                 425                 430

Pro Leu Val Ser Ser Thr Ser Glu Gly Tyr Thr Ala Ser Gln Pro Leu
        435                 440                 445

Tyr Gln Pro Ser His Ala Thr Glu Gln Arg Pro Gln Lys Glu Pro Ile
    450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
                485                 490                 495

Thr Ser Lys Pro Leu His Ser Ser Gly Ile Asn Val Asn Ala Ala Pro
            500                 505                 510

Phe Gln Ser Met Gln Thr Val Phe Asn Met Asn Ala Pro Val Pro Pro
        515                 520                 525

Val Asn Glu Pro Glu Thr Leu Lys Gln Gln Asn Gln Tyr Gln Ala Ser
    530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
                565                 570                 575

Pro Asp Gln Ser His Gln Val Thr Gly Asn His Gln Gln Pro Pro Gln
            580                 585                 590

Gln Asn Thr Gly Phe Pro Arg Ser Asn Gln Pro Tyr Tyr Asn Ser Arg
        595                 600                 605

Gly Val Ser Arg Gly Gly Ser Arg Gly Ala Arg Gly Leu Met Asn Gly
    610                 615                 620

Tyr Arg Gly Pro Ala Asn Gly Phe Arg Gly Gly Tyr Asp Gly Tyr Arg
625                 630                 635                 640

Pro Ser Phe Ser Asn Thr Pro Asn Ser Gly Tyr Thr Gln Ser Gln Phe
                645                 650                 655

Ser Ala Pro Arg Asp Tyr Ser Gly Tyr Gln Arg Asp Gly Tyr Gln Gln
            660                 665                 670

Asn Phe Lys Arg Gly Ser Gly Gln Ser Gly Pro Arg Gly Ala Pro Arg
        675                 680                 685

Gly Asn Ile Leu Trp Trp
    690

<210> SEQ ID NO 5
<211> LENGTH: 1605
```

```
<212> TYPE: DNA
<213> ORGANISM: Canis familiaris
<220> FEATURE:
<221> NAME/KEY: CDS
<222> LOCATION: (46)..(1392)
<223> OTHER INFORMATION:

<400> SEQUENCE: 5

gtcacaaata acttggagtt tgcaaaagaa ttacagagga gtttc atg gca tta agt      57
                                                  Met Ala Leu Ser
                                                  1

caa gat att cag aaa aca ata aag aag act gca cgt cgg gag cag ctt      105
Gln Asp Ile Gln Lys Thr Ile Lys Lys Thr Ala Arg Arg Glu Gln Leu
5                   10                  15                  20

atg aga gag gaa gcg gaa caa aaa cgt tta aaa act gta ctt gag ctc      153
Met Arg Glu Glu Ala Glu Gln Lys Arg Leu Lys Thr Val Leu Glu Leu
                25                  30                  35

cag tat gtt ttg gac aaa ttg gga gat gat gaa gtg aga act gac ctg      201
Gln Tyr Val Leu Asp Lys Leu Gly Asp Asp Glu Val Arg Thr Asp Leu
            40                  45                  50

aag caa ggt ttg aat gga gtg cca ata ttg tct gaa gaa gaa ttg tcg      249
Lys Gln Gly Leu Asn Gly Val Pro Ile Leu Ser Glu Glu Glu Leu Ser
        55                  60                  65

ttg ttg gat gaa ttc tac aaa tta gca gac cct gaa cgg gac atg agc      297
Leu Leu Asp Glu Phe Tyr Lys Leu Ala Asp Pro Glu Arg Asp Met Ser
    70                  75                  80

ttg agg ttg aat gag cag tat gaa cat gct tcc att cac ctg tgg gac      345
Leu Arg Leu Asn Glu Gln Tyr Glu His Ala Ser Ile His Leu Trp Asp
85                  90                  95                  100

ttg ctg gaa gga aag gaa aag tct gta tgt gga aca acc tat aaa gca      393
Leu Leu Glu Gly Lys Glu Lys Ser Val Cys Gly Thr Thr Tyr Lys Ala
                105                 110                 115

cta aag gaa att gtt gag cgt gtt ttc cag tca aat tac ttt gac agc      441
Leu Lys Glu Ile Val Glu Arg Val Phe Gln Ser Asn Tyr Phe Asp Ser
            120                 125                 130

act cac aac cac cag aat ggg cta tgt gag gaa gaa gag gca gcc tca      489
Thr His Asn His Gln Asn Gly Leu Cys Glu Glu Glu Glu Ala Ala Ser
        135                 140                 145

gca cct aca gtt gaa gac cag gta gct gaa gct gag cct gag cca gca      537
Ala Pro Thr Val Glu Asp Gln Val Ala Glu Ala Glu Pro Glu Pro Ala
    150                 155                 160

gaa gaa tac act gaa caa agt gaa gtt gaa tca aca gag tat gta aat      585
Glu Glu Tyr Thr Glu Gln Ser Glu Val Glu Ser Thr Glu Tyr Val Asn
165                 170                 175                 180

aga caa ttt atg gca gaa aca cag ttc agc agt ggt gaa aag gag cag      633
Arg Gln Phe Met Ala Glu Thr Gln Phe Ser Ser Gly Glu Lys Glu Gln
                185                 190                 195

gta gat gag tgg acg gtc gaa aca gtg gag gtg gtg aat tca ctc cag      681
Val Asp Glu Trp Thr Val Glu Thr Val Glu Val Val Asn Ser Leu Gln
            200                 205                 210

cag caa cct cag gct gcg tct cct tca gta cca gag ccc cac tct ttg      729
Gln Gln Pro Gln Ala Ala Ser Pro Ser Val Pro Glu Pro His Ser Leu
        215                 220                 225

act ccg gtg gct cag gca gat ccc ctt gtg aga aga cag cga gtc cag      777
Thr Pro Val Ala Gln Ala Asp Pro Leu Val Arg Arg Gln Arg Val Gln
    230                 235                 240

gac ctt atg gcg cag atg cag ggg ccc tat aat ttc ata cag gat tca      825
Asp Leu Met Ala Gln Met Gln Gly Pro Tyr Asn Phe Ile Gln Asp Ser
245                 250                 255                 260

atg ctg gat ttt gaa aac cag aca ctc gat cct gcc att gta tct gca      873
Met Leu Asp Phe Glu Asn Gln Thr Leu Asp Pro Ala Ile Val Ser Ala
                265                 270                 275
```

```
cag cct atg aat ccg aca caa aac atg gac atg ccc cag ctg gtt tgc      921
Gln Pro Met Asn Pro Thr Gln Asn Met Asp Met Pro Gln Leu Val Cys
            280                 285                 290

cct cca gtt cat tct gaa tct aga ctt gct caa cct aat caa gtt cct      969
Pro Pro Val His Ser Glu Ser Arg Leu Ala Gln Pro Asn Gln Val Pro
        295                 300                 305

gta caa cca gaa gct aca cag gtt cct ttg gtt tca tcc aca agt gag     1017
Val Gln Pro Glu Ala Thr Gln Val Pro Leu Val Ser Ser Thr Ser Glu
    310                 315                 320

ggg tat aca gca tct caa ccc ttg tac cag cct tct cat gct aca gag     1065
Gly Tyr Thr Ala Ser Gln Pro Leu Tyr Gln Pro Ser His Ala Thr Glu
325                 330                 335                 340

caa cga cca caa aag gaa cca att gac cag att cag gca aca atc tct     1113
Gln Arg Pro Gln Lys Glu Pro Ile Asp Gln Ile Gln Ala Thr Ile Ser
                345                 350                 355

tta aat aca gac cag act aca gcg tca tca tcc ctt ccg gct gct tct     1161
Leu Asn Thr Asp Gln Thr Thr Ala Ser Ser Ser Leu Pro Ala Ala Ser
            360                 365                 370

cag cct cag gta ttc cag gct ggg aca agc aaa cca tta cat agc agt     1209
Gln Pro Gln Val Phe Gln Ala Gly Thr Ser Lys Pro Leu His Ser Ser
        375                 380                 385

gga atc aat gta aat gca gct cca ttc caa tcc atg caa acg gtg ttc     1257
Gly Ile Asn Val Asn Ala Ala Pro Phe Gln Ser Met Gln Thr Val Phe
    390                 395                 400

aat atg aat gcc cca gtt cct cct gtt aat gaa cca gaa act ttg aaa     1305
Asn Met Asn Ala Pro Val Pro Pro Val Asn Glu Pro Glu Thr Leu Lys
405                 410                 415                 420

caa caa aat cag tac cag gcc agt tat aac cag agc ttt tct agt cag     1353
Gln Gln Asn Gln Tyr Gln Ala Ser Tyr Asn Gln Ser Phe Ser Ser Gln
                425                 430                 435

cct cac caa gta gaa caa aca gag gga tgc cgc aaa tga acactcagca      1402
Pro His Gln Val Glu Gln Thr Glu Gly Cys Arg Lys
            440                 445

agtgaattaa tctgattcac aggattatgt ttaaacgcca aaaacacact ggccagtgta   1462

ccataatatg ttaccagaag agttattatc tatttgttct ccctttcagg aaacttattg   1522

taaagggact gttttcatcc cataaagaca ggactacaat tgtcagcttt atattacctg   1582

gaaaaaaaaa aaaaaaaaaa aaa                                            1605
```

<210> SEQ ID NO 6
<211> LENGTH: 448
<212> TYPE: PRT
<213> ORGANISM: Canis familiaris

<400> SEQUENCE: 6

```
Met Ala Leu Ser Gln Asp Ile Gln Lys Thr Ile Lys Lys Thr Ala Arg
1               5                   10                  15

Arg Glu Gln Leu Met Arg Glu Glu Ala Glu Gln Lys Arg Leu Lys Thr
            20                  25                  30

Val Leu Glu Leu Gln Tyr Val Leu Asp Lys Leu Gly Asp Asp Glu Val
        35                  40                  45

Arg Thr Asp Leu Lys Gln Gly Leu Asn Gly Val Pro Ile Leu Ser Glu
    50                  55                  60

Glu Glu Leu Ser Leu Leu Asp Glu Phe Tyr Lys Leu Ala Asp Pro Glu
65                  70                  75                  80

Arg Asp Met Ser Leu Arg Leu Asn Glu Gln Tyr Glu His Ala Ser Ile
                85                  90                  95

His Leu Trp Asp Leu Leu Glu Gly Lys Glu Lys Ser Val Cys Gly Thr
```

```
            100                 105                 110

Thr Tyr Lys Ala Leu Lys Glu Ile Val Glu Arg Val Phe Gln Ser Asn
        115                 120                 125

Tyr Phe Asp Ser Thr His Asn His Gln Asn Gly Leu Cys Glu Glu Glu
    130                 135                 140

Glu Ala Ala Ser Ala Pro Thr Val Glu Asp Gln Val Ala Glu Ala Glu
145                 150                 155                 160

Pro Glu Pro Ala Glu Glu Tyr Thr Glu Gln Ser Glu Val Glu Ser Thr
                165                 170                 175

Glu Tyr Val Asn Arg Gln Phe Met Ala Glu Thr Gln Phe Ser Ser Gly
            180                 185                 190

Glu Lys Glu Gln Val Asp Glu Trp Thr Val Glu Thr Val Glu Val Val
        195                 200                 205

Asn Ser Leu Gln Gln Gln Pro Gln Ala Ala Ser Pro Ser Val Pro Glu
    210                 215                 220

Pro His Ser Leu Thr Pro Val Ala Gln Ala Asp Pro Leu Val Arg Arg
225                 230                 235                 240

Gln Arg Val Gln Asp Leu Met Ala Gln Met Gln Gly Pro Tyr Asn Phe
                245                 250                 255

Ile Gln Asp Ser Met Leu Asp Phe Glu Asn Gln Thr Leu Asp Pro Ala
            260                 265                 270

Ile Val Ser Ala Gln Pro Met Asn Pro Thr Gln Asn Met Asp Met Pro
        275                 280                 285

Gln Leu Val Cys Pro Pro Val His Ser Glu Ser Arg Leu Ala Gln Pro
    290                 295                 300

Asn Gln Val Pro Val Gln Pro Glu Ala Thr Gln Val Pro Leu Val Ser
305                 310                 315                 320

Ser Thr Ser Glu Gly Tyr Thr Ala Ser Gln Pro Leu Tyr Gln Pro Ser
                325                 330                 335

His Ala Thr Glu Gln Arg Pro Gln Lys Glu Pro Ile Asp Gln Ile Gln
            340                 345                 350

Ala Thr Ile Ser Leu Asn Thr Asp Gln Thr Thr Ala Ser Ser Ser Leu
        355                 360                 365

Pro Ala Ala Ser Gln Pro Gln Val Phe Gln Ala Gly Thr Ser Lys Pro
    370                 375                 380

Leu His Ser Ser Gly Ile Asn Val Asn Ala Ala Pro Phe Gln Ser Met
385                 390                 395                 400

Gln Thr Val Phe Asn Met Asn Ala Pro Val Pro Pro Val Asn Glu Pro
                405                 410                 415

Glu Thr Leu Lys Gln Gln Asn Gln Tyr Gln Ala Ser Tyr Asn Gln Ser
            420                 425                 430

Phe Ser Ser Gln Pro His Gln Val Glu Gln Thr Glu Gly Cys Arg Lys
        435                 440                 445


<210> SEQ ID NO 7
<211> LENGTH: 4154
<212> TYPE: DNA
<213> ORGANISM: Canis familiaris
<220> FEATURE:
<221> NAME/KEY: CDS
<222> LOCATION: (1)..(2154)
<223> OTHER INFORMATION:

<400> SEQUENCE: 7

atg ccg tcg gcc acc agc ctc agc gga agc ggc agc aag tcg tcg ggc       48
Met Pro Ser Ala Thr Ser Leu Ser Gly Ser Gly Ser Lys Ser Ser Gly
1               5                   10                  15
```

```
ccg ccg ccc ccg tcg ggt tcc tcc ggg agc gag gcg gcg gcg gcg gcg        96
Pro Pro Pro Pro Ser Gly Ser Ser Gly Ser Glu Ala Ala Ala Ala Ala
            20                  25                  30

ggg gcg gcg ggg gcg gcg ggg gcc ggg gcg gct gcg ccc gcc tcc cag       144
Gly Ala Ala Gly Ala Ala Gly Ala Gly Ala Ala Ala Pro Ala Ser Gln
        35                  40                  45

cac ccc gcg acc ggc acc ggc gct gtc cag acc gag gcc atg aag cag       192
His Pro Ala Thr Gly Thr Gly Ala Val Gln Thr Glu Ala Met Lys Gln
    50                  55                  60

atc ctc ggg gtg atc gac aag aaa ctc cgg aac ctg gag aag aaa aag       240
Ile Leu Gly Val Ile Asp Lys Lys Leu Arg Asn Leu Glu Lys Lys Lys
65                  70                  75                  80

ggc aag ctt gat gat tac cag gaa cga atg aac aaa ggg gaa agg ctt       288
Gly Lys Leu Asp Asp Tyr Gln Glu Arg Met Asn Lys Gly Glu Arg Leu
                85                  90                  95

aat caa gat cag ctg gat gcc gta tct aag tac cag gaa gtc aca aat       336
Asn Gln Asp Gln Leu Asp Ala Val Ser Lys Tyr Gln Glu Val Thr Asn
            100                 105                 110

aac ttg gag ttt gca aaa gaa tta cag agg agt ttc atg gca tta agt       384
Asn Leu Glu Phe Ala Lys Glu Leu Gln Arg Ser Phe Met Ala Leu Ser
        115                 120                 125

caa gat att cag aaa aca ata aag aag act gca cgt cgg gag cag ctt       432
Gln Asp Ile Gln Lys Thr Ile Lys Lys Thr Ala Arg Arg Glu Gln Leu
    130                 135                 140

atg aga gag gaa gcg gaa caa aaa cgt tta aaa act gta ctt gag ctc       480
Met Arg Glu Glu Ala Glu Gln Lys Arg Leu Lys Thr Val Leu Glu Leu
145                 150                 155                 160

cag tat gtt ttg gac aaa ttg gga gat gat gaa gtg aga act gac ctg       528
Gln Tyr Val Leu Asp Lys Leu Gly Asp Asp Glu Val Arg Thr Asp Leu
                165                 170                 175

aag caa ggt ttg aat gga gtg cca ata ttg tct gaa gaa gaa ttg tcg       576
Lys Gln Gly Leu Asn Gly Val Pro Ile Leu Ser Glu Glu Glu Leu Ser
            180                 185                 190

ttg ttg gat gaa ttc tac aaa tta gca gac cct gaa cgg gac atg agc       624
Leu Leu Asp Glu Phe Tyr Lys Leu Ala Asp Pro Glu Arg Asp Met Ser
        195                 200                 205

ttg agg ttg aat gag cag tat gaa cat gct tcc att cac ctg tgg gac       672
Leu Arg Leu Asn Glu Gln Tyr Glu His Ala Ser Ile His Leu Trp Asp
    210                 215                 220

ttg ctg gaa gga aag gaa aag tct gta tgt gga aca acc tat aaa gca       720
Leu Leu Glu Gly Lys Glu Lys Ser Val Cys Gly Thr Thr Tyr Lys Ala
225                 230                 235                 240

cta aag gaa att gtt gag cgt gtt ttc cag tca aat tac ttt gac agc       768
Leu Lys Glu Ile Val Glu Arg Val Phe Gln Ser Asn Tyr Phe Asp Ser
                245                 250                 255

act cac aac cac cag aat ggg cta tgt gag gaa gaa gag gca gcc tca       816
Thr His Asn His Gln Asn Gly Leu Cys Glu Glu Glu Glu Ala Ala Ser
            260                 265                 270

gca cct aca gtt gaa gac cag gta gct gaa gct gag cct gag cca gca       864
Ala Pro Thr Val Glu Asp Gln Val Ala Glu Ala Glu Pro Glu Pro Ala
        275                 280                 285

gaa gaa tac act gaa caa agt gaa gtt gaa tca aca gag tat gta aat       912
Glu Glu Tyr Thr Glu Gln Ser Glu Val Glu Ser Thr Glu Tyr Val Asn
    290                 295                 300

aga caa ttt atg gca gaa aca cag ttc agc agt ggt gaa aag gag cag       960
Arg Gln Phe Met Ala Glu Thr Gln Phe Ser Ser Gly Glu Lys Glu Gln
305                 310                 315                 320

gta gat gag tgg acg gtc gaa aca gtg gag gtg gtg aat tca ctc cag      1008
Val Asp Glu Trp Thr Val Glu Thr Val Glu Val Val Asn Ser Leu Gln
                325                 330                 335
```

```
cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350

act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365

gac ctt atg gcg cag atg cag ggg ccc tat aat ttc ata cag gat tca     1152
Asp Leu Met Ala Gln Met Gln Gly Pro Tyr Asn Phe Ile Gln Asp Ser
    370                 375                 380

atg ctg gat ttt gaa aac cag aca ctc gat cct gcc att gta tct gca     1200
Met Leu Asp Phe Glu Asn Gln Thr Leu Asp Pro Ala Ile Val Ser Ala
385                 390                 395                 400

cag cct atg aat ccg aca caa aac atg gac atg ccc cag ctg gtt tgc     1248
Gln Pro Met Asn Pro Thr Gln Asn Met Asp Met Pro Gln Leu Val Cys
                405                 410                 415

cct cca gtt cat tct gaa tct aga ctt gct caa cct aat caa gtt cct     1296
Pro Pro Val His Ser Glu Ser Arg Leu Ala Gln Pro Asn Gln Val Pro
            420                 425                 430

gta caa cca gaa gct aca cag gtt cct ttg gtt tca tcc aca agt gag     1344
Val Gln Pro Glu Ala Thr Gln Val Pro Leu Val Ser Ser Thr Ser Glu
        435                 440                 445

ggg tat aca gca tct caa ccc ttg tac cag cct tct cat gct aca gag     1392
Gly Tyr Thr Ala Ser Gln Pro Leu Tyr Gln Pro Ser His Ala Thr Glu
    450                 455                 460

caa cga cca caa aag gaa cca att gac cag att cag gca aca atc tct     1440
Gln Arg Pro Gln Lys Glu Pro Ile Asp Gln Ile Gln Ala Thr Ile Ser
465                 470                 475                 480

tta aat aca gac cag act aca gcg tca tca tcc ctt ccg gct gct tct     1488
Leu Asn Thr Asp Gln Thr Thr Ala Ser Ser Ser Leu Pro Ala Ala Ser
                485                 490                 495

cag cct cag gta ttc cag gct ggg aca agc aaa cca tta cat agc agt     1536
Gln Pro Gln Val Phe Gln Ala Gly Thr Ser Lys Pro Leu His Ser Ser
            500                 505                 510

gga atc aat gta aat gca gct cca ttc caa tcc atg caa acg gtg ttc     1584
Gly Ile Asn Val Asn Ala Ala Pro Phe Gln Ser Met Gln Thr Val Phe
        515                 520                 525

aat atg aat gcc cca gtt cct cct gtt aat gaa cca gaa act ttg aaa     1632
Asn Met Asn Ala Pro Val Pro Pro Val Asn Glu Pro Glu Thr Leu Lys
    530                 535                 540

caa caa aat cag tac cag gcc agt tat aac cag agc ttt tct agt cag     1680
Gln Gln Asn Gln Tyr Gln Ala Ser Tyr Asn Gln Ser Phe Ser Ser Gln
545                 550                 555                 560

cct cac caa gta gaa caa aca gac ctt cag caa gaa cag ctt caa aca     1728
Pro His Gln Val Glu Gln Thr Asp Leu Gln Gln Glu Gln Leu Gln Thr
                565                 570                 575

gtg gtt ggc act tac cat ggt tcc cag gac cag ccc cac caa gtg act     1776
Val Val Gly Thr Tyr His Gly Ser Gln Asp Gln Pro His Gln Val Thr
            580                 585                 590

ggt aac cat cag cag cct ccc cag cag aac act gga ttt cca cgt agc     1824
Gly Asn His Gln Gln Pro Pro Gln Gln Asn Thr Gly Phe Pro Arg Ser
        595                 600                 605

agt cag ccc tat tac aat agt cgt ggt gtg tct cgt ggt ggt tcc cgt     1872
Ser Gln Pro Tyr Tyr Asn Ser Arg Gly Val Ser Arg Gly Gly Ser Arg
    610                 615                 620

ggt gct aga ggc tta atg aat gga tac agg ggc cct gcc aat gga ttc     1920
Gly Ala Arg Gly Leu Met Asn Gly Tyr Arg Gly Pro Ala Asn Gly Phe
625                 630                 635                 640

aga gga gga tat gat ggt tac cgc cct tca ttc tct aac act cca aac     1968
Arg Gly Gly Tyr Asp Gly Tyr Arg Pro Ser Phe Ser Asn Thr Pro Asn
                645                 650                 655
```

```
agt ggt tat aca cag tct cag ttc agt gct ccc cgg gac tac tct ggc     2016
Ser Gly Tyr Thr Gln Ser Gln Phe Ser Ala Pro Arg Asp Tyr Ser Gly
            660                 665                 670

tat cag cgg gat gga tat cag cag aat ttc aag cga ggc tct ggg cag     2064
Tyr Gln Arg Asp Gly Tyr Gln Gln Asn Phe Lys Arg Gly Ser Gly Gln
        675                 680                 685

agt gga cca cgg gga gcc cca cga ggt cgt gga ggg ccc cca aga ccc     2112
Ser Gly Pro Arg Gly Ala Pro Arg Gly Arg Gly Gly Pro Pro Arg Pro
    690                 695                 700

aac aga ggg atg ccg caa atg aac act cag caa gtg aat taa             2154
Asn Arg Gly Met Pro Gln Met Asn Thr Gln Gln Val Asn
705                 710                 715

tctgattcac aggattatgt ttaaacgcca aaaacacact ggccagtgta ccataatatg   2214

ttaccagaag agttattatc tatttgttct ccctttcagg aaacttattg taaagggact   2274

gttttcatcc cataaagaca ggactacaat tgtcagcttt atattacctg gatatggaag   2334

gaaactattt ttattctgca tgttcttcct aagcgtcatc ttgagccttg cacatgatac   2394

tcagattcct caccccttgct taggagtaaa acataataca ctttacaggg tgatatctcc   2454

atagttattt gaagtggctt ggaaaaagca agattaactt ctgacattgg ataaaaatca   2514

acaaatcagc cctagagtta ttcaaatggt aattgacaaa aactaaaata tttcccttcg   2574

agaaggagtg gaatgtggtt tggcagaaca actgcatttc acagcttttc cggttaaatt   2634

ggagcactaa acgtttagat gcataccaaa ttatgcatgg gcccttaata taaaaggctg   2694

gctaccagct ttgacacagc actattcatc ctctggccaa acaactgtgg ttaaacaaca   2754

catgtaaatt gctttttaac agctgatact ataataagac aaagccaaaa tgcaaaaatt   2814

gggctttgat tggcactttt tgaaaaatat gcaacaaata tgggatgtaa tctggatggc   2874

cgcttctgta cttaatgtga agtatttaga tacctttttg aacacttaac agtttcttct   2934

gacaatgact tttgtaagga ttggtactat ctatcattcc ttataatgta cattgtctgt   2994

cactaatcct cagatcttgc tgtattgtca cctaaattgg tacaggtact gatgaaaata   3054

tctaatggat aatcataaca ctcttggtca catgttttc ctgcagcctg aaggttttta    3114

aaagaaaaag atatcaaatg cctgctgcta ccaccctttt aaattgctat cttttgaaaa   3174

gcaccagtat gtgttttaga ttgatttccc tattttaggg aaatgacaga cagtagtttc   3234

agttctgatg gtataagcaa aacaaataaa acatgtttat aaaagttgta tcttgaaaca   3294

ctggtgttca acagctagca gcttatgtgg ttcaccccat gcattgttag tgtttcagat   3354

tttatggtta tctccagcag ctgtttctgt agtacttgca tttatctttt gtctaaccct   3414

aatattctca cggaggcatt tatattcaaa gtggtgatcc cttcacttag acgcataggg   3474

agagtcacaa gtttgatgaa gaggacagtg tagtaattta tatgctgttg gaatttgtgc   3534

tagcagtttg agcactagtt ctgtgtgcct atgaacttaa tgctgcttgt catattccac   3594

tttgacttca tggagaatta atcccatcta ctcagcaaag gctatactaa tactaagtta   3654

atggtatttt ctgtgcagaa attgaatttt gttttattag catttagcta aggaattttt   3714

ccagtaggtg ctcagctact aaagaaaaac aaaaacaaga cacaaaacta ttctcaaaca   3774

ttcattgtta gacaactgga gtttttgctg gttttgtaac ctactaaaat ggataggctg   3834

ttgaacattc cacattcaaa agtttttgt agggtggtgg ggaagggggg gtgtcttcaa    3894

tgtttatttt aaaataaaat aagttcttga cttttctcat gtgtggttgt ggtacatcat   3954

attggaaggg ttatctgttt acttttgcaa atgagtattt ctcttgctag cacctcccgt   4014

tgtgcgcttt aaatgacatc tgcctgggat gtaccacaac catatgttag ctgtatttta   4074
```

```
tggggaatag ataaaatatt cgtggtttat tgggtaatcc ctagatgtgt atgcttacaa   4134

tcctatatat aaaactaaat                                                4154


<210> SEQ ID NO 8
<211> LENGTH: 717
<212> TYPE: PRT
<213> ORGANISM: Canis familiaris

<400> SEQUENCE: 8

Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Glu Ala Ala Ser
            260                 265                 270

Ala Pro Thr Val Glu Asp Gln Val Ala Glu Ala Glu Pro Glu Pro Ala
        275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
```

```
        355                 360                 365

Asp Leu Met Ala Gln Met Gln Gly Pro Tyr Asn Phe Ile Gln Asp Ser
    370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
            420                 425                 430

Val Gln Pro Glu Ala Thr Gln Val Pro Leu Val Ser Ser Thr Ser Glu
        435                 440                 445

Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
    530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Asp Gly Tyr Gln Gln Asn Phe Lys Arg Gly Ser Gly Gln
        675                 680                 685

Ser Gly Pro Arg Gly Ala Pro Arg Gly Arg Gly Gly Pro Pro Arg Pro
    690                 695                 700

Asn Arg Gly Met Pro Gln Met Asn Thr Gln Gln Val Asn
705                 710                 715
```

<210> SEQ ID NO 9
<211> LENGTH: 4939
<212> TYPE: DNA
<213> ORGANISM: Canis familiaris
<220> FEATURE:
<221> NAME/KEY: CDS
<222> LOCATION: (1)..(2109)
<223> OTHER INFORMATION:

<400> SEQUENCE: 9

```
atg ccg tcg gcc acc agc ctc agc gga agc ggc agc aag tcg tcg ggc       48
Met Pro Ser Ala Thr Ser Leu Ser Gly Ser Gly Ser Lys Ser Ser Gly
1               5                   10                  15

ccg ccg ccc ccg tcg ggt tcc tcc ggg agc gag gcg gcg gcg gcg gcg       96
Pro Pro Pro Pro Ser Gly Ser Ser Gly Ser Glu Ala Ala Ala Ala Ala
            20                  25                  30

ggg gcg gcg ggg gcg gcg ggg gcc ggg gcg gct gcg ccc gcc tcc cag      144
Gly Ala Ala Gly Ala Ala Gly Ala Gly Ala Ala Ala Pro Ala Ser Gln
        35                  40                  45

cac ccc gcg acc ggc acc ggc gct gtc cag acc gag gcc atg aag cag      192
His Pro Ala Thr Gly Thr Gly Ala Val Gln Thr Glu Ala Met Lys Gln
    50                  55                  60

atc ctc ggg gtg atc gac aag aaa ctc cgg aac ctg gag aag aaa aag      240
Ile Leu Gly Val Ile Asp Lys Lys Leu Arg Asn Leu Glu Lys Lys Lys
65                  70                  75                  80

ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
                85                  90                  95

aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110

aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125

caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140

atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160

cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175

aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190

ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205

ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220

ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240

cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255

act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270

gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285

gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300

aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320
```

```
gta gat gag tgg acg gtc gaa aca gtg gag gtg gtg aat tca ctc cag      1008
Val Asp Glu Trp Thr Val Glu Thr Val Glu Val Val Asn Ser Leu Gln
                325                 330                 335

cag caa cct cag gct gcg tct cct tca gta cca gag ccc cac tct ttg      1056
Gln Gln Pro Gln Ala Ala Ser Pro Ser Val Pro Glu Pro His Ser Leu
            340                 345                 350

act ccg gtg gct cag gca gat ccc ctt gtg aga aga cag cga gtc cag      1104
Thr Pro Val Ala Gln Ala Asp Pro Leu Val Arg Arg Gln Arg Val Gln
        355                 360                 365

gac ctt atg gcg cag atg cag ggg ccc tat aat ttc ata cag gat tca      1152
Asp Leu Met Ala Gln Met Gln Gly Pro Tyr Asn Phe Ile Gln Asp Ser
    370                 375                 380

atg ctg gat ttt gaa aac cag aca ctc gat cct gcc att gta tct gca      1200
Met Leu Asp Phe Glu Asn Gln Thr Leu Asp Pro Ala Ile Val Ser Ala
385                 390                 395                 400

cag cct atg aat ccg aca caa aac atg gac atg ccc cag ctg gtt tgc      1248
Gln Pro Met Asn Pro Thr Gln Asn Met Asp Met Pro Gln Leu Val Cys
                405                 410                 415

cct cca gtt cat tct gaa tct aga ctt gct caa cct aat caa gtt cct      1296
Pro Pro Val His Ser Glu Ser Arg Leu Ala Gln Pro Asn Gln Val Pro
            420                 425                 430

gta caa cca gaa gct aca cag gtt cct ttg gtt tca tcc aca agt gag      1344
Val Gln Pro Glu Ala Thr Gln Val Pro Leu Val Ser Ser Thr Ser Glu
        435                 440                 445

ggg tat aca gca tct caa ccc ttg tac cag cct tct cat gct aca gag      1392
Gly Tyr Thr Ala Ser Gln Pro Leu Tyr Gln Pro Ser His Ala Thr Glu
    450                 455                 460

caa cga cca caa aag gaa cca att gac cag att cag gca aca atc tct      1440
Gln Arg Pro Gln Lys Glu Pro Ile Asp Gln Ile Gln Ala Thr Ile Ser
465                 470                 475                 480

tta aat aca gac cag act aca gcg tca tca tcc ctt ccg gct gct tct      1488
Leu Asn Thr Asp Gln Thr Thr Ala Ser Ser Ser Leu Pro Ala Ala Ser
                485                 490                 495

cag cct cag gta ttc cag gct ggg aca agc aaa cca tta cat agc agt      1536
Gln Pro Gln Val Phe Gln Ala Gly Thr Ser Lys Pro Leu His Ser Ser
            500                 505                 510

gga atc aat gta aat gca gct cca ttc caa tcc atg caa acg gtg ttc      1584
Gly Ile Asn Val Asn Ala Ala Pro Phe Gln Ser Met Gln Thr Val Phe
        515                 520                 525

aat atg aat gcc cca gtt cct cct gtt aat gaa cca gaa act ttg aaa      1632
Asn Met Asn Ala Pro Val Pro Pro Val Asn Glu Pro Glu Thr Leu Lys
    530                 535                 540

caa caa aat cag tac cag gcc agt tat aac cag agc ttt tct agt cag      1680
Gln Gln Asn Gln Tyr Gln Ala Ser Tyr Asn Gln Ser Phe Ser Ser Gln
545                 550                 555                 560

cct cac caa gta gaa caa aca gac ctt cag caa gaa cag ctt caa aca      1728
Pro His Gln Val Glu Gln Thr Asp Leu Gln Gln Glu Gln Leu Gln Thr
                565                 570                 575

gtg gtt ggc act tac cat ggt tcc cag gac cag ccc cac caa gtg act      1776
Val Val Gly Thr Tyr His Gly Ser Gln Asp Gln Pro His Gln Val Thr
            580                 585                 590

ggt aac cat cag cag cct ccc cag cag aac act gga ttt cca cgt agc      1824
Gly Asn His Gln Gln Pro Pro Gln Gln Asn Thr Gly Phe Pro Arg Ser
        595                 600                 605

agt cag ccc tat tac aat agt cgt ggt gtg tct cgt ggt ggt tcc cgt      1872
Ser Gln Pro Tyr Tyr Asn Ser Arg Gly Val Ser Arg Gly Gly Ser Arg
    610                 615                 620

ggt gct aga ggc tta atg aat gga tac agg ggc cct gcc aat gga ttc      1920
Gly Ala Arg Gly Leu Met Asn Gly Tyr Arg Gly Pro Ala Asn Gly Phe
625                 630                 635                 640
```

```
aga gga gga tat gat ggt tac cgc cct tca ttc tct aac act cca aac     1968
Arg Gly Gly Tyr Asp Gly Tyr Arg Pro Ser Phe Ser Asn Thr Pro Asn
                645                 650                 655

agt ggt tat aca cag tct cag ttc agt gct ccc cgg gac tac tct ggc     2016
Ser Gly Tyr Thr Gln Ser Gln Phe Ser Ala Pro Arg Asp Tyr Ser Gly
            660                 665                 670

tat cag cgg gat gga tat cag cag aat ttc aag cga ggc tct ggg cag     2064
Tyr Gln Arg Asp Gly Tyr Gln Gln Asn Phe Lys Arg Gly Ser Gly Gln
        675                 680                 685

agt gga cca cgg gga gcc cca cga ggt aat att ttg tgg tgg tga         2109
Ser Gly Pro Arg Gly Ala Pro Arg Gly Asn Ile Leu Trp Trp
    690                 695                 700

tcctagctcc taagtggagc ttctgttctg gccttggaag agctgttcca tagtctgcat   2169

gtaggttaca tgttaggaat acatttatca ttaccagact tgttgctagg gattaaatga   2229

aatgctctgt ttctaaaact tctcttgaac ccaaatttaa tttttgaat gactttccct    2289

gttactatat aaattgtctt gaaaactaga acatttctcc tcctcagaaa aagtgttttt   2349

ccaactgcaa attattttc aggtcctaaa acctgctaaa tgtttttagg aagtacttac    2409

tgaaacattt ttgtaagaca tttttggaat gagattgaac atttatataa atttattatt   2469

attcctcttt catttttgaa catgcatatt atattttagg gtcagaaatc ctttaatggc   2529

caaataagcc atagttacat ttagagaacc atttagaagt gatagaacta actgaaattt   2589

caatgccttt ggatcattaa tagcgatata aatttcaaat tgtttctgac ttttaaataa   2649

aacatccaaa atcctaacta acttcctgaa ctatatttaa aaattacagg tttaaggagt   2709

ttctggtttt ttttctctta ccataggaaa actgtttcct gtttggccag gaagtcaacc   2769

tgtgtaataa ttagaagtag catttcatat gatctgaagt tctaaatggt tctctgattt   2829

aagggaagtt aaattgaata ggtttcctct agttattggc cataacatgt ataaaatgta   2889

tattaaggag gaatacaaag tactttgatt tcaatgctag tagaaactgg ccagcaaaaa   2949

ggtgcatttt atttttaaat taatggatca cttgggaatt actgacttga agtatcaaag   3009

gatatttgca tgtgaatgtg ggttatgttc tttctcacct tgtagcatat tctatgaaag   3069

ttgagttgac tggtagctaa aaatctgttt taacagcatg taaaaagtta ttttatctgt   3129

tacaagtcat tatacaattt tgaatgttat gtagtttctt tttaacagtt taggtaacaa   3189

ggtctgtttt tcattctggt gcttttatta attttgatag tatgatgtta cttactactg   3249

aaatgtaagc tagagtgtac actagaatgt aagctccatg agagcaggta ccttgtctgt   3309

cttcactgct gtatctattt ccaacgcctg atgacagtgc ctgacacata gtaggcactc   3369

aataaatact tgttgaatga atgaatgaat gagtactggt ggaatactcc attagctcta   3429

ctcttctttt agctagagaa catgagcaaa tttgcgcatg acaacttcca ggacaggtga   3489

acactgaaga attgacctct taaacctaat aatgtggtga caagctgccc acatgcttct   3549

tgacttcaga tgaaaatctg cttgaaggca aagcaaataa tatttgaaag aaaaaccaaa   3609

tgccattttt gtcttctagg tcgtggaggg cccccaagac ccaacagagg gatgccgcaa   3669

atgaacactc agcaagtgaa ttaatctgat tcacaggatt atgtttaaac gccaaaaaca   3729

cactggccag tgtaccataa tatgttacca gaagagttat tatctatttg ttctcccttt   3789

caggaaactt attgtaaagg gactgttttc atcccataaa gacaggacta caattgtcag   3849

ctttatatta cctggatatg gaaggaaact atttttattc tgcatgttct tcctaagcgt   3909

catcttgagc cttgcacatg atactcagat tcctcaccct tgcttaggag taaaacataa   3969

tacactttac agggtgatat ctccatagtt atttgaagtg gcttggaaaa agcaagatta   4029
```

```
acttctgaca ttggataaaa atcaacaaat cagccctaga gttattcaaa tggtaattga   4089

caaaaactaa aatatttccc ttcgagaagg agtggaatgt ggtttggcag aacaactgca   4149

tttcacagct tttccggtta aattggagca ctaaacgttt agatgcatac caaattatgc   4209

atgggccctt aatataaaag gctggctacc agctttgaca cagcactatt catcctctgg   4269

ccaaacaact gtggttaaac aacacatgta aattgctttt taacagctga tactataata   4329

agacaaagcc aaaatgcaaa aattgggctt tgattggcac tttttgaaaa atatgcaaca   4389

aatatgggat gtaatctgga tggccgcttc tgtacttaat gtgaagtatt tagatacctt   4449

tttgaacact taacagtttc ttctgacaat gacttttgta aggattggta ctatctatca   4509

ttccttataa tgtacattgt ctgtcactaa tcctcagatc ttgctgtatt gtcacctaaa   4569

ttggtacagg tactgatgaa aatatctaat ggataatcat aacactcttg gtcacatgtt   4629

tttcctgcag cctgaaggtt tttaaaagaa aaagatatca aatgcctgct gctaccaccc   4689

ttttaaattg ctatcttttg aaaagcacca gtatgtgttt tagattgatt tccctatttt   4749

agggaaatga cagacagtag tttcagttct gatggtataa gcaaaacaaa taaaacatgt   4809

ttataaaagt tgtatcttga aacactggtg ttcaacagct agcagcttat gtggttcacc   4869

ccatgcattg ttagtgtttc agattttatg gttatctcca gcagctgttt ctgtagtact   4929

tgcatttatc                                                          4939
```

```
<210> SEQ ID NO 10
<211> LENGTH: 702
<212> TYPE: PRT
<213> ORGANISM: Canis familiaris

<400> SEQUENCE: 10

Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
```

```
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Glu Ala Ala Ser
            260                 265                 270

Ala Pro Thr Val Glu Asp Gln Val Ala Glu Ala Glu Pro Glu Pro Ala
        275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
        355                 360                 365

Asp Leu Met Ala Gln Met Gln Gly Pro Tyr Asn Phe Ile Gln Asp Ser
    370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
            420                 425                 430

Val Gln Pro Glu Ala Thr Gln Val Pro Leu Val Ser Ser Thr Ser Glu
        435                 440                 445

Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
    530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640
```

```
Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Asp Gly Tyr Gln Gln Asn Phe Lys Arg Gly Ser Gly Gln
        675                 680                 685

Ser Gly Pro Arg Gly Ala Pro Arg Gly Asn Ile Leu Trp Trp
    690                 695                 700


<210> SEQ ID NO 11
<211> LENGTH: 3306
<212> TYPE: DNA
<213> ORGANISM: Canis familiaris
<220> FEATURE:
<221> NAME/KEY: CDS
<222> LOCATION: (1)..(2040)
<223> OTHER INFORMATION:

<400> SEQUENCE: 11

atg ccg tcg gcc acc agc ctc agc gga agc ggc agc aag tcg tcg ggc       48
Met Pro Ser Ala Thr Ser Leu Ser Gly Ser Gly Ser Lys Ser Ser Gly
1               5                   10                  15

ccg ccg ccc ccg tcg ggt tcc tcc ggg agc gag gcg gcg gcg gcg gcg       96
Pro Pro Pro Pro Ser Gly Ser Ser Gly Ser Glu Ala Ala Ala Ala Ala
            20                  25                  30

ggg gcg gcg ggg gcg gcg ggg gcc ggg gcg gct gcg ccc gcc tcc cag      144
Gly Ala Ala Gly Ala Ala Gly Ala Gly Ala Ala Ala Pro Ala Ser Gln
        35                  40                  45

cac ccc gcg acc ggc acc ggc gct gtc cag acc gag gcc atg aag cag      192
His Pro Ala Thr Gly Thr Gly Ala Val Gln Thr Glu Ala Met Lys Gln
    50                  55                  60

atc ctc ggg gtg atc gac aag aaa ctc cgg aac ctg gag aag aaa aag      240
Ile Leu Gly Val Ile Asp Lys Lys Leu Arg Asn Leu Glu Lys Lys Lys
65                  70                  75                  80

ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
                85                  90                  95

aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110

aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125

caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140

atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160

cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175

aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190

ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205

ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220
```

```
ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240

cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255

act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270

gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285

gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300

aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320

gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335

cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350

act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365

gac ctt atg gcg cag atg cag ggg ccc tat aat ttc ata cag gat tca     1152
Asp Leu Met Ala Gln Met Gln Gly Pro Tyr Asn Phe Ile Gln Asp Ser
    370                 375                 380

atg ctg gat ttt gaa aac cag aca ctc gat cct gcc att gta tct gca     1200
Met Leu Asp Phe Glu Asn Gln Thr Leu Asp Pro Ala Ile Val Ser Ala
385                 390                 395                 400

cag cct atg aat ccg aca caa aac atg gac atg ccc cag ctg gtt tgc     1248
Gln Pro Met Asn Pro Thr Gln Asn Met Asp Met Pro Gln Leu Val Cys
                405                 410                 415

cct cca gtt cat tct gaa tct aga ctt gct caa cct aat caa gtt cct     1296
Pro Pro Val His Ser Glu Ser Arg Leu Ala Gln Pro Asn Gln Val Pro
            420                 425                 430

gta caa cca gaa gct aca cag gtt cct ttg gtt tca tcc aca agt gag     1344
Val Gln Pro Glu Ala Thr Gln Val Pro Leu Val Ser Ser Thr Ser Glu
        435                 440                 445

ggg tat aca gca tct caa ccc ttg tac cag cct tct cat gct aca gag     1392
Gly Tyr Thr Ala Ser Gln Pro Leu Tyr Gln Pro Ser His Ala Thr Glu
    450                 455                 460

caa cga cca caa aag gaa cca att gac cag att cag gca aca atc tct     1440
Gln Arg Pro Gln Lys Glu Pro Ile Asp Gln Ile Gln Ala Thr Ile Ser
465                 470                 475                 480

tta aat aca gac cag act aca gcg tca tca tcc ctt ccg gct gct tct     1488
Leu Asn Thr Asp Gln Thr Thr Ala Ser Ser Ser Leu Pro Ala Ala Ser
                485                 490                 495

cag cct cag gta ttc cag gct ggg aca agc aaa cca tta cat agc agt     1536
Gln Pro Gln Val Phe Gln Ala Gly Thr Ser Lys Pro Leu His Ser Ser
            500                 505                 510

gga atc aat gta aat gca gct cca ttc caa tcc atg caa acg gtg ttc     1584
Gly Ile Asn Val Asn Ala Ala Pro Phe Gln Ser Met Gln Thr Val Phe
        515                 520                 525

aat atg aat gcc cca gtt cct cct gtt aat gaa cca gaa act ttg aaa     1632
Asn Met Asn Ala Pro Val Pro Pro Val Asn Glu Pro Glu Thr Leu Lys
    530                 535                 540
```

```
caa caa aat cag tac cag gcc agt tat aac cag agc ttt tct agt cag      1680
Gln Gln Asn Gln Tyr Gln Ala Ser Tyr Asn Gln Ser Phe Ser Ser Gln
545                 550                 555                 560

cct cac caa gta gaa caa aca gac ctt cag caa gaa cag ctt caa aca      1728
Pro His Gln Val Glu Gln Thr Asp Leu Gln Gln Glu Gln Leu Gln Thr
                565                 570                 575

gtg gtt ggc act tac cat ggt tcc cag gac cag ccc cac caa gtg act      1776
Val Val Gly Thr Tyr His Gly Ser Gln Asp Gln Pro His Gln Val Thr
            580                 585                 590

ggt aac cat cag cag cct ccc cag cag aac act gga ttt cca cgt agc      1824
Gly Asn His Gln Gln Pro Pro Gln Gln Asn Thr Gly Phe Pro Arg Ser
        595                 600                 605

agt cag ccc tat tac aat agt cgt ggt gtg tct cgt ggt ggt tcc cgt      1872
Ser Gln Pro Tyr Tyr Asn Ser Arg Gly Val Ser Arg Gly Gly Ser Arg
    610                 615                 620

ggt gct aga ggc tta atg aat gga tac agg ggc cct gcc aat gga ttc      1920
Gly Ala Arg Gly Leu Met Asn Gly Tyr Arg Gly Pro Ala Asn Gly Phe
625                 630                 635                 640

aga gga gga tat gat ggt tac cgc cct tca ttc tct aac act cca aac      1968
Arg Gly Gly Tyr Asp Gly Tyr Arg Pro Ser Phe Ser Asn Thr Pro Asn
                645                 650                 655

agt ggt tat aca cag tct cag ttc agt gct ccc cgg gac tac tct ggc      2016
Ser Gly Tyr Thr Gln Ser Gln Phe Ser Ala Pro Arg Asp Tyr Ser Gly
            660                 665                 670

tat cag cgg gga tgc cgc aaa tga acactcagca agtgaattaa tctgattcac     2070
Tyr Gln Arg Gly Cys Arg Lys
        675

aggattatgt ttaaacgcca aaaacacact ggccagtgta ccataatatg ttaccagaag   2130

agttattatc tatttgttct ccctttcagg aaacttattg taaagggact gttttcatcc   2190

cataaagaca ggactacaat tgtcagcttt atattacctg gatatggaag gaaactattt   2250

ttattctgca tgttcttcct aagcgtcatc ttgagccttg cacatgatac tcagattcct   2310

cacccttgct taggagtaaa acataataca ctttacaggg tgatatctcc atagttattt   2370

gaagtggctt ggaaaaagca agattaactt ctgacattgg ataaaaatca acaaatcagc   2430

cctagagtta ttcaaatggt aattgacaaa aactaaaata tttcccttcg agaaggagtg   2490

gaatgtggtt tggcagaaca actgcatttc acagcttttc cggttaaatt ggagcactaa   2550

acgtttagat gcataccaaa ttatgcatgg gcccttaata taaaaggctg gctaccagct   2610

ttgacacagc actattcatc ctctggccaa acaactgtgg ttaaacaaca catgtaaatt   2670

gctttttaac agctgatact ataataagac aaagccaaaa tgcaaaaatt gggctttgat   2730

tggcactttt tgaaaaatat gcaacaaata tgggatgtaa tctggatggc cgcttctgta   2790

cttaatgtga agtatttaga taccttttg aacacttaac agtttcttct gacaatgact    2850

tttgtaagga ttggtactat ctatcattcc ttataatgta cattgtctgt cactaatcct   2910

cagatcttgc tgtattgtca cctaaattgg tacaggtact gatgaaaata tctaatggat   2970

aatcataaca ctcttggtca catgtttttc ctgcagcctg aaggttttta aaagaaaaag   3030

atatcaaatg cctgctgcta ccaccctttt aaattgctat cttttgaaaa gcaccagtat   3090

gtgttttaga ttgatttccc tattttaggg aaatgacaga cagtagtttc agttctgatg   3150

gtataagcaa aacaaataaa acatgtttat aaaagttgta tcttgaaaca ctggtgttca   3210

acagctagca gcttatgtgg ttcaccccat gcattgttag tgtttcagat tttatggtta   3270

tctccagcag ctgtttctgt agtacttgca tttatc                               3306
```

<210> SEQ ID NO 12

<211> LENGTH: 679
<212> TYPE: PRT
<213> ORGANISM: Canis familiaris

<400> SEQUENCE: 12

```
Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Glu Ala Ala Ser
            260                 265                 270

Ala Pro Thr Val Glu Asp Gln Val Ala Glu Ala Glu Pro Glu Pro Ala
        275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
        355                 360                 365

Asp Leu Met Ala Gln Met Gln Gly Pro Tyr Asn Phe Ile Gln Asp Ser
    370                 375                 380

Met Leu Asp Phe Glu Asn Gln Thr Leu Asp Pro Ala Ile Val Ser Ala
385                 390                 395                 400
```

```
Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
            420                 425                 430

Val Gln Pro Glu Ala Thr Gln Val Pro Leu Val Ser Ser Thr Ser Glu
        435                 440                 445

Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
    530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Gly Cys Arg Lys
        675


<210> SEQ ID NO 13
<211> LENGTH: 2281
<212> TYPE: DNA
<213> ORGANISM: Canis familiaris
<220> FEATURE:
<221> NAME/KEY: CDS
<222> LOCATION: (1)..(2154)
<223> OTHER INFORMATION:

<400> SEQUENCE: 13

atg ccg tcg gcc acc agc ctc agc gga agc ggc agc aag tcg tcg ggc      48
Met Pro Ser Ala Thr Ser Leu Ser Gly Ser Gly Ser Lys Ser Ser Gly
1               5                   10                  15

ccg ccg ccc ccg tcg ggt tcc tcc ggg agc gag gcg gcg gcg gcg gcg      96
Pro Pro Pro Pro Ser Gly Ser Ser Gly Ser Glu Ala Ala Ala Ala Ala
            20                  25                  30

ggg gcg gcg ggg gcg gcg ggg gcc ggg gcg gct gcg ccc gcc tcc cag     144
Gly Ala Ala Gly Ala Ala Gly Ala Gly Ala Ala Ala Pro Ala Ser Gln
        35                  40                  45

cac ccc gcg acc ggc acc ggc gct gtc cag acc gag gcc atg aag cag     192
```

```
His Pro Ala Thr Gly Thr Gly Ala Val Gln Thr Glu Ala Met Lys Gln
    50                  55                  60

atc ctc ggg gtg atc gac aag aaa ctc cgg aac ctg gag aag aaa aag      240
Ile Leu Gly Val Ile Asp Lys Lys Leu Arg Asn Leu Glu Lys Lys Lys
65                  70                  75                  80

ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
                85                  90                  95

aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110

aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125

caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140

atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160

cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175

aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190

ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205

ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220

ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240

cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255

act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270

gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285

gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300

aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320

gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335

cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350

act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365

gac ctt atg gcg cag atg cag ggg ccc tat aat ttc ata cag gat tca     1152
```

```
Asp Leu Met Ala Gln Met Gln Gly Pro Tyr Asn Phe Ile Gln Asp Ser
    370                 375                 380

atg ctg gat ttt gaa aac cag aca ctc gat cct gcc att gta tct gca      1200
Met Leu Asp Phe Glu Asn Gln Thr Leu Asp Pro Ala Ile Val Ser Ala
385                 390                 395                 400

cag cct atg aat ccg aca caa aac atg gac atg ccc cag ctg gtt tgc      1248
Gln Pro Met Asn Pro Thr Gln Asn Met Asp Met Pro Gln Leu Val Cys
                405                 410                 415

cct cca gtt cat tct gaa tct aga ctt gct caa cct aat caa gtt cct      1296
Pro Pro Val His Ser Glu Ser Arg Leu Ala Gln Pro Asn Gln Val Pro
            420                 425                 430

gta caa cca gaa gct aca cag gtt cct ttg gtt tca tcc aca agt gag      1344
Val Gln Pro Glu Ala Thr Gln Val Pro Leu Val Ser Ser Thr Ser Glu
        435                 440                 445

ggg tat aca gca tct caa ccc ttg tac cag cct tct cat gct aca gag      1392
Gly Tyr Thr Ala Ser Gln Pro Leu Tyr Gln Pro Ser His Ala Thr Glu
    450                 455                 460

caa cga cca caa aag gaa cca att gac cag att cag gca aca atc tct      1440
Gln Arg Pro Gln Lys Glu Pro Ile Asp Gln Ile Gln Ala Thr Ile Ser
465                 470                 475                 480

tta aat aca gac cag act aca gcg tca tca tcc ctt ccg gct gct tct      1488
Leu Asn Thr Asp Gln Thr Thr Ala Ser Ser Ser Leu Pro Ala Ala Ser
                485                 490                 495

cag cct cag gta ttc cag gct ggg aca agc aaa cca tta cat agc agt      1536
Gln Pro Gln Val Phe Gln Ala Gly Thr Ser Lys Pro Leu His Ser Ser
            500                 505                 510

gga atc aat gta aat gca gct cca ttc caa tcc atg caa acg gtg ttc      1584
Gly Ile Asn Val Asn Ala Ala Pro Phe Gln Ser Met Gln Thr Val Phe
        515                 520                 525

aat atg aat gcc cca gtt cct cct gtt aat gaa cca gaa act ttg aaa      1632
Asn Met Asn Ala Pro Val Pro Pro Val Asn Glu Pro Glu Thr Leu Lys
    530                 535                 540

caa caa aat cag tac cag gcc agt tat aac cag agc ttt tct agt cag      1680
Gln Gln Asn Gln Tyr Gln Ala Ser Tyr Asn Gln Ser Phe Ser Ser Gln
545                 550                 555                 560

cct cac caa gta gaa caa aca gac ctt cag caa gaa cag ctt caa aca      1728
Pro His Gln Val Glu Gln Thr Asp Leu Gln Gln Glu Gln Leu Gln Thr
                565                 570                 575

gtg gtt ggc act tac cat ggt tcc cag gac cag ccc cac caa gtg act      1776
Val Val Gly Thr Tyr His Gly Ser Gln Asp Gln Pro His Gln Val Thr
            580                 585                 590

ggt aac cat cag cag cct ccc cag cag aac act gga ttt cca cgt agc      1824
Gly Asn His Gln Gln Pro Pro Gln Gln Asn Thr Gly Phe Pro Arg Ser
        595                 600                 605

agt cag ccc tat tac aat agt cgt ggt gtg tct cgt ggt ggt tcc cgt      1872
Ser Gln Pro Tyr Tyr Asn Ser Arg Gly Val Ser Arg Gly Gly Ser Arg
    610                 615                 620

ggt gct aga ggc tta atg aat gga tac agg ggc cct gcc aat gga ttc      1920
Gly Ala Arg Gly Leu Met Asn Gly Tyr Arg Gly Pro Ala Asn Gly Phe
625                 630                 635                 640

aga gga gga tat gat ggt tac cgc cct tca ttc tct aac act cca aac      1968
Arg Gly Gly Tyr Asp Gly Tyr Arg Pro Ser Phe Ser Asn Thr Pro Asn
                645                 650                 655

agt ggt tat aca cag tct cag ttc agt gct ccc cgg gac tac tct ggc      2016
Ser Gly Tyr Thr Gln Ser Gln Phe Ser Ala Pro Arg Asp Tyr Ser Gly
            660                 665                 670

tat cag cgg gat gga tat cag cag aat ttc aag cga ggc tct ggg cag      2064
Tyr Gln Arg Asp Gly Tyr Gln Gln Asn Phe Lys Arg Gly Ser Gly Gln
        675                 680                 685

agt gga cca cgg gga gcc cca cga ggt cgt gga ggg ccc cca aga ccc      2112
```

```
Ser Gly Pro Arg Gly Ala Pro Arg Gly Arg Gly Gly Pro Pro Arg Pro
    690                 695                 700

aac aga ggg atg ccg caa atg aac act cag caa gtg aat taa            2154
Asn Arg Gly Met Pro Gln Met Asn Thr Gln Gln Val Asn
705                 710                 715

tctgattcac aggattatgt ttaaacgcca aaaacacact ggccagtgta ccataatatg   2214

ttaccagaag agttattatc tatttggact gttttcatcc cataaagaca ggactacaat   2274

tgtcagc                                                             2281


<210> SEQ ID NO 14
<211> LENGTH: 717
<212> TYPE: PRT
<213> ORGANISM: Canis familiaris

<400> SEQUENCE: 14

Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Glu Ala Ala Ser
            260                 265                 270

Ala Pro Thr Val Glu Asp Gln Val Ala Glu Ala Glu Pro Glu Pro Ala
        275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320
```

```
Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
        355                 360                 365

Asp Leu Met Ala Gln Met Gln Gly Pro Tyr Asn Phe Ile Gln Asp Ser
    370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
            420                 425                 430

Val Gln Pro Glu Ala Thr Gln Val Pro Leu Val Ser Ser Thr Ser Glu
        435                 440                 445

Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
    530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Asp Gly Tyr Gln Gln Asn Phe Lys Arg Gly Ser Gly Gln
        675                 680                 685

Ser Gly Pro Arg Gly Ala Pro Arg Gly Arg Gly Gly Pro Pro Arg Pro
    690                 695                 700

Asn Arg Gly Met Pro Gln Met Asn Thr Gln Gln Val Asn
705                 710                 715
```

<210> SEQ ID NO 15
<211> LENGTH: 3386
<212> TYPE: DNA

```
<213> ORGANISM: Bos taurus
<220> FEATURE:
<221> NAME/KEY: CDS
<222> LOCATION: (82)..(2208)
<223> OTHER INFORMATION:

<400> SEQUENCE: 15

cgcgtctcgc cccgtccacc gattgactcg ccgctcttgt ccttcctccc gctctttctt      60

ctctcccctt acggtttcaa g atg cct tcg gcc acc agc cac agc gga agc      111
                        Met Pro Ser Ala Thr Ser His Ser Gly Ser
                        1               5                   10

ggc agc aag tcg tcc gga ccg cca ccg ccg tcg ggt tcc tcc ggg aat      159
Gly Ser Lys Ser Ser Gly Pro Pro Pro Pro Ser Gly Ser Ser Gly Asn
                15                  20                  25

gag gcg ggg gcc ggg gcc gcc gcg ccg gct tcc caa cac ccc atg acc      207
Glu Ala Gly Ala Gly Ala Ala Ala Pro Ala Ser Gln His Pro Met Thr
            30                  35                  40

ggc acc ggg gct gtc cag acc gag gcc atg aag cag att ctc ggg gtg      255
Gly Thr Gly Ala Val Gln Thr Glu Ala Met Lys Gln Ile Leu Gly Val
        45                  50                  55

atc gac aag aaa ctt cgg aac ctg gag aag aaa aag ggc aag ctt gat      303
Ile Asp Lys Lys Leu Arg Asn Leu Glu Lys Lys Lys Gly Lys Leu Asp
    60                  65                  70

gat tat cag gaa cga atg aac aaa ggg gaa agg ctt aat caa gat cag      351
Asp Tyr Gln Glu Arg Met Asn Lys Gly Glu Arg Leu Asn Gln Asp Gln
75                  80                  85                  90

ctg gat gcc gtg tct aag tac cag gaa gtc aca aat aac ttg gag ttt      399
Leu Asp Ala Val Ser Lys Tyr Gln Glu Val Thr Asn Asn Leu Glu Phe
                95                  100                 105

gca aaa gaa tta cag agg agt ttc atg gca tta agc caa gat att cag      447
Ala Lys Glu Leu Gln Arg Ser Phe Met Ala Leu Ser Gln Asp Ile Gln
            110                 115                 120

aaa aca ata aag aag aca gca cgt cgg gag cag ctt atg aga gag gaa      495
Lys Thr Ile Lys Lys Thr Ala Arg Arg Glu Gln Leu Met Arg Glu Glu
        125                 130                 135

gct gaa cag aaa cgt tta aaa aca gta ctt gag ctg cag tat gtt ttg      543
Ala Glu Gln Lys Arg Leu Lys Thr Val Leu Glu Leu Gln Tyr Val Leu
    140                 145                 150

gac aaa cta gga gat gat gaa gtg aga act gac ctg aag caa ggt ttg      591
Asp Lys Leu Gly Asp Asp Glu Val Arg Thr Asp Leu Lys Gln Gly Leu
155                 160                 165                 170

aat gga gtg cca ata ttg tct gaa gag gag ttg tcg ttg tta gat gag      639
Asn Gly Val Pro Ile Leu Ser Glu Glu Glu Leu Ser Leu Leu Asp Glu
                175                 180                 185

ttc tac aaa tta gca gac cct gaa cga gac atg agc ttg agg ttg aat      687
Phe Tyr Lys Leu Ala Asp Pro Glu Arg Asp Met Ser Leu Arg Leu Asn
            190                 195                 200

gag cag tat gaa cat gcc tcc att cac ctg tgg gac ttg ctg gaa gga      735
Glu Gln Tyr Glu His Ala Ser Ile His Leu Trp Asp Leu Leu Glu Gly
        205                 210                 215

aag gaa aaa cct gta tgt gga aca act tat aaa gct cta aag gaa att      783
Lys Glu Lys Pro Val Cys Gly Thr Thr Tyr Lys Ala Leu Lys Glu Ile
    220                 225                 230

gtt gag cgt gtt ttc cag tca aac tac ttt gac agc acc cac aac cac      831
Val Glu Arg Val Phe Gln Ser Asn Tyr Phe Asp Ser Thr His Asn His
235                 240                 245                 250

cag aat ggt ctg tgt gag gaa gag gag gca gcc tca gca cct aca gtt      879
Gln Asn Gly Leu Cys Glu Glu Glu Glu Ala Ala Ser Ala Pro Thr Val
                255                 260                 265

gaa gac cag gca gct gaa gct gaa cct gag cca gtg gaa gaa tat act      927
Glu Asp Gln Ala Ala Glu Ala Glu Pro Glu Pro Val Glu Glu Tyr Thr
```

```
            270                 275                 280

gaa caa aat gag gtt gaa tca aca gag tat gta aat aga caa ttt atg      975
Glu Gln Asn Glu Val Glu Ser Thr Glu Tyr Val Asn Arg Gln Phe Met
        285                 290                 295

gca gaa aca cag ttc agc agt ggt gaa aag gag cag gta gat gat tgg     1023
Ala Glu Thr Gln Phe Ser Ser Gly Glu Lys Glu Gln Val Asp Asp Trp
    300                 305                 310

aca gtt gaa aca gtt gag gtg gta aat tca ctc cag cag caa cct cag     1071
Thr Val Glu Thr Val Glu Val Val Asn Ser Leu Gln Gln Gln Pro Gln
315                 320                 325                 330

gct gca tct cct tca gta cca gaa ccc cac tct ttg acc cca gtg gct     1119
Ala Ala Ser Pro Ser Val Pro Glu Pro His Ser Leu Thr Pro Val Ala
                335                 340                 345

caa gcc gat ccc ctc gtg aga aga cag cga gta cag gac ctt atg gca     1167
Gln Ala Asp Pro Leu Val Arg Arg Gln Arg Val Gln Asp Leu Met Ala
            350                 355                 360

caa atg cag ggg ccc tat aat ttc ata cag gat tca atg ttg gat ttt     1215
Gln Met Gln Gly Pro Tyr Asn Phe Ile Gln Asp Ser Met Leu Asp Phe
        365                 370                 375

gaa aac cag aca ctt gat cct gcc att gta tct gca cag ccg atg aat     1263
Glu Asn Gln Thr Leu Asp Pro Ala Ile Val Ser Ala Gln Pro Met Asn
    380                 385                 390

cca gca cag aac atg gac ata ccc cag ctg gtt tgc cct cca gtt cat     1311
Pro Ala Gln Asn Met Asp Ile Pro Gln Leu Val Cys Pro Pro Val His
395                 400                 405                 410

tct gaa tct aga ctt gct caa cct aat caa gtt tct gta cag cca gaa     1359
Ser Glu Ser Arg Leu Ala Gln Pro Asn Gln Val Ser Val Gln Pro Glu
                415                 420                 425

gct aca cag gtt cct ttg gtt tca tcc aca agt gag gga tat aca gca     1407
Ala Thr Gln Val Pro Leu Val Ser Ser Thr Ser Glu Gly Tyr Thr Ala
            430                 435                 440

tct caa ccc ttg tac caa cct tct cat gct act gac caa cga cca caa     1455
Ser Gln Pro Leu Tyr Gln Pro Ser His Ala Thr Asp Gln Arg Pro Gln
        445                 450                 455

aag gaa ccg att gat cag att cag gcg acg atc tct tta aat aca gac     1503
Lys Glu Pro Ile Asp Gln Ile Gln Ala Thr Ile Ser Leu Asn Thr Asp
    460                 465                 470

cag act aca gca tca tca tcc ctt cct gct gct tct cag cct caa gtg     1551
Gln Thr Thr Ala Ser Ser Ser Leu Pro Ala Ala Ser Gln Pro Gln Val
475                 480                 485                 490

ttc cag gct ggg aca agc aaa cct tta cat agc agt gga atc aat gta     1599
Phe Gln Ala Gly Thr Ser Lys Pro Leu His Ser Ser Gly Ile Asn Val
                495                 500                 505

aat gca gct cca ttc caa tcc atg caa acg gta ttc aat atg aat gcc     1647
Asn Ala Ala Pro Phe Gln Ser Met Gln Thr Val Phe Asn Met Asn Ala
            510                 515                 520

cca gtt cct cct gtt aat gaa cca gaa act tta aaa cag caa aat cag     1695
Pro Val Pro Pro Val Asn Glu Pro Glu Thr Leu Lys Gln Gln Asn Gln
        525                 530                 535

tac cag gcc agt tac aac cag agc ttt tcc agt cag cct cac caa gta     1743
Tyr Gln Ala Ser Tyr Asn Gln Ser Phe Ser Ser Gln Pro His Gln Val
    540                 545                 550

gaa caa aca gag ctt cag caa gaa cag ctt caa aca gtg gtt ggc act     1791
Glu Gln Thr Glu Leu Gln Gln Glu Gln Leu Gln Thr Val Val Gly Thr
555                 560                 565                 570

tat cat ggt tct cag gac cag ccc cat caa gtg act ggt aac cac cag     1839
Tyr His Gly Ser Gln Asp Gln Pro His Gln Val Thr Gly Asn His Gln
                575                 580                 585

cag cct cct cag cag aac act gga ttt cca cgt agc aat cag ccc tat     1887
Gln Pro Pro Gln Gln Asn Thr Gly Phe Pro Arg Ser Asn Gln Pro Tyr
```

```
            590                 595                 600

tac aac agt cgt ggt gtg tct cgt gga ggt tcc cgt ggt gct aga ggc     1935
Tyr Asn Ser Arg Gly Val Ser Arg Gly Gly Ser Arg Gly Ala Arg Gly
        605                 610                 615

ttg atg aat gga tac aga gga cct gct aat gga ttc aga gga gga tat     1983
Leu Met Asn Gly Tyr Arg Gly Pro Ala Asn Gly Phe Arg Gly Gly Tyr
    620                 625                 630

gat ggt tac cgc cct tca ttc tct act aac act cca aac agt ggt tat     2031
Asp Gly Tyr Arg Pro Ser Phe Ser Thr Asn Thr Pro Asn Ser Gly Tyr
635                 640                 645                 650

aca caa tct caa ttc agt gct ccc cgg gac tac tct ggc tat cag cgg     2079
Thr Gln Ser Gln Phe Ser Ala Pro Arg Asp Tyr Ser Gly Tyr Gln Arg
                655                 660                 665

gat gga tat cag cag aat ttc aag cga ggc tct ggg cag agt gga cca     2127
Asp Gly Tyr Gln Gln Asn Phe Lys Arg Gly Ser Gly Gln Ser Gly Pro
            670                 675                 680

cgg gga gcc cca cga ggt cgt gga ggg ccc cca aga ccc aac aga ggg     2175
Arg Gly Ala Pro Arg Gly Arg Gly Gly Pro Pro Arg Pro Asn Arg Gly
        685                 690                 695

atg ccg caa atg aac act cag caa gtg aat taa tctgattcac aggattatgt   2228
Met Pro Gln Met Asn Thr Gln Gln Val Asn
    700                 705

ttaatcgcca aaaacacact ggccagtgta ccataatatg ttaccagaag agttattatc   2288

tatttgttct ccctttcagg aaacttattg taaagggact gttttcatcc cataaagaca   2348

ggactacaat tgtcagcttt atattacctg gatatggaag gaaactattt ttactctgca   2408

tgttctgtcc taagcgtcat cttgagcctt gcacatgata ctcagattcc tcacccttgc   2468

ttaggagtaa aacataatat actttaatgg ggtgatatct ccatagttat ttgaagtggc   2528

ttggataaag caagactgac ttctgacatt ggataaaatc tacaaatcag ccctagagtc   2588

attcagtggt aactgacaaa actaaaatat ttcccttgaa aggaagatgg aaggagtgga   2648

gtgtggtttg gcagaacaac tgcatttcac agcttttcca cttaaattgg agcactgaac   2708

atttagatgc ataccgaatt atgcatgggc cctaatcaca cagacaaggc tggtgccagc   2768

cttaggcttg acacggcagt gttcaccctc tggccagacg actgtggttc aagacacatg   2828

taaattgctt tttaacagct gatactgtat aagacaaagc caaaatgcaa aattaggctt   2888

tgattggcac ttttcgaaaa atatgcaaca attaagggat ataatctgga tggccgcttc   2948

tgtacttaat gtgaaatatt tagatacctt tcaaacactt aacagtttct ttgacaatga   3008

gttttgtaag gattggtagt aaatatcatt ccttatgacg tacattgtct gtcactaatc   3068

cttggatctt gctgtattgt cacctaaatt ggtacaggta ctgatgaaaa tctaatggat   3128

aatcataaca ctcttggtta catgtttttc ctgcagcctg aaagttttta taagaaaaag   3188

acatcaaatg cctgctgctg ccaccctttt aaattgctat cttttgaaaa gcaccagtat   3248

gtgttttaga ttgatttccc tattttaggg aaatgacagt cagtagtttc acttctgatg   3308

gtataagcaa acaaataaaa catgtttata aaaaaaaaaa aaaaaaaaaa aaaaaaaaaa   3368

aaaaaaaaaa aaaaaaaa                                                  3386


<210> SEQ ID NO 16
<211> LENGTH: 708
<212> TYPE: PRT
<213> ORGANISM: Bos taurus

<400> SEQUENCE: 16

Met Pro Ser Ala Thr Ser His Ser Gly Ser Gly Ser Lys Ser Ser Gly
1               5                   10                  15
```

```
Pro Pro Pro Pro Ser Gly Ser Ser Gly Asn Glu Ala Gly Ala Gly Ala
            20                  25                  30

Ala Ala Pro Ala Ser Gln His Pro Met Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Glu Val Arg Thr Asp Leu Lys Gln Gly Leu Asn Gly Val Pro Ile Leu
                165                 170                 175

Ser Glu Glu Glu Leu Ser Leu Leu Asp Glu Phe Tyr Lys Leu Ala Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Ala Ala Glu
            260                 265                 270

Ala Glu Pro Glu Pro Val Glu Glu Tyr Thr Glu Gln Asn Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Asp Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ala Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Ala Gln Asn Met Asp
385                 390                 395                 400

Ile Pro Gln Leu Val Cys Pro Pro Val His Ser Glu Ser Arg Leu Ala
                405                 410                 415

Gln Pro Asn Gln Val Ser Val Gln Pro Glu Ala Thr Gln Val Pro Leu
            420                 425                 430

Val Ser Ser Thr Ser Glu Gly Tyr Thr Ala Ser Gln Pro Leu Tyr Gln
```

```
        435                 440                 445

Pro Ser His Ala Thr Asp Gln Arg Pro Gln Lys Glu Pro Ile Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Val Asn
        515                 520                 525

Glu Pro Glu Thr Leu Lys Gln Gln Asn Gln Tyr Gln Ala Ser Tyr Asn
    530                 535                 540

Gln Ser Phe Ser Ser Gln Pro His Gln Val Glu Gln Thr Glu Leu Gln
545                 550                 555                 560

Gln Glu Gln Leu Gln Thr Val Val Gly Thr Tyr His Gly Ser Gln Asp
                565                 570                 575

Gln Pro His Gln Val Thr Gly Asn His Gln Gln Pro Pro Gln Gln Asn
            580                 585                 590

Thr Gly Phe Pro Arg Ser Asn Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Thr Asn Thr Pro Asn Ser Gly Tyr Thr Gln Ser Gln Phe Ser
                645                 650                 655

Ala Pro Arg Asp Tyr Ser Gly Tyr Gln Arg Asp Gly Tyr Gln Gln Asn
            660                 665                 670

Phe Lys Arg Gly Ser Gly Gln Ser Gly Pro Arg Gly Ala Pro Arg Gly
        675                 680                 685

Arg Gly Gly Pro Pro Arg Pro Asn Arg Gly Met Pro Gln Met Asn Thr
    690                 695                 700

Gln Gln Val Asn
705


<210> SEQ ID NO 17
<211> LENGTH: 3150
<212> TYPE: DNA
<213> ORGANISM: Equus caballus
<220> FEATURE:
<221> NAME/KEY: CDS
<222> LOCATION: (1)..(1917)
<223> OTHER INFORMATION:

<400> SEQUENCE: 17

atg gag ggc aag ctc gat gat tac caa gag cga atg aac aaa gga gaa       48
Met Glu Gly Lys Leu Asp Asp Tyr Gln Glu Arg Met Asn Lys Gly Glu
1               5                   10                  15

agg ctt aat cag gat cag ctg gat gct gtg tct aag tac cag gaa gtc       96
Arg Leu Asn Gln Asp Gln Leu Asp Ala Val Ser Lys Tyr Gln Glu Val
            20                  25                  30

aca aat aac ttg gag ttt gcg aaa gaa ttg cag agg agt ttc atg gcg      144
Thr Asn Asn Leu Glu Phe Ala Lys Glu Leu Gln Arg Ser Phe Met Ala
        35                  40                  45

ttg agt cag gat att cag aaa aca ata aag aag acg gca cgt cgg gag      192
Leu Ser Gln Asp Ile Gln Lys Thr Ile Lys Lys Thr Ala Arg Arg Glu
    50                  55                  60
```

```
cag ctt atg aga gaa gaa gct gaa cag aaa cgt tta aaa act gta ctt      240
Gln Leu Met Arg Glu Glu Ala Glu Gln Lys Arg Leu Lys Thr Val Leu
65                  70                  75                  80

gag ctg cag tat gtt ttg gac aaa ttg gga gat gaa gaa gtg cga act      288
Glu Leu Gln Tyr Val Leu Asp Lys Leu Gly Asp Glu Glu Val Arg Thr
                85                  90                  95

gac ctg aaa caa ggt ttg aat gga gtg cca ata ctc tct gaa gaa gag      336
Asp Leu Lys Gln Gly Leu Asn Gly Val Pro Ile Leu Ser Glu Glu Glu
            100                 105                 110

ttg tcg ctg ttg gat gag ttc tac aag tta gca gac cct gta cgg gac      384
Leu Ser Leu Leu Asp Glu Phe Tyr Lys Leu Ala Asp Pro Val Arg Asp
        115                 120                 125

atg agc ttg agg ttg aat gag cag tat gag cat gcc tcc att cac ctg      432
Met Ser Leu Arg Leu Asn Glu Gln Tyr Glu His Ala Ser Ile His Leu
    130                 135                 140

tgg gac ttg ctg gaa ggg aag gaa aaa tct gtc tgt gga aca acc tat      480
Trp Asp Leu Leu Glu Gly Lys Glu Lys Ser Val Cys Gly Thr Thr Tyr
145                 150                 155                 160

aaa gct ctg agg gaa att gtt gag cgt gtt ttc cag tcc aac tac ttt      528
Lys Ala Leu Arg Glu Ile Val Glu Arg Val Phe Gln Ser Asn Tyr Phe
                165                 170                 175

gac agc acc cac aac cac cag aat ggg ctc tgt gag gag gaa gag gct      576
Asp Ser Thr His Asn His Gln Asn Gly Leu Cys Glu Glu Glu Glu Ala
            180                 185                 190

acc tca gct cca aca gct gaa gac cag gga gct gaa gct gaa cct gag      624
Thr Ser Ala Pro Thr Ala Glu Asp Gln Gly Ala Glu Ala Glu Pro Glu
        195                 200                 205

cca gca gaa gaa tac act gaa caa agt gaa gtt gaa tca aca gag tat      672
Pro Ala Glu Glu Tyr Thr Glu Gln Ser Glu Val Glu Ser Thr Glu Tyr
    210                 215                 220

gta aat aga cag ttt atg gca gaa gcg cag ttc agt ggt gag aag gag      720
Val Asn Arg Gln Phe Met Ala Glu Ala Gln Phe Ser Gly Glu Lys Glu
225                 230                 235                 240

cag gtg gat gag tgg aca gtc gag acg gtc gag gtg gta aat tca ctc      768
Gln Val Asp Glu Trp Thr Val Glu Thr Val Glu Val Val Asn Ser Leu
                245                 250                 255

cag cag caa cct cag gct gca tct cct tca gta ccg gag ccc cac tct      816
Gln Gln Gln Pro Gln Ala Ala Ser Pro Ser Val Pro Glu Pro His Ser
            260                 265                 270

ttg act cca gtg gct cag gca gat ccc ctt gtg aga aga cag cga gta      864
Leu Thr Pro Val Ala Gln Ala Asp Pro Leu Val Arg Arg Gln Arg Val
        275                 280                 285

cag gac ctt atg gcg caa atg cag ggg ccc tat aat ttc ata cag gat      912
Gln Asp Leu Met Ala Gln Met Gln Gly Pro Tyr Asn Phe Ile Gln Asp
    290                 295                 300

tca atg ctg gat ttt gaa aac cag aca ctt gat cct gcc att gta tct      960
Ser Met Leu Asp Phe Glu Asn Gln Thr Leu Asp Pro Ala Ile Val Ser
305                 310                 315                 320

gca cag cct atg aat cca gca cag aat atg gac atg ccc cag ctg gtt     1008
Ala Gln Pro Met Asn Pro Ala Gln Asn Met Asp Met Pro Gln Leu Val
                325                 330                 335

tgc cct cca gtt cat gct gaa tct aga ctt gct caa cct aat caa gtt     1056
Cys Pro Pro Val His Ala Glu Ser Arg Leu Ala Gln Pro Asn Gln Val
            340                 345                 350

cct gta caa cca gaa gct aca cag gtt cct ttg gtt tca tcc aca agt     1104
Pro Val Gln Pro Glu Ala Thr Gln Val Pro Leu Val Ser Ser Thr Ser
        355                 360                 365

gag ggg tat aca gca tct cag ccc ttg tac cag cct tct cat gct aca     1152
Glu Gly Tyr Thr Ala Ser Gln Pro Leu Tyr Gln Pro Ser His Ala Thr
    370                 375                 380
```

```
gag caa cga ccg caa aag gaa ccg act gac cag atc cag gca aca atc     1200
Glu Gln Arg Pro Gln Lys Glu Pro Thr Asp Gln Ile Gln Ala Thr Ile
385                 390                 395                 400

tct tta aat aca gac cag act aca gca tca tca tcc ctt cct gct gct     1248
Ser Leu Asn Thr Asp Gln Thr Thr Ala Ser Ser Ser Leu Pro Ala Ala
                405                 410                 415

tct cag cct cag gtg ttc cag gct ggg aca agc aaa cct tta cac agc     1296
Ser Gln Pro Gln Val Phe Gln Ala Gly Thr Ser Lys Pro Leu His Ser
            420                 425                 430

agt ggg atc aat gta aat gca gcg cca ttc cag tcc atg caa acg gtg     1344
Ser Gly Ile Asn Val Asn Ala Ala Pro Phe Gln Ser Met Gln Thr Val
        435                 440                 445

ttc aac atg aat gcc ccg gtt cct cct gtt aat gaa cca gaa act tta     1392
Phe Asn Met Asn Ala Pro Val Pro Pro Val Asn Glu Pro Glu Thr Leu
    450                 455                 460

aaa cag caa aat cag tac cag gcc agc tat aac cag agc ttt tcc agt     1440
Lys Gln Gln Asn Gln Tyr Gln Ala Ser Tyr Asn Gln Ser Phe Ser Ser
465                 470                 475                 480

ccg cct cac caa gta gag cag aca gag ctt ccg caa gag cag ctt cag     1488
Pro Pro His Gln Val Glu Gln Thr Glu Leu Pro Gln Glu Gln Leu Gln
                485                 490                 495

acg gtg gtt ggt act tac cat gct tcc caa gac cag ccc cat caa gtg     1536
Thr Val Val Gly Thr Tyr His Ala Ser Gln Asp Gln Pro His Gln Val
            500                 505                 510

acc ggt aac cac cag cag cct ccc cag cag aac act ggg ttt cca cgt     1584
Thr Gly Asn His Gln Gln Pro Pro Gln Gln Asn Thr Gly Phe Pro Arg
        515                 520                 525

agc agt cag ccc tat tac aac agt cgt ggt gtg tct cgt gga ggc tcc     1632
Ser Ser Gln Pro Tyr Tyr Asn Ser Arg Gly Val Ser Arg Gly Gly Ser
    530                 535                 540

cgt ggt gct aga ggc ttg atg aat gga tac agg ggc cct gcc aat gga     1680
Arg Gly Ala Arg Gly Leu Met Asn Gly Tyr Arg Gly Pro Ala Asn Gly
545                 550                 555                 560

ttc aga gga gga tat gat ggt tac cgc cct tcg ttc tct aac act cca     1728
Phe Arg Gly Gly Tyr Asp Gly Tyr Arg Pro Ser Phe Ser Asn Thr Pro
                565                 570                 575

aac agc ggt tac aca cag tct cag ttc agt gct ccc cgg gac tac tct     1776
Asn Ser Gly Tyr Thr Gln Ser Gln Phe Ser Ala Pro Arg Asp Tyr Ser
            580                 585                 590

ggc tat cag cgg gat gga tat cag cag aat ttc aag cga ggc tct ggg     1824
Gly Tyr Gln Arg Asp Gly Tyr Gln Gln Asn Phe Lys Arg Gly Ser Gly
        595                 600                 605

cag agt gga ccc cgg gga gcc cca cga ggt cgt gga ggg ccc cca aga     1872
Gln Ser Gly Pro Arg Gly Ala Pro Arg Gly Arg Gly Gly Pro Pro Arg
    610                 615                 620

ccc aac aga ggg atg ccg caa atg aac act cag caa gtg aat taa         1917
Pro Asn Arg Gly Met Pro Gln Met Asn Thr Gln Gln Val Asn
625                 630                 635

tctgattcac aggattatct ttaatcgcca aaacacactg gccagtgtac cataatatgt   1977

taccagaaga gttattatct atttgttctc cctttcagga aacttattgt aaagggactg   2037

ttttcatccc ataaagacag gactacagtt gtcagcttta tattacctgg atatggaagg   2097

aaactatttt tactctgcat gttctgtcct aagcgtcatc ttgagccttg cacatgatac   2157

tcagattcct ttcccttgct taggagtaaa acataatata ctttatgggg tgataatatc   2217

tccatagtta tttgaagtgg cttggaaaaa gcaagattga cttttgacat tggataaaat   2277

ctacaaatca gccctagagt ttcatggtca ttcacaaaac taaaatattt cccttgaaag   2337

gaagatggaa ggactggagt gtggtttggc agaacaactg catttcacag cttttcctat   2397
```

```
taaattggag cactgaatgt taaatgcata ccaaattatg catgggccct taatcacaca   2457

tacatggcta ccagctttga cacagcacta ttcatcctct ggccaaacga ctgtggttaa   2517

aaacacgtgt aaattgcttt ttaacagctg atactgtaaa agacaaagct aaaatgcaaa   2577

attaggcttt cattggcact tttcgaaaaa tatgcaacaa atttgggatg taatctggat   2637

ggccacttct gtacttaatg tgaagtattt agataccttt ttgaacactt aacagtttct   2697

tcgacaatga cttttgtaag gattggtagt atatatcatt ccttatgaca tacattgtct   2757

gttgctaatc cttggatctt gctgtattgt cacctaaatt ggtacaggta ctgatgaaaa   2817

tctctcatgg ataaacctaa cactcttcgt cacatgtttt tcctgcagcc tgaaggtttt   2877

taaaaggaaa agatatcaaa tgcctgctgc taccaccctt ttaaattgct atcttttgaa   2937

aagcaccagt atgtgttttt agattgattt ccctatttta gggaaatgac agtcagtagt   2997

ttcagttctg atggtataag caaagcaaat aaaacgtgtt tataaaagtt gtatcttgaa   3057

acactggtgt tcaacagcta gcagcttctg tggttcaccc cctgccttgt tagtgttacc   3117

catttatggt tatctccagc agcaatttct cta                                 3150
```

<210> SEQ ID NO 18
<211> LENGTH: 638
<212> TYPE: PRT
<213> ORGANISM: Equus caballus

<400> SEQUENCE: 18

```
Met Glu Gly Lys Leu Asp Asp Tyr Gln Glu Arg Met Asn Lys Gly Glu
1               5                   10                  15

Arg Leu Asn Gln Asp Gln Leu Asp Ala Val Ser Lys Tyr Gln Glu Val
            20                  25                  30

Thr Asn Asn Leu Glu Phe Ala Lys Glu Leu Gln Arg Ser Phe Met Ala
        35                  40                  45

Leu Ser Gln Asp Ile Gln Lys Thr Ile Lys Lys Thr Ala Arg Arg Glu
    50                  55                  60

Gln Leu Met Arg Glu Glu Ala Glu Gln Lys Arg Leu Lys Thr Val Leu
65                  70                  75                  80

Glu Leu Gln Tyr Val Leu Asp Lys Leu Gly Asp Glu Glu Val Arg Thr
                85                  90                  95

Asp Leu Lys Gln Gly Leu Asn Gly Val Pro Ile Leu Ser Glu Glu Glu
            100                 105                 110

Leu Ser Leu Leu Asp Glu Phe Tyr Lys Leu Ala Asp Pro Val Arg Asp
        115                 120                 125

Met Ser Leu Arg Leu Asn Glu Gln Tyr Glu His Ala Ser Ile His Leu
    130                 135                 140

Trp Asp Leu Leu Glu Gly Lys Glu Lys Ser Val Cys Gly Thr Thr Tyr
145                 150                 155                 160

Lys Ala Leu Arg Glu Ile Val Glu Arg Val Phe Gln Ser Asn Tyr Phe
                165                 170                 175

Asp Ser Thr His Asn His Gln Asn Gly Leu Cys Glu Glu Glu Glu Ala
            180                 185                 190

Thr Ser Ala Pro Thr Ala Glu Asp Gln Gly Ala Glu Ala Glu Pro Glu
        195                 200                 205

Pro Ala Glu Glu Tyr Thr Glu Gln Ser Glu Val Glu Ser Thr Glu Tyr
    210                 215                 220

Val Asn Arg Gln Phe Met Ala Glu Ala Gln Phe Ser Gly Glu Lys Glu
225                 230                 235                 240
```

```
Gln Val Asp Glu Trp Thr Val Glu Thr Val Glu Val Val Asn Ser Leu
                245                 250                 255

Gln Gln Gln Pro Gln Ala Ala Ser Pro Ser Val Pro Glu Pro His Ser
            260                 265                 270

Leu Thr Pro Val Ala Gln Ala Asp Pro Leu Val Arg Arg Gln Arg Val
        275                 280                 285

Gln Asp Leu Met Ala Gln Met Gln Gly Pro Tyr Asn Phe Ile Gln Asp
    290                 295                 300

Ser Met Leu Asp Phe Glu Asn Gln Thr Leu Asp Pro Ala Ile Val Ser
305                 310                 315                 320

Ala Gln Pro Met Asn Pro Ala Gln Asn Met Asp Met Pro Gln Leu Val
                325                 330                 335

Cys Pro Pro Val His Ala Glu Ser Arg Leu Ala Gln Pro Asn Gln Val
            340                 345                 350

Pro Val Gln Pro Glu Ala Thr Gln Val Pro Leu Val Ser Ser Thr Ser
        355                 360                 365

Glu Gly Tyr Thr Ala Ser Gln Pro Leu Tyr Gln Pro Ser His Ala Thr
    370                 375                 380

Glu Gln Arg Pro Gln Lys Glu Pro Thr Asp Gln Ile Gln Ala Thr Ile
385                 390                 395                 400

Ser Leu Asn Thr Asp Gln Thr Thr Ala Ser Ser Ser Leu Pro Ala Ala
                405                 410                 415

Ser Gln Pro Gln Val Phe Gln Ala Gly Thr Ser Lys Pro Leu His Ser
            420                 425                 430

Ser Gly Ile Asn Val Asn Ala Ala Pro Phe Gln Ser Met Gln Thr Val
        435                 440                 445

Phe Asn Met Asn Ala Pro Val Pro Pro Val Asn Glu Pro Glu Thr Leu
    450                 455                 460

Lys Gln Gln Asn Gln Tyr Gln Ala Ser Tyr Asn Gln Ser Phe Ser Ser
465                 470                 475                 480

Pro Pro His Gln Val Glu Gln Thr Glu Leu Pro Gln Glu Gln Leu Gln
                485                 490                 495

Thr Val Val Gly Thr Tyr His Ala Ser Gln Asp Gln Pro His Gln Val
            500                 505                 510

Thr Gly Asn His Gln Gln Pro Pro Gln Gln Asn Thr Gly Phe Pro Arg
        515                 520                 525

Ser Ser Gln Pro Tyr Tyr Asn Ser Arg Gly Val Ser Arg Gly Gly Ser
    530                 535                 540

Arg Gly Ala Arg Gly Leu Met Asn Gly Tyr Arg Gly Pro Ala Asn Gly
545                 550                 555                 560

Phe Arg Gly Gly Tyr Asp Gly Tyr Arg Pro Ser Phe Ser Asn Thr Pro
                565                 570                 575

Asn Ser Gly Tyr Thr Gln Ser Gln Phe Ser Ala Pro Arg Asp Tyr Ser
            580                 585                 590

Gly Tyr Gln Arg Asp Gly Tyr Gln Gln Asn Phe Lys Arg Gly Ser Gly
        595                 600                 605

Gln Ser Gly Pro Arg Gly Ala Pro Arg Gly Arg Gly Gly Pro Pro Arg
    610                 615                 620

Pro Asn Arg Gly Met Pro Gln Met Asn Thr Gln Gln Val Asn
625                 630                 635
```

<210> SEQ ID NO 19
<211> LENGTH: 6181
<212> TYPE: DNA
<213> ORGANISM: Mus musculus

```
<220> FEATURE:
<221> NAME/KEY: CDS
<222> LOCATION: (179)..(2302)
<223> OTHER INFORMATION:

<400> SEQUENCE: 19

gctggctggc taagtccctc ccgcgccggc tcttgtccca ctaggagcag ctcagagccg      60

cggggacagg gcgaagcggc ctgcgcccac ggagcgcacg tctctgttct caacgcagca     120

ccacccttgc ccccctcggc tgcccactcc agacgtccag cggctccgcg cgcgcacg       178

atg ccc tcg gcc acc agc cac agc gga agc ggc agc aaa tcg tcg gga       226
Met Pro Ser Ala Thr Ser His Ser Gly Ser Gly Ser Lys Ser Ser Gly
1               5                   10                  15

ccg ccg ccg ccg tcc ggt tcc tcc ggg agt gag gcg gcg gcc ggg gca       274
Pro Pro Pro Pro Ser Gly Ser Ser Gly Ser Glu Ala Ala Ala Gly Ala
            20                  25                  30

gct gcg ccg gct tct cag cat ccg gca acc ggc acc ggc gcc gtc cag       322
Ala Ala Pro Ala Ser Gln His Pro Ala Thr Gly Thr Gly Ala Val Gln
        35                  40                  45

acc gag gcc atg aag cag att ctc ggc gta atc gac aag aaa ctt cgg       370
Thr Glu Ala Met Lys Gln Ile Leu Gly Val Ile Asp Lys Lys Leu Arg
    50                  55                  60

aac ctg gag aag aaa aag ggt aaa ctt gat gat tac cag gaa cga atg       418
Asn Leu Glu Lys Lys Lys Gly Lys Leu Asp Asp Tyr Gln Glu Arg Met
65                  70                  75                  80

aat aaa ggg gaa agg ctc aat caa gac cag ctg gat gcc gta tct aag       466
Asn Lys Gly Glu Arg Leu Asn Gln Asp Gln Leu Asp Ala Val Ser Lys
                85                  90                  95

tac cag gaa gtc aca aat aat ttg gag ttt gca aag gaa tta cag agg       514
Tyr Gln Glu Val Thr Asn Asn Leu Glu Phe Ala Lys Glu Leu Gln Arg
            100                 105                 110

agt ttc atg gca tta agt caa gat att cag aaa aca ata aag aag aca       562
Ser Phe Met Ala Leu Ser Gln Asp Ile Gln Lys Thr Ile Lys Lys Thr
        115                 120                 125

gca cgt cgg gaa cag ctt atg aga gaa gaa gca gaa cag aag cgc tta       610
Ala Arg Arg Glu Gln Leu Met Arg Glu Glu Ala Glu Gln Lys Arg Leu
    130                 135                 140

aaa act gta ctt gag tta cag tat gta ttg gat aag ctg gga gat gat       658
Lys Thr Val Leu Glu Leu Gln Tyr Val Leu Asp Lys Leu Gly Asp Asp
145                 150                 155                 160

gat gtg aga aca gat ctg aaa caa ggt ttg agt gga gtg cca ata ttg       706
Asp Val Arg Thr Asp Leu Lys Gln Gly Leu Ser Gly Val Pro Ile Leu
                165                 170                 175

tct gag gag gag ttg tca ttg ctg gat gag ttc tac aag ctc gta gat       754
Ser Glu Glu Glu Leu Ser Leu Leu Asp Glu Phe Tyr Lys Leu Val Asp
            180                 185                 190

cct gag cgt gac atg agt tta agg tta aat gag cag tat gaa cat gcc       802
Pro Glu Arg Asp Met Ser Leu Arg Leu Asn Glu Gln Tyr Glu His Ala
        195                 200                 205

tca att cac ttg tgg gat ttg ctg gaa ggg aaa gaa aag cct gtg tgt       850
Ser Ile His Leu Trp Asp Leu Leu Glu Gly Lys Glu Lys Pro Val Cys
    210                 215                 220

gga aca acc tat aaa gct cta aag gaa att gtt gag cgt gtt ttc cag       898
Gly Thr Thr Tyr Lys Ala Leu Lys Glu Ile Val Glu Arg Val Phe Gln
225                 230                 235                 240

tca aac tac ttt gat agc act cac aat cat caa aat ggg ttg tgt gag       946
Ser Asn Tyr Phe Asp Ser Thr His Asn His Gln Asn Gly Leu Cys Glu
                245                 250                 255

gag gaa gag gcg gct tca gcg ccc aca gtg gag gac cag gta gct gaa       994
Glu Glu Glu Ala Ala Ser Ala Pro Thr Val Glu Asp Gln Val Ala Glu
            260                 265                 270
```

-continued

```
gct gaa cct gag cca gcg gaa gaa tac aca gag caa agt gag gtt gaa      1042
Ala Glu Pro Glu Pro Ala Glu Glu Tyr Thr Glu Gln Ser Glu Val Glu
        275                 280                 285

tca aca gag tat gtc aat agg cag ttc atg gca gaa aca cag ttc agc      1090
Ser Thr Glu Tyr Val Asn Arg Gln Phe Met Ala Glu Thr Gln Phe Ser
    290                 295                 300

agt ggt gag aag gag caa gtg gat gag tgg aca gtt gaa aca gtt gag      1138
Ser Gly Glu Lys Glu Gln Val Asp Glu Trp Thr Val Glu Thr Val Glu
305                 310                 315                 320

gtt gta aac tca ctc cag cag caa cct cag gct gcg tcc cct tca gtc      1186
Val Val Asn Ser Leu Gln Gln Gln Pro Gln Ala Ala Ser Pro Ser Val
                325                 330                 335

cca gag ccc cac tct ttg act cca gtg gct cag tca gat cca ctt gtg      1234
Pro Glu Pro His Ser Leu Thr Pro Val Ala Gln Ser Asp Pro Leu Val
            340                 345                 350

aga agg cag cgt gta caa gat ctt atg gca caa atg caa ggg ccc tat      1282
Arg Arg Gln Arg Val Gln Asp Leu Met Ala Gln Met Gln Gly Pro Tyr
        355                 360                 365

aat ttc ata cag gat tca atg ttg gat ttt gaa aat cag acg ctt gat      1330
Asn Phe Ile Gln Asp Ser Met Leu Asp Phe Glu Asn Gln Thr Leu Asp
    370                 375                 380

cct gcc att gta tcc gca cag cct atg aac cct acc cag aac atg gat      1378
Pro Ala Ile Val Ser Ala Gln Pro Met Asn Pro Thr Gln Asn Met Asp
385                 390                 395                 400

atg cct cag ctg gtt tgc cct cag gtt cat tct gaa tct aga ctt gcc      1426
Met Pro Gln Leu Val Cys Pro Gln Val His Ser Glu Ser Arg Leu Ala
                405                 410                 415

caa tct aat caa gtt cct gta caa cca gaa gcc aca cag gtt cct ttg      1474
Gln Ser Asn Gln Val Pro Val Gln Pro Glu Ala Thr Gln Val Pro Leu
            420                 425                 430

gtt tca tcc aca agt gag ggg tat aca gca tct cag ccc ttg tac cag      1522
Val Ser Ser Thr Ser Glu Gly Tyr Thr Ala Ser Gln Pro Leu Tyr Gln
        435                 440                 445

cca tct cat gct acg gag cag cgg ccg cag aaa gag cca atg gat cag      1570
Pro Ser His Ala Thr Glu Gln Arg Pro Gln Lys Glu Pro Met Asp Gln
    450                 455                 460

att cag gca aca ata tct ttg aat aca gac cag act aca gca tcc tca      1618
Ile Gln Ala Thr Ile Ser Leu Asn Thr Asp Gln Thr Thr Ala Ser Ser
465                 470                 475                 480

tcc ctt cct gct gct tct cag cct caa gtg ttc cag gct ggg aca agt      1666
Ser Leu Pro Ala Ala Ser Gln Pro Gln Val Phe Gln Ala Gly Thr Ser
                485                 490                 495

aaa cct ttg cac agc agt gga atc aat gta aat gca gct cca ttc cag      1714
Lys Pro Leu His Ser Ser Gly Ile Asn Val Asn Ala Ala Pro Phe Gln
            500                 505                 510

tcc atg caa acg gtg ttc aat atg aat gct cca gtc cct cct gct aat      1762
Ser Met Gln Thr Val Phe Asn Met Asn Ala Pro Val Pro Pro Ala Asn
        515                 520                 525

gaa cca gaa acg tta aaa caa cag agt cag tac cag gcc act tat aac      1810
Glu Pro Glu Thr Leu Lys Gln Gln Ser Gln Tyr Gln Ala Thr Tyr Asn
    530                 535                 540

cag agt ttt tcc agt cag cct cac caa gtg gaa caa aca gag ctt caa      1858
Gln Ser Phe Ser Ser Gln Pro His Gln Val Glu Gln Thr Glu Leu Gln
545                 550                 555                 560

caa gac caa ctg caa acg gtg gtt ggc act tac cat gga tcc cag gac      1906
Gln Asp Gln Leu Gln Thr Val Val Gly Thr Tyr His Gly Ser Gln Asp
                565                 570                 575

cag cct cat caa gtg cct ggt aac cac cag caa ccc cca cag cag aac      1954
Gln Pro His Gln Val Pro Gly Asn His Gln Gln Pro Pro Gln Gln Asn
            580                 585                 590
```

```
act ggc ttt cca cgt agc agt cag cct tat tac aac agt cgt ggg gta     2002
Thr Gly Phe Pro Arg Ser Ser Gln Pro Tyr Tyr Asn Ser Arg Gly Val
        595                 600                 605

tct cga gga ggg tct cgt ggt gcc aga ggc ttg atg aat gga tac agg     2050
Ser Arg Gly Gly Ser Arg Gly Ala Arg Gly Leu Met Asn Gly Tyr Arg
    610                 615                 620

ggc cct gcc aat gga ttt aga gga gga tat gat ggt tac cgc cct tca     2098
Gly Pro Ala Asn Gly Phe Arg Gly Gly Tyr Asp Gly Tyr Arg Pro Ser
625                 630                 635                 640

ttc tcg aac act cca aac agt ggt tat tca cag tct cag ttc act gct     2146
Phe Ser Asn Thr Pro Asn Ser Gly Tyr Ser Gln Ser Gln Phe Thr Ala
                645                 650                 655

ccc cgg gac tac tct ggt tac cag cgg gat gga tat cag cag aat ttc     2194
Pro Arg Asp Tyr Ser Gly Tyr Gln Arg Asp Gly Tyr Gln Gln Asn Phe
            660                 665                 670

aag cga ggc tct ggg cag agt gga cca cgg gga gcc cca cga ggt cgt     2242
Lys Arg Gly Ser Gly Gln Ser Gly Pro Arg Gly Ala Pro Arg Gly Arg
        675                 680                 685

gga ggg ccc cca aga ccc aac aga ggg atg ccg caa atg aac act cag     2290
Gly Gly Pro Pro Arg Pro Asn Arg Gly Met Pro Gln Met Asn Thr Gln
    690                 695                 700

caa gtg aat taa tgtgatacac aggattatgt ttaatcgcca aaaacacact         2342
Gln Val Asn
705

ggccagtgta ccataatatg ttaccagaag agttattatc tatttgttct ccctttcagg   2402

aaacttattg taaagggact gttttcatcc cataaagaca ggactgcaat tgtcagcttt   2462

acattacctg gatatggaag gaaactattt ttattctgca tgttctgtcc taagcgtcat   2522

cttgagcctt gcacacaata caatactcag attcctcacc cttgcttagg agtaaaacat   2582

tatatactta tggggtgata atatctccat agttagttga agtggcttgg aaaaaaaatg   2642

caagattgaa tttttgacct tggataaaat ctacaatcag ccctagaact attcagtggt   2702

aattgacaaa gttaaagcat ttttctttgaa aggaagatgg aaggagtgga gtgtggttta  2762

gcaaaactgc atttcatagc tttcccatta aattggagca ccgacagatt aaaagcatac   2822

caaattatgc atgggtcctt actcacacaa gtgaggctgg ctaccagcct tgacatagca   2882

ctcactagtc ttctggccaa acgactgtga ttaaaacaca tgtaaattgc tctttagtag   2942

tggatactgt gtaagacaaa gccaaattgc aaatcaggct ttgattggct cttctggaaa   3002

atatgcatca aatatggggg ataatctgga tgggctgctg ctgtgctcaa tgtgaactat   3062

ttagatacct ttggaacact taacagtttc tctgaacaat gacttacatg gggattggtc   3122

ctgtttgtca ttcctcacca taattgcatt gtcatcacta atccttggat cttgctgtat   3182

tgttactcaa attggtaata ggtactgatg gaaatcgcta atggatggat aatcataaca   3242

cttttggtca catgttttct cctgcagcct gaaagttctt aaagaaaaag atatcaaatg   3302

cctgctgcta ccaccctttt aaattgctat ctttagaaaa gcaccggtat gtgttttaga   3362

ttcatttccc tgttttaggg aaatgacagg cagtagtttc agttctgatg gcaaaacaaa   3422

taaaaacatg tttctaaaag ttgtatcttg aaacactggt gttcaacagc tagcagctaa   3482

agtaattcaa cccatgcatt gctagtgtca cagcctttgg ttatgtctag tagctgtttc   3542

tgaagtattt tcatttatct tttgtcaaat ttaaccctgt ttgaattctc tcctttcctc   3602

aaggagacac ttatgttcaa agtgttgatt ctttgcctta ggtgcataga gagtagacag   3662

tttggagatg gaaaggttag cagtgactta gccatatgtt ctgtgttgga atttgtgcta   3722

gcagtttgag cactagctct gcgtgcctat gaactgaatg ctgcttgtcc cattccattt   3782
```

```
tatgtcatgg agaaataatt ccacttggta acacaaaggc taagttaatg ttattttctg   3842
tacagaaatt aaattttact tttagccttt tgtaaacttt tttttttttt ttccaagccg   3902
gtatcagcta ctcaaaacaa ttctcagata ttcatcatta gacaactgga gtttttgctg   3962
gttttgtagc ctactaaaac tgctgaggct gttgaacatt ccacattcaa aagttttgta   4022
gggtggtgga taatggggaa gcttcaatgt ttattttaaa ataaataaaa taagttcttg   4082
acttttctca tgtgtggtta tggtacatca tattggaagg gttatctgtt tacttttgcc   4142
aagactattt tgccagcacc tacacttgtg tgctttaaaa gacaactacc tgggatgtac   4202
cacaaccata tgttaattgt attttattgg gatggataaa atgtttgtgg tttattggat   4262
aatccctaga tggtgtgtta cgtgtgtaga atataatttt atgatagtaa gaaagcaaaa   4322
ttgaagaaaa taagtttagt attgaatttg agttctgaag tgaattcagg gaatgtctca   4382
cgtttcgggc ttctacccaa agtgtagggc agaaggtgta aaagttgttt gtagtttgac   4442
ttgtttattt tttaagttgc ttattccttt caacagcaac atatcattag ctgtcattct   4502
accattgcag ttctagtgag ttttaacgtc tgcattcaag actgttttaa aagcaacctc   4562
actggacaga gaactgctaa agtcttttcc ttaagatctg agtctttgtt actcagtatc   4622
ttctataata tgcaaatgct tgtctagagg cagaagacct tttgtttggt caagtgtgta   4682
ttttaccaga gtacagggaa ctgatggtcc tacatgtctc ttagtgtagt aagactataa   4742
aatcttttgt acatgcacaa ttcacagtat gtttagatac cacgtgtata atgccccccc   4802
ctcccccagg tagcatgcca ttgatgactt tttgcttagg gccattttat taccagggcc   4862
ttaatattcc taaaaagatg attttttttc atcctttctc ctcttttgat cattgtatct   4922
tgatattaaa aacatgacct tccaatgatt gtagtaaatt aacttctata gttcttttgt   4982
ctctatatgt attcatatat atgctattgt atagagactt caaggagaca tggagatgca   5042
tgcttattct caggttcatt cactaaggtg cttggcagac aaccagtttc taagtgcaga   5102
atgtagttaa gcagcttcat atatgtgcca ggcaatttgt tttgttaaat tttcatctac   5162
ttaaggaaat agggtattgt agcttaggct gatcataccc ttcatttcaa ccttaagctc   5222
tcaacctgca tccatccgac ttgagctatt aagtacttta gttttatcga gtataagtta   5282
acagaaaaag taaattaagc tttgccttta ctattttgaa tttatataca ttctggaaaa   5342
acttagaaac tgttgtatat ttcattagat taaattatat gaaaatgtga ttgtttatag   5402
caaagcctgt gagttgcata caccctaagg aaaactcctt aagtgctcct tgaagagaga   5462
agaaacaatt ctgggtctgg tctttttaag aacaaagcta gactactgta tgttagcact   5522
gtacattaat agtctgttgt gaagcttgag cagtttcctg catagccttg atccttcacc   5582
gttggcattg aaaatagcag tatccctgat gtacttaaaa cttaaagtca ggtttttggta  5642
tatttatttg taagtcttaa tttcctctaa atactatatc tctttagcga gacaacctga   5702
aatttattag cacatttggg tatctcttgc ttggcattat ggccagtgtt aactattcag   5762
tggtgaaaaa attacccctc aagacactgg agtgacccca gatgtgtgta gtaagtggca   5822
tggttcaact gtgtggttaa tgataaatat atgacttagt cggtatgatc tggaaagact   5882
tgattgaaag ataattcagc tgacataagg atgagtgagg agtggcaaac tggataaaag   5942
agtcaagaga cctgtattcc agtgactcct gttttgttta agcattagca agatctgtct   6002
ggggaaactg gatagggcag ttttcttcca tgtttagttt ttgtctcaac atttggaagc   6062
tattgaaggt tttaaaatgg tgtgtattgt tttttttgg gggggggtg gccagaatag   6122
tgggtcatct aataaaactg ccatttaaaa gatcaaaaaa aaaaaaaaaa aaaaaaaaa    6181
```

<210> SEQ ID NO 20
<211> LENGTH: 707
<212> TYPE: PRT
<213> ORGANISM: Mus musculus

<400> SEQUENCE: 20

```
Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380
```

```
Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Arg
        675                 680                 685

Gly Gly Pro Pro Arg Pro Asn Arg Gly Met Pro Gln Met Asn Thr Gln
    690                 695                 700

Gln Val Asn
705
```

<210> SEQ ID NO 21
<211> LENGTH: 6141
<212> TYPE: DNA
<213> ORGANISM: Mus musculus
<220> FEATURE:
<221> NAME/KEY: CDS
<222> LOCATION: (139)..(2262)
<223> OTHER INFORMATION:

<400> SEQUENCE: 21

```
cccaccgcgc gcgcgcgtag ccgcctgccc gcccgcccgc tgcgcgtttt gtcccgcgtc      60

tctccccgtc cgtctcctga cttgctggtc ttgtccttcc ctcccgcttt tttcctctcc     120
```

```
tctcttctcg gtctaaag atg ccc tcg gcc acc agc cac agc gga agc ggc      171
                    Met Pro Ser Ala Thr Ser His Ser Gly Ser Gly
                    1               5                   10

agc aaa tcg tcg gga ccg ccg ccg ccg tcc ggt tcc tcc ggg agt gag      219
Ser Lys Ser Ser Gly Pro Pro Pro Pro Ser Gly Ser Ser Gly Ser Glu
            15                  20                  25

gcg gcg gcc ggg gca gct gcg ccg gct tct cag cat ccg gca acc ggc      267
Ala Ala Ala Gly Ala Ala Ala Pro Ala Ser Gln His Pro Ala Thr Gly
        30                  35                  40

acc ggc gcc gtc cag acc gag gcc atg aag cag att ctc ggc gta atc      315
Thr Gly Ala Val Gln Thr Glu Ala Met Lys Gln Ile Leu Gly Val Ile
    45                  50                  55

gac aag aaa ctt cgg aac ctg gag aag aaa aag ggt aaa ctt gat gat      363
Asp Lys Lys Leu Arg Asn Leu Glu Lys Lys Lys Gly Lys Leu Asp Asp
60                  65                  70                  75

tac cag gaa cga atg aat aaa ggg gaa agg ctc aat caa gac cag ctg      411
Tyr Gln Glu Arg Met Asn Lys Gly Glu Arg Leu Asn Gln Asp Gln Leu
                80                  85                  90

gat gcc gta tct aag tac cag gaa gtc aca aat aat ttg gag ttt gca      459
Asp Ala Val Ser Lys Tyr Gln Glu Val Thr Asn Asn Leu Glu Phe Ala
            95                  100                 105

aag gaa tta cag agg agt ttc atg gca tta agt caa gat att cag aaa      507
Lys Glu Leu Gln Arg Ser Phe Met Ala Leu Ser Gln Asp Ile Gln Lys
        110                 115                 120

aca ata aag aag aca gca cgt cgg gaa cag ctt atg aga gaa gaa gca      555
Thr Ile Lys Lys Thr Ala Arg Arg Glu Gln Leu Met Arg Glu Glu Ala
    125                 130                 135

gaa cag aag cgc tta aaa act gta ctt gag tta cag tat gta ttg gat      603
Glu Gln Lys Arg Leu Lys Thr Val Leu Glu Leu Gln Tyr Val Leu Asp
140                 145                 150                 155

aag ctg gga gat gat gat gtg aga aca gat ctg aaa caa ggt ttg agt      651
Lys Leu Gly Asp Asp Asp Val Arg Thr Asp Leu Lys Gln Gly Leu Ser
                160                 165                 170

gga gtg cca ata ttg tct gag gag gag ttg tca ttg ctg gat gag ttc      699
Gly Val Pro Ile Leu Ser Glu Glu Glu Leu Ser Leu Leu Asp Glu Phe
            175                 180                 185

tac aag ctc gta gat cct gag cgt gac atg agt tta agg tta aat gag      747
Tyr Lys Leu Val Asp Pro Glu Arg Asp Met Ser Leu Arg Leu Asn Glu
        190                 195                 200

cag tat gaa cat gcc tca att cac ttg tgg gat ttg ctg gaa ggg aaa      795
Gln Tyr Glu His Ala Ser Ile His Leu Trp Asp Leu Leu Glu Gly Lys
    205                 210                 215

gaa aag cct gtg tgt gga aca acc tat aaa gct cta aag gaa att gtt      843
Glu Lys Pro Val Cys Gly Thr Thr Tyr Lys Ala Leu Lys Glu Ile Val
220                 225                 230                 235

gag cgt gtt ttc cag tca aac tac ttt gat agc act cac aat cat caa      891
Glu Arg Val Phe Gln Ser Asn Tyr Phe Asp Ser Thr His Asn His Gln
                240                 245                 250

aat ggg ttg tgt gag gag gaa gag gcg gct tca gcg ccc aca gtg gag      939
Asn Gly Leu Cys Glu Glu Glu Glu Ala Ala Ser Ala Pro Thr Val Glu
            255                 260                 265

gac cag gta gct gaa gct gaa cct gag cca gcg gaa gaa tac aca gag      987
Asp Gln Val Ala Glu Ala Glu Pro Glu Pro Ala Glu Glu Tyr Thr Glu
        270                 275                 280

caa agt gag gtt gaa tca aca gag tat gtc aat agg cag ttc atg gca     1035
Gln Ser Glu Val Glu Ser Thr Glu Tyr Val Asn Arg Gln Phe Met Ala
    285                 290                 295

gaa aca cag ttc agc agt ggt gag aag gag caa gtg gat gag tgg aca     1083
Glu Thr Gln Phe Ser Ser Gly Glu Lys Glu Gln Val Asp Glu Trp Thr
300                 305                 310                 315
```

-continued

```
gtt gaa aca gtt gag gtt gta aac tca ctc cag cag caa cct cag gct      1131
Val Glu Thr Val Glu Val Val Asn Ser Leu Gln Gln Gln Pro Gln Ala
                320                 325                 330

gcg tcc cct tca gtc cca gag ccc cac tct ttg act cca gtg gct cag      1179
Ala Ser Pro Ser Val Pro Glu Pro His Ser Leu Thr Pro Val Ala Gln
            335                 340                 345

tca gat cca ctt gtg aga agg cag cgt gta caa gat ctt atg gca caa      1227
Ser Asp Pro Leu Val Arg Arg Gln Arg Val Gln Asp Leu Met Ala Gln
        350                 355                 360

atg caa ggg ccc tat aat ttc ata cag gat tca atg ttg gat ttt gaa      1275
Met Gln Gly Pro Tyr Asn Phe Ile Gln Asp Ser Met Leu Asp Phe Glu
    365                 370                 375

aat cag acg ctt gat cct gcc att gta tcc gca cag cct atg aac cct      1323
Asn Gln Thr Leu Asp Pro Ala Ile Val Ser Ala Gln Pro Met Asn Pro
380                 385                 390                 395

acc cag aac atg gat atg cct cag ctg gtt tgc cct cag gtt cat tct      1371
Thr Gln Asn Met Asp Met Pro Gln Leu Val Cys Pro Gln Val His Ser
                400                 405                 410

gaa tct aga ctt gcc caa tct aat caa gtt cct gta caa cca gaa gcc      1419
Glu Ser Arg Leu Ala Gln Ser Asn Gln Val Pro Val Gln Pro Glu Ala
            415                 420                 425

aca cag gtt cct ttg gtt tca tcc aca agt gag ggg tat aca gca tct      1467
Thr Gln Val Pro Leu Val Ser Ser Thr Ser Glu Gly Tyr Thr Ala Ser
        430                 435                 440

cag ccc ttg tac cag cca tct cat gct acg gag cag cgg ccg cag aaa      1515
Gln Pro Leu Tyr Gln Pro Ser His Ala Thr Glu Gln Arg Pro Gln Lys
    445                 450                 455

gag cca atg gat cag att cag gca aca ata tct ttg aat aca gac cag      1563
Glu Pro Met Asp Gln Ile Gln Ala Thr Ile Ser Leu Asn Thr Asp Gln
460                 465                 470                 475

act aca gca tcc tca tcc ctt cct gct gct tct cag cct caa gtg ttc      1611
Thr Thr Ala Ser Ser Ser Leu Pro Ala Ala Ser Gln Pro Gln Val Phe
                480                 485                 490

cag gct ggg aca agt aaa cct ttg cac agc agt gga atc aat gta aat      1659
Gln Ala Gly Thr Ser Lys Pro Leu His Ser Ser Gly Ile Asn Val Asn
            495                 500                 505

gca gct cca ttc cag tcc atg caa acg gtg ttc aat atg aat gct cca      1707
Ala Ala Pro Phe Gln Ser Met Gln Thr Val Phe Asn Met Asn Ala Pro
        510                 515                 520

gtc cct cct gct aat gaa cca gaa acg tta aaa caa cag agt cag tac      1755
Val Pro Pro Ala Asn Glu Pro Glu Thr Leu Lys Gln Gln Ser Gln Tyr
    525                 530                 535

cag gcc act tat aac cag agt ttt tcc agt cag cct cac caa gtg gaa      1803
Gln Ala Thr Tyr Asn Gln Ser Phe Ser Ser Gln Pro His Gln Val Glu
540                 545                 550                 555

caa aca gag ctt caa caa gac caa ctg caa acg gtg gtt ggc act tac      1851
Gln Thr Glu Leu Gln Gln Asp Gln Leu Gln Thr Val Val Gly Thr Tyr
                560                 565                 570

cat gga tcc cag gac cag cct cat caa gtg cct ggt aac cac cag caa      1899
His Gly Ser Gln Asp Gln Pro His Gln Val Pro Gly Asn His Gln Gln
            575                 580                 585

ccc cca cag cag aac act ggc ttt cca cgt agc agt cag cct tat tac      1947
Pro Pro Gln Gln Asn Thr Gly Phe Pro Arg Ser Ser Gln Pro Tyr Tyr
        590                 595                 600

aac agt cgt ggg gta tct cga gga ggg tct cgt ggt gcc aga ggc ttg      1995
Asn Ser Arg Gly Val Ser Arg Gly Gly Ser Arg Gly Ala Arg Gly Leu
    605                 610                 615

atg aat gga tac agg ggc cct gcc aat gga ttt aga gga gga tat gat      2043
Met Asn Gly Tyr Arg Gly Pro Ala Asn Gly Phe Arg Gly Gly Tyr Asp
620                 625                 630                 635
```

```
ggt tac cgc cct tca ttc tcg aac act cca aac agt ggt tat tca cag     2091
Gly Tyr Arg Pro Ser Phe Ser Asn Thr Pro Asn Ser Gly Tyr Ser Gln
                640                 645                 650

tct cag ttc act gct ccc cgg gac tac tct ggt tac cag cgg gat gga     2139
Ser Gln Phe Thr Ala Pro Arg Asp Tyr Ser Gly Tyr Gln Arg Asp Gly
            655                 660                 665

tat cag cag aat ttc aag cga ggc tct ggg cag agt gga cca cgg gga     2187
Tyr Gln Gln Asn Phe Lys Arg Gly Ser Gly Gln Ser Gly Pro Arg Gly
        670                 675                 680

gcc cca cga ggt cgt gga ggg ccc cca aga ccc aac aga ggg atg ccg     2235
Ala Pro Arg Gly Arg Gly Gly Pro Pro Arg Pro Asn Arg Gly Met Pro
    685                 690                 695

caa atg aac act cag caa gtg aat taa tgtgatacac aggattatgt           2282
Gln Met Asn Thr Gln Gln Val Asn
700                 705

ttaatcgcca aaaacacact ggccagtgta ccataatatg ttaccagaag agttattatc   2342

tatttgttct ccctttcagg aaacttattg taaagggact gttttcatcc cataaagaca   2402

ggactgcaat tgtcagcttt acattacctg gatatggaag gaaactattt ttattctgca   2462

tgttctgtcc taagcgtcat cttgagcctt gcacacaata caatactcag attcctcacc   2522

cttgcttagg agtaaaacat tatatactta tggggtgata atatctccat agttagttga   2582

agtggcttgg aaaaaaaatg caagattgaa tttttgacct tggataaaat ctacaatcag   2642

ccctagaact attcagtggt aattgacaaa gttaaagcat tttctttgaa aggaagatgg   2702

aaggagtgga gtgtggttta gcaaaactgc atttcatagc tttcccatta aattggagca   2762

ccgacagatt aaaagcatac caaattatgc atgggtcctt actcacacaa gtgaggctgg   2822

ctaccagcct tgacatagca ctcactagtc ttctggccaa acgactgtga ttaaaacaca   2882

tgtaaattgc tctttagtag tggatactgt gtaagacaaa gccaaattgc aaatcaggct   2942

ttgattggct cttctggaaa atatgcatca aatatggggg ataatctgga tgggctgctg   3002

ctgtgctcaa tgtgaactat ttagatacct ttggaacact taacagtttc tctgaacaat   3062

gacttacatg ggattggtc ctgtttgtca ttcctcacca taattgcatt gtcatcacta    3122

atccttggat cttgctgtat tgttactcaa attggtaata ggtactgatg gaaatcgcta   3182

atggatggat aatcataaca cttttggtca catgttttct cctgcagcct gaaagttctt   3242

aaagaaaaag atatcaaatg cctgctgcta ccaccctttt aaattgctat ctttagaaaa   3302

gcaccggtat gtgttttaga ttcatttccc tgttttaggg aaatgacagg cagtagtttc   3362

agttctgatg gcaaaacaaa taaaaacatg tttctaaaag ttgtatcttg aaacactggt   3422

gttcaacagc tagcagctaa agtaattcaa cccatgcatt gctagtgtca cagcctttgg   3482

ttatgtctag tagctgtttc tgaagtattt tcatttatct tttgtcaaat ttaaccctgt   3542

ttgaattctc tcctttcctc aaggagacac ttatgttcaa agtgttgatt ctttgcctta   3602

ggtgcataga gagtagacag tttggagatg gaaaggttag cagtgactta gccatatgtt   3662

ctgtgttgga atttgtgcta gcagtttgag cactagctct gcgtgcctat gaactgaatg   3722

ctgcttgtcc cattccattt tatgtcatgg agaaataatt ccacttggta acacaaaggc   3782

taagttaatg ttattttctg tacagaaatt aaattttact tttagccttt tgtaaacttt   3842

tttttttttt ttccaagccg gtatcagcta ctcaaaacaa ttctcagata ttcatcatta   3902

gacaactgga gtttttgctg gttttgtagc ctactaaaac tgctgaggct gttgaacatt   3962

ccacattcaa aagttttgta gggtggtgga taatggggaa gcttcaatgt ttattttaaa   4022

ataaataaaa taagttcttg acttttctca tgtgtggtta tggtacatca tattggaagg   4082
```

```
gttatctgtt tacttttgcc aagactattt tgccagcacc tacacttgtg tgctttaaaa   4142

gacaactacc tgggatgtac cacaaccata tgttaattgt attttattgg gatggataaa   4202

atgtttgtgg tttattggat aatccctaga tggtgtgtta cgtgtgtaga atataatttt   4262

atgatagtaa gaaagcaaaa ttgaagaaaa taagtttagt attgaatttg agttctgaag   4322

tgaattcagg gaatgtctca cgtttcgggc ttctacccaa agtgtagggc agaaggtgta   4382

aaagttgttt gtagtttgac ttgtttattt tttaagttgc ttattccttt caacagcaac   4442

atatcattag ctgtcattct accattgcag ttctagtgag ttttaacgtc tgcattcaag   4502

actgttttaa aagcaacctc actggacaga gaactgctaa agtcttttcc ttaagatctg   4562

agtctttgtt actcagtatc ttctataata tgcaaatgct tgtctagagg cagaagacct   4622

tttgtttggt caagtgtgta ttttaccaga gtacagggaa ctgatggtcc tacatgtctc   4682

ttagtgtagt aagactataa aatcttttgt acatgcacaa ttcacagtat gtttagatac   4742

cacgtgtata atgccccccc ctcccccagg tagcatgcca ttgatgactt tttgcttagg   4802

gccattttat taccagggcc ttaatattcc taaaaagatg atttttttttc atcctttctc   4862

ctcttttgat cattgtatct tgatattaaa aacatgacct tccaatgatt gtagtaaatt   4922

aacttctata gttcttttgt ctctatatgt attcatatat atgctattgt atagagactt   4982

caaggagaca tggagatgca tgcttattct caggttcatt cactaaggtg cttggcagac   5042

aaccagtttc taagtgcaga atgtagttaa gcagcttcat atatgtgcca ggcaatttgt   5102

tttgttaaat tttcatctac ttaaggaaat agggtattgt agcttaggct gatcataccc   5162

ttcatttcaa ccttaagctc tcaacctgca tccatccgac ttgagctatt aagtacttta   5222

gttttatcga gtataagtta acagaaaaag taaattaagc tttgccttta ctattttgaa   5282

tttatataca ttctggaaaa acttagaaac tgttgtatat ttcattagat taaattatat   5342

gaaaatgtga ttgtttatag caaagcctgt gagttgcata caccctaagg aaaactcctt   5402

aagtgctcct tgaagagaga agaaacaatt ctgggtctgg tctttttaag aacaaagcta   5462

gactactgta tgttagcact gtacattaat agtctgttgt gaagcttgag cagtttcctg   5522

catagccttg atccttcacc gttggcattg aaaatagcag tatccctgat gtacttaaaa   5582

cttaaagtca ggttttggta tatttatttg taagtcttaa tttcctctaa atactatatc   5642

tctttagcga gacaacctga aatttattag cacatttggg tatctcttgc ttggcattat   5702

ggccagtgtt aactattcag tggtgaaaaa attacccctc aagacactgg agtgacccca   5762

gatgtgtgta gtaagtggca tggttcaact gtgtggttaa tgataaatat atgacttagt   5822

cggtatgatc tggaaagact tgattgaaag ataattcagc tgacataagg atgagtgagg   5882

agtggcaaac tggataaaag agtcaagaga cctgtattcc agtgactcct gttttgttta   5942

agcattagca agatctgtct ggggaaactg gatagggcag ttttcttcca tgtttagttt   6002

ttgtctcaac atttggaagc tattgaaggt tttaaaatgg tgtgtattgt tttttttgg   6062

ggggggggtg gccagaatag tgggtcatct aataaaactg ccatttaaaa gatcaaaaaa   6122

aaaaaaaaaa aaaaaaaaa                                                6141
```

<210> SEQ ID NO 22
<211> LENGTH: 707
<212> TYPE: PRT
<213> ORGANISM: Mus musculus

<400> SEQUENCE: 22

```
Met Pro Ser Ala Thr Ser His Ser Gly Ser Gly Ser Lys Ser Ser Gly
1               5                   10                  15
```

```
Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
```

```
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Arg
        675                 680                 685

Gly Gly Pro Pro Arg Pro Asn Arg Gly Met Pro Gln Met Asn Thr Gln
    690                 695                 700

Gln Val Asn
705


<210> SEQ ID NO 23
<211> LENGTH: 6114
<212> TYPE: DNA
<213> ORGANISM: Mus musculus
<220> FEATURE:
<221> NAME/KEY: CDS
<222> LOCATION: (139)..(2235)
<223> OTHER INFORMATION:

<400> SEQUENCE: 23

cccaccgcgc gcgcgcgtag ccgcctgccc gcccgcccgc tgcgcgtttt gtcccgcgtc      60

tctccccgtc cgtctcctga cttgctggtc ttgtccttcc ctcccgcttt tttcctctcc     120

tctcttctcg gtctaaag atg ccc tcg gcc acc agc cac agc gga agc ggc       171
                    Met Pro Ser Ala Thr Ser His Ser Gly Ser Gly
                    1               5                   10

agc aaa tcg tcg gga ccg ccg ccg ccg tcc ggt tcc tcc ggg agt gag       219
Ser Lys Ser Ser Gly Pro Pro Pro Pro Ser Gly Ser Ser Gly Ser Glu
            15                  20                  25

gcg gcg gcc ggg gca gct gcg ccg gct tct cag cat ccg gca acc ggc       267
Ala Ala Ala Gly Ala Ala Ala Pro Ala Ser Gln His Pro Ala Thr Gly
        30                  35                  40
```

-continued

```
acc ggc gcc gtc cag acc gag gcc atg aag cag att ctc ggc gta atc      315
Thr Gly Ala Val Gln Thr Glu Ala Met Lys Gln Ile Leu Gly Val Ile
    45                  50                  55

gac aag aaa ctt cgg aac ctg gag aag aaa aag ggt aaa ctt gat gat      363
Asp Lys Lys Leu Arg Asn Leu Glu Lys Lys Lys Gly Lys Leu Asp Asp
60                  65                  70                  75

tac cag gaa cga atg aat aaa ggg gaa agg ctc aat caa gac cag ctg      411
Tyr Gln Glu Arg Met Asn Lys Gly Glu Arg Leu Asn Gln Asp Gln Leu
                80                  85                  90

gat gcc gta tct aag tac cag gaa gtc aca aat aat ttg gag ttt gca      459
Asp Ala Val Ser Lys Tyr Gln Glu Val Thr Asn Asn Leu Glu Phe Ala
            95                  100                 105

aag gaa tta cag agg agt ttc atg gca tta agt caa gat att cag aaa      507
Lys Glu Leu Gln Arg Ser Phe Met Ala Leu Ser Gln Asp Ile Gln Lys
        110                 115                 120

aca ata aag aag aca gca cgt cgg gaa cag ctt atg aga gaa gaa gca      555
Thr Ile Lys Lys Thr Ala Arg Arg Glu Gln Leu Met Arg Glu Glu Ala
    125                 130                 135

gaa cag aag cgc tta aaa act gta ctt gag tta cag tat gta ttg gat      603
Glu Gln Lys Arg Leu Lys Thr Val Leu Glu Leu Gln Tyr Val Leu Asp
140                 145                 150                 155

aag ctg gga gat gat gat gtg aga aca gat ctg aaa caa ggt ttg agt      651
Lys Leu Gly Asp Asp Asp Val Arg Thr Asp Leu Lys Gln Gly Leu Ser
                160                 165                 170

gga gtg cca ata ttg tct gag gag gag ttg tca ttg ctg gat gag ttc      699
Gly Val Pro Ile Leu Ser Glu Glu Glu Leu Ser Leu Leu Asp Glu Phe
            175                 180                 185

tac aag ctc gta gat cct gag cgt gac atg agt tta agg tta aat gag      747
Tyr Lys Leu Val Asp Pro Glu Arg Asp Met Ser Leu Arg Leu Asn Glu
        190                 195                 200

cag tat gaa cat gcc tca att cac ttg tgg gat ttg ctg gaa ggg aaa      795
Gln Tyr Glu His Ala Ser Ile His Leu Trp Asp Leu Leu Glu Gly Lys
    205                 210                 215

gaa aag cct gtg tgt gga aca acc tat aaa gct cta aag gaa att gtt      843
Glu Lys Pro Val Cys Gly Thr Thr Tyr Lys Ala Leu Lys Glu Ile Val
220                 225                 230                 235

gag cgt gtt ttc cag tca aac tac ttt gat agc act cac aat cat caa      891
Glu Arg Val Phe Gln Ser Asn Tyr Phe Asp Ser Thr His Asn His Gln
                240                 245                 250

aat ggg ttg tgt gag gag gaa gag gcg gct tca gcg ccc aca gtg gag      939
Asn Gly Leu Cys Glu Glu Glu Glu Ala Ala Ser Ala Pro Thr Val Glu
            255                 260                 265

gac cag gta gct gaa gct gaa cct gag cca gcg gaa gaa tac aca gag      987
Asp Gln Val Ala Glu Ala Glu Pro Glu Pro Ala Glu Glu Tyr Thr Glu
        270                 275                 280

caa agt gag gtt gaa tca aca gag tat gtc aat agg cag ttc atg gca     1035
Gln Ser Glu Val Glu Ser Thr Glu Tyr Val Asn Arg Gln Phe Met Ala
    285                 290                 295

gaa aca cag ttc agc agt ggt gag aag gag caa gtg gat gag tgg aca     1083
Glu Thr Gln Phe Ser Ser Gly Glu Lys Glu Gln Val Asp Glu Trp Thr
300                 305                 310                 315

gtt gaa aca gtt gag gtt gta aac tca ctc cag cag caa cct cag gct     1131
Val Glu Thr Val Glu Val Val Asn Ser Leu Gln Gln Gln Pro Gln Ala
                320                 325                 330

gcg tcc cct tca gtc cca gag ccc cac tct ttg act cca gtg gct cag     1179
Ala Ser Pro Ser Val Pro Glu Pro His Ser Leu Thr Pro Val Ala Gln
            335                 340                 345

tca gat cca ctt gtg aga agg cag cgt gta caa gat ctt atg gca caa     1227
Ser Asp Pro Leu Val Arg Arg Gln Arg Val Gln Asp Leu Met Ala Gln
        350                 355                 360
```

```
atg caa ggg ccc tat aat ttc ata cag acg ctt gat cct gcc att gta      1275
Met Gln Gly Pro Tyr Asn Phe Ile Gln Thr Leu Asp Pro Ala Ile Val
    365                 370                 375

tcc gca cag cct atg aac cct acc cag aac atg gat atg cct cag ctg      1323
Ser Ala Gln Pro Met Asn Pro Thr Gln Asn Met Asp Met Pro Gln Leu
380                 385                 390                 395

gtt tgc cct cag gtt cat tct gaa tct aga ctt gcc caa tct aat caa      1371
Val Cys Pro Gln Val His Ser Glu Ser Arg Leu Ala Gln Ser Asn Gln
                400                 405                 410

gtt cct gta caa cca gaa gcc aca cag gtt cct ttg gtt tca tcc aca      1419
Val Pro Val Gln Pro Glu Ala Thr Gln Val Pro Leu Val Ser Ser Thr
            415                 420                 425

agt gag ggg tat aca gca tct cag ccc ttg tac cag cca tct cat gct      1467
Ser Glu Gly Tyr Thr Ala Ser Gln Pro Leu Tyr Gln Pro Ser His Ala
        430                 435                 440

acg gag cag cgg ccg cag aaa gag cca atg gat cag att cag gca aca      1515
Thr Glu Gln Arg Pro Gln Lys Glu Pro Met Asp Gln Ile Gln Ala Thr
    445                 450                 455

ata tct ttg aat aca gac cag act aca gca tcc tca tcc ctt cct gct      1563
Ile Ser Leu Asn Thr Asp Gln Thr Thr Ala Ser Ser Ser Leu Pro Ala
460                 465                 470                 475

gct tct cag cct caa gtg ttc cag gct ggg aca agt aaa cct ttg cac      1611
Ala Ser Gln Pro Gln Val Phe Gln Ala Gly Thr Ser Lys Pro Leu His
                480                 485                 490

agc agt gga atc aat gta aat gca gct cca ttc cag tcc atg caa acg      1659
Ser Ser Gly Ile Asn Val Asn Ala Ala Pro Phe Gln Ser Met Gln Thr
            495                 500                 505

gtg ttc aat atg aat gct cca gtc cct cct gct aat gaa cca gaa acg      1707
Val Phe Asn Met Asn Ala Pro Val Pro Pro Ala Asn Glu Pro Glu Thr
        510                 515                 520

tta aaa caa cag agt cag tac cag gcc act tat aac cag agt ttt tcc      1755
Leu Lys Gln Gln Ser Gln Tyr Gln Ala Thr Tyr Asn Gln Ser Phe Ser
    525                 530                 535

agt cag cct cac caa gtg gaa caa aca gag ctt caa caa gac caa ctg      1803
Ser Gln Pro His Gln Val Glu Gln Thr Glu Leu Gln Gln Asp Gln Leu
540                 545                 550                 555

caa acg gtg gtt ggc act tac cat gga tcc cag gac cag cct cat caa      1851
Gln Thr Val Val Gly Thr Tyr His Gly Ser Gln Asp Gln Pro His Gln
                560                 565                 570

gtg cct ggt aac cac cag caa ccc cca cag cag aac act ggc ttt cca      1899
Val Pro Gly Asn His Gln Gln Pro Pro Gln Gln Asn Thr Gly Phe Pro
            575                 580                 585

cgt agc agt cag cct tat tac aac agt cgt ggg gta tct cga gga ggg      1947
Arg Ser Ser Gln Pro Tyr Tyr Asn Ser Arg Gly Val Ser Arg Gly Gly
        590                 595                 600

tct cgt ggt gcc aga ggc ttg atg aat gga tac agg ggc cct gcc aat      1995
Ser Arg Gly Ala Arg Gly Leu Met Asn Gly Tyr Arg Gly Pro Ala Asn
    605                 610                 615

gga ttt aga gga gga tat gat ggt tac cgc cct tca ttc tcg aac act      2043
Gly Phe Arg Gly Gly Tyr Asp Gly Tyr Arg Pro Ser Phe Ser Asn Thr
620                 625                 630                 635

cca aac agt ggt tat tca cag tct cag ttc act gct ccc cgg gac tac      2091
Pro Asn Ser Gly Tyr Ser Gln Ser Gln Phe Thr Ala Pro Arg Asp Tyr
                640                 645                 650

tct ggt tac cag cgg gat gga tat cag cag aat ttc aag cga ggc tct      2139
Ser Gly Tyr Gln Arg Asp Gly Tyr Gln Gln Asn Phe Lys Arg Gly Ser
            655                 660                 665

ggg cag agt gga cca cgg gga gcc cca cga ggt cgt gga ggg ccc cca      2187
Gly Gln Ser Gly Pro Arg Gly Ala Pro Arg Gly Arg Gly Gly Pro Pro
        670                 675                 680
```

```
aga ccc aac aga ggg atg ccg caa atg aac act cag caa gtg aat taa     2235
Arg Pro Asn Arg Gly Met Pro Gln Met Asn Thr Gln Gln Val Asn
    685                 690                 695

tgtgatacac aggattatgt ttaatcgcca aaaacacact ggccagtgta ccataatatg   2295

ttaccagaag agttattatc tatttgttct ccctttcagg aaacttattg taaagggact   2355

gttttcatcc cataaagaca ggactgcaat tgtcagcttt acattacctg gatatggaag   2415

gaaactattt ttattctgca tgttctgtcc taagcgtcat cttgagcctt gcacacaata   2475

caatactcag attcctcacc cttgcttagg agtaaaacat tatatactta tggggtgata   2535

atatctccat agttagttga agtggcttgg aaaaaaaatg caagattgaa tttttgacct   2595

tggataaaat ctacaatcag ccctagaact attcagtggt aattgacaaa gttaaagcat   2655

tttctttgaa aggaagatgg aaggagtgga gtgtggttta gcaaaactgc atttcatagc   2715

tttcccatta aattggagca ccgacagatt aaaagcatac caaattatgc atgggtcctt   2775

actcacacaa gtgaggctgg ctaccagcct tgacatagca ctcactagtc ttctggccaa   2835

acgactgtga ttaaaacaca tgtaaattgc tctttagtag tggatactgt gtaagacaaa   2895

gccaaattgc aaatcaggct ttgattggct cttctggaaa atatgcatca aatatggggg   2955

ataatctgga tgggctgctg ctgtgctcaa tgtgaactat ttagatacct ttggaacact   3015

taacagtttc tctgaacaat gacttacatg gggattggtc ctgtttgtca ttcctcacca   3075

taattgcatt gtcatcacta atccttggat cttgctgtat tgttactcaa attggtaata   3135

ggtactgatg gaaatcgcta atggatggat aatcataaca cttttggtca catgttttct   3195

cctgcagcct gaaagttctt aaagaaaaag atatcaaatg cctgctgcta ccaccctttt   3255

aaattgctat ctttagaaaa gcaccggtat gtgttttaga ttcatttccc tgttttaggg   3315

aaatgacagg cagtagtttc agttctgatg gcaaaacaaa taaaaacatg tttctaaaag   3375

ttgtatcttg aaacactggt gttcaacagc tagcagctaa agtaattcaa cccatgcatt   3435

gctagtgtca cagcctttgg ttatgtctag tagctgtttc tgaagtattt tcatttatct   3495

tttgtcaaat ttaaccctgt ttgaattctc tcctttcctc aaggagacac ttatgttcaa   3555

agtgttgatt ctttgcctta ggtgcataga gagtagacag tttggagatg gaaaggttag   3615

cagtgactta gccatatgtt ctgtgttgga atttgtgcta gcagtttgag cactagctct   3675

gcgtgcctat gaactgaatg ctgcttgtcc cattccattt tatgtcatgg agaaataatt   3735

ccacttggta acacaaaggc taagttaatg ttattttctg tacagaaatt aaattttact   3795

tttagccttt tgtaaacttt tttttttttt ttccaagccg gtatcagcta ctcaaaacaa   3855

ttctcagata ttcatcatta gacaactgga gtttttgctg gttttgtagc ctactaaaac   3915

tgctgaggct gttgaacatt ccacattcaa aagttttgta gggtggtgga taatggggaa   3975

gcttcaatgt ttattttaaa ataaataaaa taagttcttg acttttctca tgtgtggtta   4035

tggtacatca tattggaagg gttatctgtt tacttttgcc aagactattt tgccagcacc   4095

tacacttgtg tgctttaaaa gacaactacc tgggatgtac cacaaccata tgttaattgt   4155

attttattgg gatggataaa atgtttgtgg tttattggat aatccctaga tggtgtgtta   4215

cgtgtgtaga atataatttt atgatagtaa gaaagcaaaa ttgaagaaaa taagtttagt   4275

attgaatttg agttctgaag tgaattcagg gaatgtctca cgtttcgggc ttctacccaa   4335

agtgtagggc agaaggtgta aaagttgttt gtagtttgac ttgtttattt tttaagttgc   4395

ttattccttt caacagcaac atatcattag ctgtcattct accattgcag ttctagtgag   4455

ttttaacgtc tgcattcaag actgttttaa aagcaacctc actggacaga gaactgctaa   4515
```

```
agtcttttcc ttaagatctg agtctttgtt actcagtatc ttctataata tgcaaatgct   4575

tgtctagagg cagaagacct tttgtttggt caagtgtgta ttttaccaga gtacagggaa   4635

ctgatggtcc tacatgtctc ttagtgtagt aagactataa aatcttttgt acatgcacaa   4695

ttcacagtat gtttagatac cacgtgtata atgccccccc ctcccccagg tagcatgcca   4755

ttgatgactt tttgcttagg gccattttat taccagggcc ttaatattcc taaaaagatg   4815

attttttttc atcctttctc ctcttttgat cattgtatct tgatattaaa aacatgacct   4875

tccaatgatt gtagtaaatt aacttctata gttcttttgt ctctatatgt attcatatat   4935

atgctattgt atagagactt caaggagaca tggagatgca tgcttattct caggttcatt   4995

cactaaggtg cttggcagac aaccagtttc taagtgcaga atgtagttaa gcagcttcat   5055

atatgtgcca ggcaatttgt tttgttaaat tttcatctac ttaaggaaat agggtattgt   5115

agcttaggct gatcataccc ttcatttcaa ccttaagctc tcaacctgca tccatccgac   5175

ttgagctatt aagtacttta gttttatcga gtataagtta acagaaaaag taaattaagc   5235

tttgccttta ctattttgaa tttatataca ttctggaaaa acttagaaac tgttgtatat   5295

ttcattagat taaattatat gaaaatgtga ttgtttatag caaagcctgt gagttgcata   5355

caccctaagg aaaactcctt aagtgctcct tgaagagaga agaaacaatt ctgggtctgg   5415

tctttttaag aacaaagcta gactactgta tgttagcact gtacattaat agtctgttgt   5475

gaagcttgag cagtttcctg catagccttg atccttcacc gttggcattg aaaatagcag   5535

tatccctgat gtacttaaaa cttaaagtca ggttttggta tatttatttg taagtcttaa   5595

tttcctctaa atactatatc tctttagcga gacaacctga aatttattag cacatttggg   5655

tatctcttgc ttggcattat ggccagtgtt aactattcag tggtgaaaaa attacccctc   5715

aagacactgg agtgacccca gatgtgtgta gtaagtggca tggttcaact gtgtggttaa   5775

tgataaatat atgacttagt cggtatgatc tggaaagact tgattgaaag ataattcagc   5835

tgacataagg atgagtgagg agtggcaaac tggataaaag agtcaagaga cctgtattcc   5895

agtgactcct gttttgttta agcattagca agatctgtct ggggaaactg gatagggcag   5955

ttttcttcca tgtttagttt ttgtctcaac atttggaagc tattgaaggt tttaaaatgg   6015

tgtgtattgt ttttttttgg ggggggggtg gccagaatag tgggtcatct aataaaactg   6075

ccatttaaaa gatcaaaaaa aaaaaaaaaa aaaaaaaaa                          6114
```

<210> SEQ ID NO 24
<211> LENGTH: 698
<212> TYPE: PRT
<213> ORGANISM: Mus musculus

<400> SEQUENCE: 24

```
Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95
```

```
Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Thr Leu Asp Pro Ala Ile Val Ser Ala Gln Pro Met
    370                 375                 380

Asn Pro Thr Gln Asn Met Asp Met Pro Gln Leu Val Cys Pro Gln Val
385                 390                 395                 400

His Ser Glu Ser Arg Leu Ala Gln Ser Asn Gln Val Pro Val Gln Pro
                405                 410                 415

Glu Ala Thr Gln Val Pro Leu Val Ser Ser Thr Ser Glu Gly Tyr Thr
            420                 425                 430

Ala Ser Gln Pro Leu Tyr Gln Pro Ser His Ala Thr Glu Gln Arg Pro
        435                 440                 445

Gln Lys Glu Pro Met Asp Gln Ile Gln Ala Thr Ile Ser Leu Asn Thr
    450                 455                 460

Asp Gln Thr Thr Ala Ser Ser Ser Leu Pro Ala Ala Ser Gln Pro Gln
465                 470                 475                 480

Val Phe Gln Ala Gly Thr Ser Lys Pro Leu His Ser Ser Gly Ile Asn
                485                 490                 495

Val Asn Ala Ala Pro Phe Gln Ser Met Gln Thr Val Phe Asn Met Asn
            500                 505                 510

Ala Pro Val Pro Pro Ala Asn Glu Pro Glu Thr Leu Lys Gln Gln Ser
```

```
        515                 520                 525

Gln Tyr Gln Ala Thr Tyr Asn Gln Ser Phe Ser Ser Gln Pro His Gln
    530                 535                 540

Val Glu Gln Thr Glu Leu Gln Gln Asp Gln Leu Gln Thr Val Val Gly
545                 550                 555                 560

Thr Tyr His Gly Ser Gln Asp Gln Pro His Gln Val Pro Gly Asn His
                565                 570                 575

Gln Gln Pro Pro Gln Gln Asn Thr Gly Phe Pro Arg Ser Ser Gln Pro
            580                 585                 590

Tyr Tyr Asn Ser Arg Gly Val Ser Arg Gly Gly Ser Arg Gly Ala Arg
        595                 600                 605

Gly Leu Met Asn Gly Tyr Arg Gly Pro Ala Asn Gly Phe Arg Gly Gly
    610                 615                 620

Tyr Asp Gly Tyr Arg Pro Ser Phe Ser Asn Thr Pro Asn Ser Gly Tyr
625                 630                 635                 640

Ser Gln Ser Gln Phe Thr Ala Pro Arg Asp Tyr Ser Gly Tyr Gln Arg
                645                 650                 655

Asp Gly Tyr Gln Gln Asn Phe Lys Arg Gly Ser Gly Gln Ser Gly Pro
            660                 665                 670

Arg Gly Ala Pro Arg Gly Arg Gly Gly Pro Pro Arg Pro Asn Arg Gly
        675                 680                 685

Met Pro Gln Met Asn Thr Gln Gln Val Asn
    690                 695
```

<210> SEQ ID NO 25
<211> LENGTH: 3548
<212> TYPE: DNA
<213> ORGANISM: Mus musculus
<220> FEATURE:
<221> NAME/KEY: CDS
<222> LOCATION: (179)..(2257)
<223> OTHER INFORMATION:

<400> SEQUENCE: 25

```
gctggctggc taagtccctc ccgcgccggc tcttgtccca ctaggagcag ctcagagccg      60

cggggacagg gcgaagcggc ctgcgcccac ggagcgcacg tctctgttct caacgcagca     120

ccacccttgc ccccctcggc tgcccactcc agacgtccag cggctccgcg cgcgcacg       178

atg ccc tcg gcc acc agc cac agc gga agc ggc agc aaa tcg tcg gga       226
Met Pro Ser Ala Thr Ser His Ser Gly Ser Gly Ser Lys Ser Ser Gly
1               5                   10                  15

ccg ccg ccg ccg tcc ggt tcc tcc ggg agt gag gcg gcg gcc ggg gca       274
Pro Pro Pro Pro Ser Gly Ser Ser Gly Ser Glu Ala Ala Ala Gly Ala
            20                  25                  30

gct gcg ccg gct tct cag cat ccg gca acc ggc acc ggc gcc gtc cag       322
Ala Ala Pro Ala Ser Gln His Pro Ala Thr Gly Thr Gly Ala Val Gln
        35                  40                  45

acc gag gcc atg aag cag att ctc ggc gta atc gac aag aaa ctt cgg       370
Thr Glu Ala Met Lys Gln Ile Leu Gly Val Ile Asp Lys Lys Leu Arg
    50                  55                  60

aac ctg gag aag aaa aag ggt aaa ctt gat gat tac cag gaa cga atg       418
Asn Leu Glu Lys Lys Lys Gly Lys Leu Asp Asp Tyr Gln Glu Arg Met
65                  70                  75                  80

aat aaa ggg gaa agg ctc aat caa gac cag ctg gat gcc gta tct aag       466
Asn Lys Gly Glu Arg Leu Asn Gln Asp Gln Leu Asp Ala Val Ser Lys
                85                  90                  95

tac cag gaa gtc aca aat aat ttg gag ttt gca aag gaa tta cag agg       514
Tyr Gln Glu Val Thr Asn Asn Leu Glu Phe Ala Lys Glu Leu Gln Arg
            100                 105                 110
```

```
agt ttc atg gca tta agt caa gat att cag aaa aca ata aag aag aca      562
Ser Phe Met Ala Leu Ser Gln Asp Ile Gln Lys Thr Ile Lys Lys Thr
        115                 120                 125

gca cgt cgg gaa cag ctt atg aga gaa gaa gca gaa cag aag cgc tta      610
Ala Arg Arg Glu Gln Leu Met Arg Glu Glu Ala Glu Gln Lys Arg Leu
    130                 135                 140

aaa act gta ctt gag tta cag tat gta ttg gat aag ctg gga gat gat      658
Lys Thr Val Leu Glu Leu Gln Tyr Val Leu Asp Lys Leu Gly Asp Asp
145                 150                 155                 160

gat gtg aga aca gat ctg aaa caa ggt ttg agt gga gtg cca ata ttg      706
Asp Val Arg Thr Asp Leu Lys Gln Gly Leu Ser Gly Val Pro Ile Leu
                165                 170                 175

tct gag gag gag ttg tca ttg ctg gat gag ttc tac aag ctc gta gat      754
Ser Glu Glu Glu Leu Ser Leu Leu Asp Glu Phe Tyr Lys Leu Val Asp
            180                 185                 190

cct gag cgt gac atg agt tta agg tta aat gag cag tat gaa cat gcc      802
Pro Glu Arg Asp Met Ser Leu Arg Leu Asn Glu Gln Tyr Glu His Ala
        195                 200                 205

tca att cac ttg tgg gat ttg ctg gaa ggg aaa gaa aag cct gtg tgt      850
Ser Ile His Leu Trp Asp Leu Leu Glu Gly Lys Glu Lys Pro Val Cys
    210                 215                 220

gga aca acc tat aaa gct cta aag gaa att gtt gag cgt gtt ttc cag      898
Gly Thr Thr Tyr Lys Ala Leu Lys Glu Ile Val Glu Arg Val Phe Gln
225                 230                 235                 240

tca aac tac ttt gat agc act cac aat cat caa aat ggg ttg tgt gag      946
Ser Asn Tyr Phe Asp Ser Thr His Asn His Gln Asn Gly Leu Cys Glu
                245                 250                 255

gag gaa gag gcg gct tca gcg ccc aca gtg gag gac cag gta gct gaa      994
Glu Glu Glu Ala Ala Ser Ala Pro Thr Val Glu Asp Gln Val Ala Glu
            260                 265                 270

gct gaa cct gag cca gcg gaa gaa tac aca gag caa agt gag gtt gaa     1042
Ala Glu Pro Glu Pro Ala Glu Glu Tyr Thr Glu Gln Ser Glu Val Glu
        275                 280                 285

tca aca gag tat gtc aat agg cag ttc atg gca gaa aca cag ttc agc     1090
Ser Thr Glu Tyr Val Asn Arg Gln Phe Met Ala Glu Thr Gln Phe Ser
    290                 295                 300

agt ggt gag aag gag caa gtg gat gag tgg aca gtt gaa aca gtt gag     1138
Ser Gly Glu Lys Glu Gln Val Asp Glu Trp Thr Val Glu Thr Val Glu
305                 310                 315                 320

gtt gta aac tca ctc cag cag caa cct cag gct gcg tcc cct tca gtc     1186
Val Val Asn Ser Leu Gln Gln Gln Pro Gln Ala Ala Ser Pro Ser Val
                325                 330                 335

cca gag ccc cac tct ttg act cca gtg gct cag tca gat cca ctt gtg     1234
Pro Glu Pro His Ser Leu Thr Pro Val Ala Gln Ser Asp Pro Leu Val
            340                 345                 350

aga agg cag cgt gta caa gat ctt atg gca caa atg caa ggg ccc tat     1282
Arg Arg Gln Arg Val Gln Asp Leu Met Ala Gln Met Gln Gly Pro Tyr
        355                 360                 365

aat ttc ata cag gat tca atg ttg gat ttt gaa aat cag acg ctt gat     1330
Asn Phe Ile Gln Asp Ser Met Leu Asp Phe Glu Asn Gln Thr Leu Asp
    370                 375                 380

cct gcc att gta tcc gca cag cct atg aac cct acc cag aac atg gat     1378
Pro Ala Ile Val Ser Ala Gln Pro Met Asn Pro Thr Gln Asn Met Asp
385                 390                 395                 400

atg cct cag ctg gtt tgc cct cag gtt cat tct gaa tct aga ctt gcc     1426
Met Pro Gln Leu Val Cys Pro Gln Val His Ser Glu Ser Arg Leu Ala
                405                 410                 415

caa tct aat caa gtt cct gta caa cca gaa gcc aca cag gtt cct ttg     1474
Gln Ser Asn Gln Val Pro Val Gln Pro Glu Ala Thr Gln Val Pro Leu
            420                 425                 430
```

```
gtt tca tcc aca agt gag ggg tat aca gca tct cag ccc ttg tac cag      1522
Val Ser Ser Thr Ser Glu Gly Tyr Thr Ala Ser Gln Pro Leu Tyr Gln
        435                 440                 445

cca tct cat gct acg gag cag cgg ccg cag aaa gag cca atg gat cag      1570
Pro Ser His Ala Thr Glu Gln Arg Pro Gln Lys Glu Pro Met Asp Gln
    450                 455                 460

att cag gca aca ata tct ttg aat aca gac cag act aca gca tcc tca      1618
Ile Gln Ala Thr Ile Ser Leu Asn Thr Asp Gln Thr Thr Ala Ser Ser
465                 470                 475                 480

tcc ctt cct gct gct tct cag cct caa gtg ttc cag gct ggg aca agt      1666
Ser Leu Pro Ala Ala Ser Gln Pro Gln Val Phe Gln Ala Gly Thr Ser
                485                 490                 495

aaa cct ttg cac agc agt gga atc aat gta aat gca gct cca ttc cag      1714
Lys Pro Leu His Ser Ser Gly Ile Asn Val Asn Ala Ala Pro Phe Gln
            500                 505                 510

tcc atg caa acg gtg ttc aat atg aat gct cca gtc cct cct gct aat      1762
Ser Met Gln Thr Val Phe Asn Met Asn Ala Pro Val Pro Pro Ala Asn
        515                 520                 525

gaa cca gaa acg tta aaa caa cag agt cag tac cag gcc act tat aac      1810
Glu Pro Glu Thr Leu Lys Gln Gln Ser Gln Tyr Gln Ala Thr Tyr Asn
    530                 535                 540

cag agt ttt tcc agt cag cct cac caa gtg gaa caa aca gag ctt caa      1858
Gln Ser Phe Ser Ser Gln Pro His Gln Val Glu Gln Thr Glu Leu Gln
545                 550                 555                 560

caa gac caa ctg caa acg gtg gtt ggc act tac cat gga tcc cag gac      1906
Gln Asp Gln Leu Gln Thr Val Val Gly Thr Tyr His Gly Ser Gln Asp
                565                 570                 575

cag cct cat caa gtg cct ggt aac cac cag caa ccc cca cag cag aac      1954
Gln Pro His Gln Val Pro Gly Asn His Gln Gln Pro Pro Gln Gln Asn
            580                 585                 590

act ggc ttt cca cgt agc agt cag cct tat tac aac agt cgt ggg gta      2002
Thr Gly Phe Pro Arg Ser Ser Gln Pro Tyr Tyr Asn Ser Arg Gly Val
        595                 600                 605

tct cga gga ggg tct cgt ggt gcc aga ggc ttg atg aat gga tac agg      2050
Ser Arg Gly Gly Ser Arg Gly Ala Arg Gly Leu Met Asn Gly Tyr Arg
    610                 615                 620

ggc cct gcc aat gga ttt aga gga gga tat gat ggt tac cgc cct tca      2098
Gly Pro Ala Asn Gly Phe Arg Gly Gly Tyr Asp Gly Tyr Arg Pro Ser
625                 630                 635                 640

ttc tcg aac act cca aac agt ggt tat tca cag tct cag ttc act gct      2146
Phe Ser Asn Thr Pro Asn Ser Gly Tyr Ser Gln Ser Gln Phe Thr Ala
                645                 650                 655

ccc cgg gac tac tct ggt tac cag cgg gat gga tat cag cag aat ttc      2194
Pro Arg Asp Tyr Ser Gly Tyr Gln Arg Asp Gly Tyr Gln Gln Asn Phe
            660                 665                 670

aag cga ggc tct ggg cag agt gga cca cgg gga gcc cca cga ggt aat      2242
Lys Arg Gly Ser Gly Gln Ser Gly Pro Arg Gly Ala Pro Arg Gly Asn
        675                 680                 685

ata ttg tgg tgg tga tcctagctcc tatgtggagc ttctgttctg gccttggaag      2297
Ile Leu Trp Trp
    690

aactgttcat agtccgcatg taggttacat gttaggaata catttatctt ttccagactt    2357

gttgctaaag attaaatgaa atgctctgtt tctaaaattt catcttgaat ccaaatttta    2417

atttttgaat gactttccct gctgttgtct tcaaaatcag aacattttct ctgcctcaga    2477

aaagcgtttt tccaactgga aatttatttt tcaggtctta aaacctgcta aatgttttta    2537

ggaagtacct actgaaactt tttgtaagac atttttggaa cgagcttgaa catttatata    2597

aatttattac cctctttgat ttttgaaaca tgcatattat atttaggctg agaagccctt    2657
```

```
caaatggcca gataagccac agttttagct agagaaccat ttagaattga cataactaat   2717

ctaaacttga acacttttag gaccaatgtt agtgttctaa ataccaacat atttctgatg   2777

tttaaacaga tctcccaaat tcttaggacc ttgatgtcat taaaatttag aatgacaagc   2837

ttaagaggct ttagtttcat ttgtttttca agtaatgaaa aataatttct tacatgggca   2897

gatagttaat ttgttgaaca attacaggta gcatttcatg taatctgatg ttctaaatgg   2957

ttctcttatt gaaggaggtt aaagaattag gtttcttaca gtttttggct ggccatgaca   3017

tgtataaaat gtatattaag gaggaattat aaagtacttt aatttgaatg ctagtggcaa   3077

ttgatcatta agaaagtact ttaaagcaaa aggttaatgg gtcatctggg aaaaatactg   3137

aagtatcaaa ggtatttgca tgtgaatgtg ggttatgttc ttctatccca ccttgtagca   3197

tattctatga aagttgagtt aaatgatagc taaaatatct gtttcaacag catgtaaaaa   3257

gttattttaa ctgttacaag tcattataca attttgaatg ttctgtagtt tctttttaac   3317

agtttaggta caaaggtctg ttttcattct ggtgcttttt attaattttg atagtatgat   3377

gtcacttcct attgaaatgt aagctagcgt gtaccttaga atgtgagctc catgagagca   3437

ggtaccttgt ttgtcttcac tgctgtatct attcccaacg cctcatgaca gtgcctggca   3497

catagtaggc actcaataaa tacttgttga atgaatgaaa aaaaaaaaaa a            3548
```

```
<210> SEQ ID NO 26
<211> LENGTH: 692
<212> TYPE: PRT
<213> ORGANISM: Mus musculus

<400> SEQUENCE: 26

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220
```

```
Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
```

```
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Asn
        675                 680                 685

Ile Leu Trp Trp
    690


<210> SEQ ID NO 27
<211> LENGTH: 3508
<212> TYPE: DNA
<213> ORGANISM: Mus musculus
<220> FEATURE:
<221> NAME/KEY: CDS
<222> LOCATION: (139)..(2217)
<223> OTHER INFORMATION:

<400> SEQUENCE: 27

cccaccgcgc gcgcgcgtag ccgcctgccc gcccgcccgc tgcgcgtttt gtcccgcgtc      60

tctccccgtc cgtctcctga cttgctggtc ttgtccttcc ctcccgcttt tttcctctcc     120

tctcttctcg gtctaaag atg ccc tcg gcc acc agc cac agc gga agc ggc       171
                    Met Pro Ser Ala Thr Ser His Ser Gly Ser Gly
                    1               5                   10

agc aaa tcg tcg gga ccg ccg ccg ccg tcc ggt tcc tcc ggg agt gag       219
Ser Lys Ser Ser Gly Pro Pro Pro Pro Ser Gly Ser Ser Gly Ser Glu
            15                  20                  25

gcg gcg gcc ggg gca gct gcg ccg gct tct cag cat ccg gca acc ggc       267
Ala Ala Ala Gly Ala Ala Ala Pro Ala Ser Gln His Pro Ala Thr Gly
        30                  35                  40

acc ggc gcc gtc cag acc gag gcc atg aag cag att ctc ggc gta atc       315
Thr Gly Ala Val Gln Thr Glu Ala Met Lys Gln Ile Leu Gly Val Ile
    45                  50                  55

gac aag aaa ctt cgg aac ctg gag aag aaa aag ggt aaa ctt gat gat       363
Asp Lys Lys Leu Arg Asn Leu Glu Lys Lys Lys Gly Lys Leu Asp Asp
60                  65                  70                  75

tac cag gaa cga atg aat aaa ggg gaa agg ctc aat caa gac cag ctg       411
Tyr Gln Glu Arg Met Asn Lys Gly Glu Arg Leu Asn Gln Asp Gln Leu
                80                  85                  90

gat gcc gta tct aag tac cag gaa gtc aca aat aat ttg gag ttt gca       459
Asp Ala Val Ser Lys Tyr Gln Glu Val Thr Asn Asn Leu Glu Phe Ala
            95                  100                 105

aag gaa tta cag agg agt ttc atg gca tta agt caa gat att cag aaa       507
Lys Glu Leu Gln Arg Ser Phe Met Ala Leu Ser Gln Asp Ile Gln Lys
        110                 115                 120

aca ata aag aag aca gca cgt cgg gaa cag ctt atg aga gaa gaa gca       555
Thr Ile Lys Lys Thr Ala Arg Arg Glu Gln Leu Met Arg Glu Glu Ala
    125                 130                 135

gaa cag aag cgc tta aaa act gta ctt gag tta cag tat gta ttg gat       603
Glu Gln Lys Arg Leu Lys Thr Val Leu Glu Leu Gln Tyr Val Leu Asp
140                 145                 150                 155

aag ctg gga gat gat gat gtg aga aca gat ctg aaa caa ggt ttg agt       651
Lys Leu Gly Asp Asp Asp Val Arg Thr Asp Leu Lys Gln Gly Leu Ser
                160                 165                 170

gga gtg cca ata ttg tct gag gag gag ttg tca ttg ctg gat gag ttc       699
Gly Val Pro Ile Leu Ser Glu Glu Glu Leu Ser Leu Leu Asp Glu Phe
            175                 180                 185

tac aag ctc gta gat cct gag cgt gac atg agt tta agg tta aat gag       747
Tyr Lys Leu Val Asp Pro Glu Arg Asp Met Ser Leu Arg Leu Asn Glu
        190                 195                 200

cag tat gaa cat gcc tca att cac ttg tgg gat ttg ctg gaa ggg aaa       795
```

```
Gln Tyr Glu His Ala Ser Ile His Leu Trp Asp Leu Leu Glu Gly Lys
    205                 210                 215

gaa aag cct gtg tgt gga aca acc tat aaa gct cta aag gaa att gtt      843
Glu Lys Pro Val Cys Gly Thr Thr Tyr Lys Ala Leu Lys Glu Ile Val
220                 225                 230                 235

gag cgt gtt ttc cag tca aac tac ttt gat agc act cac aat cat caa      891
Glu Arg Val Phe Gln Ser Asn Tyr Phe Asp Ser Thr His Asn His Gln
                240                 245                 250

aat ggg ttg tgt gag gag gaa gag gcg gct tca gcg ccc aca gtg gag      939
Asn Gly Leu Cys Glu Glu Glu Glu Ala Ala Ser Ala Pro Thr Val Glu
            255                 260                 265

gac cag gta gct gaa gct gaa cct gag cca gcg gaa gaa tac aca gag      987
Asp Gln Val Ala Glu Ala Glu Pro Glu Pro Ala Glu Glu Tyr Thr Glu
        270                 275                 280

caa agt gag gtt gaa tca aca gag tat gtc aat agg cag ttc atg gca     1035
Gln Ser Glu Val Glu Ser Thr Glu Tyr Val Asn Arg Gln Phe Met Ala
    285                 290                 295

gaa aca cag ttc agc agt ggt gag aag gag caa gtg gat gag tgg aca     1083
Glu Thr Gln Phe Ser Ser Gly Glu Lys Glu Gln Val Asp Glu Trp Thr
300                 305                 310                 315

gtt gaa aca gtt gag gtt gta aac tca ctc cag cag caa cct cag gct     1131
Val Glu Thr Val Glu Val Val Asn Ser Leu Gln Gln Gln Pro Gln Ala
                320                 325                 330

gcg tcc cct tca gtc cca gag ccc cac tct ttg act cca gtg gct cag     1179
Ala Ser Pro Ser Val Pro Glu Pro His Ser Leu Thr Pro Val Ala Gln
            335                 340                 345

tca gat cca ctt gtg aga agg cag cgt gta caa gat ctt atg gca caa     1227
Ser Asp Pro Leu Val Arg Arg Gln Arg Val Gln Asp Leu Met Ala Gln
        350                 355                 360

atg caa ggg ccc tat aat ttc ata cag gat tca atg ttg gat ttt gaa     1275
Met Gln Gly Pro Tyr Asn Phe Ile Gln Asp Ser Met Leu Asp Phe Glu
    365                 370                 375

aat cag acg ctt gat cct gcc att gta tcc gca cag cct atg aac cct     1323
Asn Gln Thr Leu Asp Pro Ala Ile Val Ser Ala Gln Pro Met Asn Pro
380                 385                 390                 395

acc cag aac atg gat atg cct cag ctg gtt tgc cct cag gtt cat tct     1371
Thr Gln Asn Met Asp Met Pro Gln Leu Val Cys Pro Gln Val His Ser
                400                 405                 410

gaa tct aga ctt gcc caa tct aat caa gtt cct gta caa cca gaa gcc     1419
Glu Ser Arg Leu Ala Gln Ser Asn Gln Val Pro Val Gln Pro Glu Ala
            415                 420                 425

aca cag gtt cct ttg gtt tca tcc aca agt gag ggg tat aca gca tct     1467
Thr Gln Val Pro Leu Val Ser Ser Thr Ser Glu Gly Tyr Thr Ala Ser
        430                 435                 440

cag ccc ttg tac cag cca tct cat gct acg gag cag cgg ccg cag aaa     1515
Gln Pro Leu Tyr Gln Pro Ser His Ala Thr Glu Gln Arg Pro Gln Lys
    445                 450                 455

gag cca atg gat cag att cag gca aca ata tct ttg aat aca gac cag     1563
Glu Pro Met Asp Gln Ile Gln Ala Thr Ile Ser Leu Asn Thr Asp Gln
460                 465                 470                 475

act aca gca tcc tca tcc ctt cct gct gct tct cag cct caa gtg ttc     1611
Thr Thr Ala Ser Ser Ser Leu Pro Ala Ala Ser Gln Pro Gln Val Phe
                480                 485                 490

cag gct ggg aca agt aaa cct ttg cac agc agt gga atc aat gta aat     1659
Gln Ala Gly Thr Ser Lys Pro Leu His Ser Ser Gly Ile Asn Val Asn
            495                 500                 505

gca gct cca ttc cag tcc atg caa acg gtg ttc aat atg aat gct cca     1707
Ala Ala Pro Phe Gln Ser Met Gln Thr Val Phe Asn Met Asn Ala Pro
        510                 515                 520

gtc cct cct gct aat gaa cca gaa acg tta aaa caa cag agt cag tac     1755
```

```
Val Pro Pro Ala Asn Glu Pro Glu Thr Leu Lys Gln Gln Ser Gln Tyr
    525                 530                 535

cag gcc act tat aac cag agt ttt tcc agt cag cct cac caa gtg gaa     1803
Gln Ala Thr Tyr Asn Gln Ser Phe Ser Ser Gln Pro His Gln Val Glu
540                 545                 550                 555

caa aca gag ctt caa caa gac caa ctg caa acg gtg gtt ggc act tac     1851
Gln Thr Glu Leu Gln Gln Asp Gln Leu Gln Thr Val Val Gly Thr Tyr
                560                 565                 570

cat gga tcc cag gac cag cct cat caa gtg cct ggt aac cac cag caa     1899
His Gly Ser Gln Asp Gln Pro His Gln Val Pro Gly Asn His Gln Gln
            575                 580                 585

ccc cca cag cag aac act ggc ttt cca cgt agc agt cag cct tat tac     1947
Pro Pro Gln Gln Asn Thr Gly Phe Pro Arg Ser Ser Gln Pro Tyr Tyr
        590                 595                 600

aac agt cgt ggg gta tct cga gga ggg tct cgt ggt gcc aga ggc ttg     1995
Asn Ser Arg Gly Val Ser Arg Gly Gly Ser Arg Gly Ala Arg Gly Leu
    605                 610                 615

atg aat gga tac agg ggc cct gcc aat gga ttt aga gga gga tat gat     2043
Met Asn Gly Tyr Arg Gly Pro Ala Asn Gly Phe Arg Gly Gly Tyr Asp
620                 625                 630                 635

ggt tac cgc cct tca ttc tcg aac act cca aac agt ggt tat tca cag     2091
Gly Tyr Arg Pro Ser Phe Ser Asn Thr Pro Asn Ser Gly Tyr Ser Gln
                640                 645                 650

tct cag ttc act gct ccc cgg gac tac tct ggt tac cag cgg gat gga     2139
Ser Gln Phe Thr Ala Pro Arg Asp Tyr Ser Gly Tyr Gln Arg Asp Gly
            655                 660                 665

tat cag cag aat ttc aag cga ggc tct ggg cag agt gga cca cgg gga     2187
Tyr Gln Gln Asn Phe Lys Arg Gly Ser Gly Gln Ser Gly Pro Arg Gly
        670                 675                 680

gcc cca cga ggt aat ata ttg tgg tgg tga tcctagctcc tatgtggagc       2237
Ala Pro Arg Gly Asn Ile Leu Trp Trp
    685                 690

ttctgttctg gccttggaag aactgttcat agtccgcatg taggttacat gttaggaata   2297

catttatctt ttccagactt gttgctaaag attaaatgaa atgctctgtt tctaaaattt   2357

catcttgaat ccaaatttta atttttgaat gactttccct gctgttgtct tcaaaatcag   2417

aacattttct ctgcctcaga aaagcgtttt tccaactgga aatttatttt tcaggtctta   2477

aaacctgcta aatgttttta ggaagtacct actgaaactt tttgtaagac atttttggaa   2537

cgagcttgaa catttatata aatttattac cctctttgat ttttgaaaca tgcatattat   2597

atttaggctg agaagccctt caaatggcca gataagccac agttttagct agagaaccat   2657

ttagaattga cataactaat ctaaacttga acacttttag gaccaatgtt agtgttctaa   2717

ataccaacat atttctgatg tttaaacaga tctcccaaat tcttaggacc ttgatgtcat   2777

taaaatttag aatgacaagc ttaagaggct ttagtttcat ttgtttttca agtaatgaaa   2837

aataatttct tacatgggca gatagttaat ttgttgaaca attacaggta gcatttcatg   2897

taatctgatg ttctaaatgg ttctcttatt gaaggaggtt aaagaattag gtttcttaca   2957

gtttttggct ggccatgaca tgtataaaat gtatattaag gaggaattat aaagtacttt   3017

aatttgaatg ctagtggcaa ttgatcatta agaaagtact ttaaagcaaa aggttaatgg   3077

gtcatctggg aaaaatactg aagtatcaaa ggtatttgca tgtgaatgtg ggttatgttc   3137

ttctatccca ccttgtagca tattctatga aagttgagtt aaatgatagc taaaatatct   3197

gtttcaacag catgtaaaaa gttattttaa ctgttacaag tcattataca attttgaatg   3257

ttctgtagtt tctttttaac agtttaggta caaaggtctg ttttcattct ggtgcttttt   3317

attaatttg atagtatgat gtcacttcct attgaaatgt aagctagcgt gtaccttaga   3377
```

```
atgtgagctc catgagagca ggtaccttgt ttgtcttcac tgctgtatct attcccaacg   3437

cctcatgaca gtgcctggca catagtaggc actcaataaa tacttgttga atgaatgaaa   3497

aaaaaaaaaa a                                                         3508


<210> SEQ ID NO 28
<211> LENGTH: 692
<212> TYPE: PRT
<213> ORGANISM: Mus musculus

<400> SEQUENCE: 28

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350
```

```
Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Asn
        675                 680                 685

Ile Leu Trp Trp
    690


<210> SEQ ID NO 29
<211> LENGTH: 2109
<212> TYPE: DNA
<213> ORGANISM: Gallus gallus
<220> FEATURE:
<221> NAME/KEY: CDS
<222> LOCATION: (1)..(2109)
<223> OTHER INFORMATION:

<400> SEQUENCE: 29

atg ccc tcg gct acc aac ggc acc atg gcg agc agc agc ggg aag gcg       48
```

-continued

```
Met Pro Ser Ala Thr Asn Gly Thr Met Ala Ser Ser Ser Gly Lys Ala
1               5                   10                  15

ggc ccg ggc ggc aac gag cag gcc ccg gcg gcg gca gcg gcg gcc ccg       96
Gly Pro Gly Gly Asn Glu Gln Ala Pro Ala Ala Ala Ala Ala Ala Pro
            20                  25                  30

cag gcg tcg ggc ggc agc atc acc tcg gtt cag acc gag gcc atg aag      144
Gln Ala Ser Gly Gly Ser Ile Thr Ser Val Gln Thr Glu Ala Met Lys
        35                  40                  45

cag atc ttg gga gtg atc gac aaa aag ctc cgc aac ctc gag aag aaa      192
Gln Ile Leu Gly Val Ile Asp Lys Lys Leu Arg Asn Leu Glu Lys Lys
    50                  55                  60

aag agc aaa ctt gac gat tac cag gaa cga atg aac aag ggg gaa cgt      240
Lys Ser Lys Leu Asp Asp Tyr Gln Glu Arg Met Asn Lys Gly Glu Arg
65                  70                  75                  80

cta aat caa gat caa ctg gat gca gtg tca aaa tac cag gaa gtg aca      288
Leu Asn Gln Asp Gln Leu Asp Ala Val Ser Lys Tyr Gln Glu Val Thr
                85                  90                  95

aat aac ctg gaa ttc gct aaa gaa ctg cag agg agc ttt atg gca ctg      336
Asn Asn Leu Glu Phe Ala Lys Glu Leu Gln Arg Ser Phe Met Ala Leu
            100                 105                 110

agc caa gat atc cag aaa aca ata aaa aag acg gct cgc agg gag cag      384
Ser Gln Asp Ile Gln Lys Thr Ile Lys Lys Thr Ala Arg Arg Glu Gln
        115                 120                 125

ctg atg aga gaa gag gct gag cag aag cgt tta aag act gtg cta gag      432
Leu Met Arg Glu Glu Ala Glu Gln Lys Arg Leu Lys Thr Val Leu Glu
    130                 135                 140

ctg cag ttc att ttg gac aag ttg ggt gac gat gaa gtg cgc agt gac      480
Leu Gln Phe Ile Leu Asp Lys Leu Gly Asp Asp Glu Val Arg Ser Asp
145                 150                 155                 160

ttg aaa caa gga tca aat gga gta ccg gta ctg aca gag gag gaa ctg      528
Leu Lys Gln Gly Ser Asn Gly Val Pro Val Leu Thr Glu Glu Glu Leu
                165                 170                 175

aca atg ctg gat gaa ttt tac aag cta gtt tac cct gaa agg gac atg      576
Thr Met Leu Asp Glu Phe Tyr Lys Leu Val Tyr Pro Glu Arg Asp Met
            180                 185                 190

aac atg agg ttg aat gag cag tat gag caa gca tct gtt cac ctg tgg      624
Asn Met Arg Leu Asn Glu Gln Tyr Glu Gln Ala Ser Val His Leu Trp
        195                 200                 205

gac tta ctg gaa ggg aag gaa aaa ccc gtt tgt gga aca acc tat aaa      672
Asp Leu Leu Glu Gly Lys Glu Lys Pro Val Cys Gly Thr Thr Tyr Lys
    210                 215                 220

gcc ctg aag gag gtt gtt gaa cgt att ctt caa act agt tac ttt gat      720
Ala Leu Lys Glu Val Val Glu Arg Ile Leu Gln Thr Ser Tyr Phe Asp
225                 230                 235                 240

agc acc cat aac cat cag aac ggg tta tgt gag gaa gaa gag gca gca      768
Ser Thr His Asn His Gln Asn Gly Leu Cys Glu Glu Glu Glu Ala Ala
                245                 250                 255

ccc aca cct gca gta gaa gac act gta gca gaa gct gag cct gat cca      816
Pro Thr Pro Ala Val Glu Asp Thr Val Ala Glu Ala Glu Pro Asp Pro
            260                 265                 270

gca gaa gaa ttt act gaa cct act gaa gtt gaa tcg act gag tat gta      864
Ala Glu Glu Phe Thr Glu Pro Thr Glu Val Glu Ser Thr Glu Tyr Val
        275                 280                 285

aac aga caa ttc atg gca gag act cag ttc agc agt agt gag aag gaa      912
Asn Arg Gln Phe Met Ala Glu Thr Gln Phe Ser Ser Ser Glu Lys Glu
    290                 295                 300

cag gta gat gag tgg aca gtt gaa acg gtt gag gtt gta aat tca ctg      960
Gln Val Asp Glu Trp Thr Val Glu Thr Val Glu Val Val Asn Ser Leu
305                 310                 315                 320

cag caa caa aca caa gct aca tct cct cca gtt cct gaa cct cat aca     1008
```

```
Gln Gln Gln Thr Gln Ala Thr Ser Pro Pro Val Pro Glu Pro His Thr
                325                 330                 335

ctc act act gtg gct caa gca gat cct ctt gtt aga aga cag aga gta      1056
Leu Thr Thr Val Ala Gln Ala Asp Pro Leu Val Arg Arg Gln Arg Val
            340                 345                 350

cag gac ctt atg gcc cag atg cag ggt cca tat aac ttc atg cag gac      1104
Gln Asp Leu Met Ala Gln Met Gln Gly Pro Tyr Asn Phe Met Gln Asp
        355                 360                 365

tct atg ctg gag ttt gag aac cag aca ctt gat cct gcc att gta tct      1152
Ser Met Leu Glu Phe Glu Asn Gln Thr Leu Asp Pro Ala Ile Val Ser
    370                 375                 380

gca cag ccc atg aat cca gca cag aat ttg gac atg ccg caa atg gtc      1200
Ala Gln Pro Met Asn Pro Ala Gln Asn Leu Asp Met Pro Gln Met Val
385                 390                 395                 400

tgc cct cca gtt cat act gag tca aga ctt gcc cag cct aat caa gtt      1248
Cys Pro Pro Val His Thr Glu Ser Arg Leu Ala Gln Pro Asn Gln Val
                405                 410                 415

cct gtg caa cca gaa gct acg cag gtt ccc ttg gtt tca tct aca agt      1296
Pro Val Gln Pro Glu Ala Thr Gln Val Pro Leu Val Ser Ser Thr Ser
            420                 425                 430

gag gga tat aca gcc tcc cag ccc atg tat cag cct tct cat acc aca      1344
Glu Gly Tyr Thr Ala Ser Gln Pro Met Tyr Gln Pro Ser His Thr Thr
        435                 440                 445

gag caa cgg cca cag aag gaa tcc att gac cag att cag gct tca atg      1392
Glu Gln Arg Pro Gln Lys Glu Ser Ile Asp Gln Ile Gln Ala Ser Met
    450                 455                 460

tca ctg aat gca gac cag acc ccg tca tca tca tca ctt ccc act gca      1440
Ser Leu Asn Ala Asp Gln Thr Pro Ser Ser Ser Ser Leu Pro Thr Ala
465                 470                 475                 480

tcc cag ccg caa gtt ttc caa gct gga tct agc aaa cct ttg cat agc      1488
Ser Gln Pro Gln Val Phe Gln Ala Gly Ser Ser Lys Pro Leu His Ser
                485                 490                 495

agc gga atc aat gtt aat gca gct cca ttc caa tcc atg caa aca gta      1536
Ser Gly Ile Asn Val Asn Ala Ala Pro Phe Gln Ser Met Gln Thr Val
            500                 505                 510

ttc aac atg aat gca cct gtt cct cct gtt aat gag cca gaa gcc ctt      1584
Phe Asn Met Asn Ala Pro Val Pro Pro Val Asn Glu Pro Glu Ala Leu
        515                 520                 525

aag caa caa aat cag tac cag gcc agt tac aac cag agt ttc tcc aat      1632
Lys Gln Gln Asn Gln Tyr Gln Ala Ser Tyr Asn Gln Ser Phe Ser Asn
    530                 535                 540

cag cca cac caa gta gaa caa tca gat ctt cag caa gaa cag ctc cag      1680
Gln Pro His Gln Val Glu Gln Ser Asp Leu Gln Gln Glu Gln Leu Gln
545                 550                 555                 560

aca gtg gtt ggt act tac cat ggt tct ccg gac cag acc cat caa gtg      1728
Thr Val Val Gly Thr Tyr His Gly Ser Pro Asp Gln Thr His Gln Val
                565                 570                 575

gca gga aac cac cag caa cct ccc cag cag aat act gga ttt cca cgc      1776
Ala Gly Asn His Gln Gln Pro Pro Gln Gln Asn Thr Gly Phe Pro Arg
            580                 585                 590

aac agt cag cct tat tac aac agt cgg gga gtg tct cgt ggt gga tca      1824
Asn Ser Gln Pro Tyr Tyr Asn Ser Arg Gly Val Ser Arg Gly Gly Ser
        595                 600                 605

cgt ggg act cgt gga ttg atg aat ggt tac agg gga cct gca aat gga      1872
Arg Gly Thr Arg Gly Leu Met Asn Gly Tyr Arg Gly Pro Ala Asn Gly
    610                 615                 620

ttt aga gga gga tat gat ggc tac cgt cct tca ttt tcc aac act ccg      1920
Phe Arg Gly Gly Tyr Asp Gly Tyr Arg Pro Ser Phe Ser Asn Thr Pro
625                 630                 635                 640

aac agt ggt tac acg cag ccc caa ttt aat gct cct cga gat tat tca      1968
```

```
Asn Ser Gly Tyr Thr Gln Pro Gln Phe Asn Ala Pro Arg Asp Tyr Ser
                645                 650                 655

aac tac cag cgg gat gga tat cag cag aac ttc aaa cgt ggt tct gga     2016
Asn Tyr Gln Arg Asp Gly Tyr Gln Gln Asn Phe Lys Arg Gly Ser Gly
            660                 665                 670

caa agt ggg cct cgg gga gct cct cga ggt cgt gga ggg ccc cca aga     2064
Gln Ser Gly Pro Arg Gly Ala Pro Arg Gly Arg Gly Gly Pro Pro Arg
        675                 680                 685

cca aac aga ggg atg cct caa atg aac gct cag caa gtg aat taa         2109
Pro Asn Arg Gly Met Pro Gln Met Asn Ala Gln Gln Val Asn
    690                 695                 700


<210> SEQ ID NO 30
<211> LENGTH: 702
<212> TYPE: PRT
<213> ORGANISM: Gallus gallus

<400> SEQUENCE: 30

Met Pro Ser Ala Thr Asn Gly Thr Met Ala Ser Ser Ser Gly Lys Ala
1               5                   10                  15

Gly Pro Gly Gly Asn Glu Gln Ala Pro Ala Ala Ala Ala Ala Ala Pro
            20                  25                  30

Gln Ala Ser Gly Gly Ser Ile Thr Ser Val Gln Thr Glu Ala Met Lys
        35                  40                  45

Gln Ile Leu Gly Val Ile Asp Lys Lys Leu Arg Asn Leu Glu Lys Lys
    50                  55                  60

Lys Ser Lys Leu Asp Asp Tyr Gln Glu Arg Met Asn Lys Gly Glu Arg
65                  70                  75                  80

Leu Asn Gln Asp Gln Leu Asp Ala Val Ser Lys Tyr Gln Glu Val Thr
                85                  90                  95

Asn Asn Leu Glu Phe Ala Lys Glu Leu Gln Arg Ser Phe Met Ala Leu
            100                 105                 110

Ser Gln Asp Ile Gln Lys Thr Ile Lys Lys Thr Ala Arg Arg Glu Gln
        115                 120                 125

Leu Met Arg Glu Glu Ala Glu Gln Lys Arg Leu Lys Thr Val Leu Glu
    130                 135                 140

Leu Gln Phe Ile Leu Asp Lys Leu Gly Asp Asp Glu Val Arg Ser Asp
145                 150                 155                 160

Leu Lys Gln Gly Ser Asn Gly Val Pro Val Leu Thr Glu Glu Glu Leu
                165                 170                 175

Thr Met Leu Asp Glu Phe Tyr Lys Leu Val Tyr Pro Glu Arg Asp Met
            180                 185                 190

Asn Met Arg Leu Asn Glu Gln Tyr Glu Gln Ala Ser Val His Leu Trp
        195                 200                 205

Asp Leu Leu Glu Gly Lys Glu Lys Pro Val Cys Gly Thr Thr Tyr Lys
    210                 215                 220

Ala Leu Lys Glu Val Val Glu Arg Ile Leu Gln Thr Ser Tyr Phe Asp
225                 230                 235                 240

Ser Thr His Asn His Gln Asn Gly Leu Cys Glu Glu Glu Glu Ala Ala
                245                 250                 255

Pro Thr Pro Ala Val Glu Asp Thr Val Ala Glu Ala Glu Pro Asp Pro
            260                 265                 270

Ala Glu Glu Phe Thr Glu Pro Thr Glu Val Glu Ser Thr Glu Tyr Val
        275                 280                 285

Asn Arg Gln Phe Met Ala Glu Thr Gln Phe Ser Ser Ser Glu Lys Glu
    290                 295                 300
```

```
Gln Val Asp Glu Trp Thr Val Glu Thr Val Glu Val Val Asn Ser Leu
305                 310                 315                 320

Gln Gln Gln Thr Gln Ala Thr Ser Pro Pro Val Pro Glu Pro His Thr
                325                 330                 335

Leu Thr Thr Val Ala Gln Ala Asp Pro Leu Val Arg Arg Gln Arg Val
            340                 345                 350

Gln Asp Leu Met Ala Gln Met Gln Gly Pro Tyr Asn Phe Met Gln Asp
        355                 360                 365

Ser Met Leu Glu Phe Glu Asn Gln Thr Leu Asp Pro Ala Ile Val Ser
    370                 375                 380

Ala Gln Pro Met Asn Pro Ala Gln Asn Leu Asp Met Pro Gln Met Val
385                 390                 395                 400

Cys Pro Pro Val His Thr Glu Ser Arg Leu Ala Gln Pro Asn Gln Val
                405                 410                 415

Pro Val Gln Pro Glu Ala Thr Gln Val Pro Leu Val Ser Ser Thr Ser
            420                 425                 430

Glu Gly Tyr Thr Ala Ser Gln Pro Met Tyr Gln Pro Ser His Thr Thr
        435                 440                 445

Glu Gln Arg Pro Gln Lys Glu Ser Ile Asp Gln Ile Gln Ala Ser Met
    450                 455                 460

Ser Leu Asn Ala Asp Gln Thr Pro Ser Ser Ser Ser Leu Pro Thr Ala
465                 470                 475                 480

Ser Gln Pro Gln Val Phe Gln Ala Gly Ser Ser Lys Pro Leu His Ser
                485                 490                 495

Ser Gly Ile Asn Val Asn Ala Ala Pro Phe Gln Ser Met Gln Thr Val
            500                 505                 510

Phe Asn Met Asn Ala Pro Val Pro Pro Val Asn Glu Pro Glu Ala Leu
        515                 520                 525

Lys Gln Gln Asn Gln Tyr Gln Ala Ser Tyr Asn Gln Ser Phe Ser Asn
    530                 535                 540

Gln Pro His Gln Val Glu Gln Ser Asp Leu Gln Gln Glu Gln Leu Gln
545                 550                 555                 560

Thr Val Val Gly Thr Tyr His Gly Ser Pro Asp Gln Thr His Gln Val
                565                 570                 575

Ala Gly Asn His Gln Gln Pro Pro Gln Gln Asn Thr Gly Phe Pro Arg
            580                 585                 590

Asn Ser Gln Pro Tyr Tyr Asn Ser Arg Gly Val Ser Arg Gly Gly Ser
        595                 600                 605

Arg Gly Thr Arg Gly Leu Met Asn Gly Tyr Arg Gly Pro Ala Asn Gly
    610                 615                 620

Phe Arg Gly Gly Tyr Asp Gly Tyr Arg Pro Ser Phe Ser Asn Thr Pro
625                 630                 635                 640

Asn Ser Gly Tyr Thr Gln Pro Gln Phe Asn Ala Pro Arg Asp Tyr Ser
                645                 650                 655

Asn Tyr Gln Arg Asp Gly Tyr Gln Gln Asn Phe Lys Arg Gly Ser Gly
            660                 665                 670

Gln Ser Gly Pro Arg Gly Ala Pro Arg Gly Arg Gly Gly Pro Pro Arg
        675                 680                 685

Pro Asn Arg Gly Met Pro Gln Met Asn Ala Gln Gln Val Asn
    690                 695                 700


<210> SEQ ID NO 31
<211> LENGTH: 20
<212> TYPE: DNA
<213> ORGANISM: Artificial
```

<220> FEATURE:
<223> OTHER INFORMATION: T3 primer

<400> SEQUENCE: 31
aattaaccct cactaaaggg 20

<210> SEQ ID NO 32
<211> LENGTH: 19
<212> TYPE: DNA
<213> ORGANISM: Artificial
<220> FEATURE:
<223> OTHER INFORMATION: T7 primer

<400> SEQUENCE: 32
taatacgact cactatagg 19

<210> SEQ ID NO 33
<211> LENGTH: 18
<212> TYPE: DNA
<213> ORGANISM: Artificial
<220> FEATURE:
<223> OTHER INFORMATION: primer

<400> SEQUENCE: 33
aaggtttgaa tggagtgc 18

<210> SEQ ID NO 34
<211> LENGTH: 18
<212> TYPE: DNA
<213> ORGANISM: Artificial
<220> FEATURE:
<223> OTHER INFORMATION: primer

<400> SEQUENCE: 34
tgctcctttt caccactg 18

<210> SEQ ID NO 35
<211> LENGTH: 18
<212> TYPE: DNA
<213> ORGANISM: Artificial
<220> FEATURE:
<223> OTHER INFORMATION: GAPDH primer

<400> SEQUENCE: 35
gggctgcttt taactctg 18

<210> SEQ ID NO 36
<211> LENGTH: 18
<212> TYPE: DNA
<213> ORGANISM: Artificial
<220> FEATURE:
<223> OTHER INFORMATION: GAPDH primer

<400> SEQUENCE: 36
ccaggaaatg agcttgac 18

<210> SEQ ID NO 37
<211> LENGTH: 22
<212> TYPE: DNA
<213> ORGANISM: Artificial
<220> FEATURE:
<223> OTHER INFORMATION: primer

<400> SEQUENCE: 37
aggtsharct gcagsagtcw gg 22

<210> SEQ ID NO 38
<211> LENGTH: 23
<212> TYPE: DNA
<213> ORGANISM: Artificial
<220> FEATURE:
<223> OTHER INFORMATION: primer

<400> SEQUENCE: 38
ctcgagttaa ttcacttgct gag 23

<210> SEQ ID NO 39
<211> LENGTH: 4
<212> TYPE: PRT
<213> ORGANISM: Gallus gallus

<400> SEQUENCE: 39

Phe Asp Met Gly
1

<210> SEQ ID NO 40
<211> LENGTH: 17
<212> TYPE: PRT
<213> ORGANISM: Gallus gallus

<400> SEQUENCE: 40

Gln Ile Asn Asp Ala Gly Ser Arg Thr Trp Tyr Ala Thr Ala Val Lys
1 5 10 15

Gly

<210> SEQ ID NO 41
<211> LENGTH: 12
<212> TYPE: PRT
<213> ORGANISM: Gallus gallus

<400> SEQUENCE: 41

Gly Ser Gly Tyr Val Gly Ala Gly Ala Ile Asp Ala
1 5 10

<210> SEQ ID NO 42
<211> LENGTH: 120
<212> TYPE: PRT
<213> ORGANISM: Gallus gallus

<400> SEQUENCE: 42

Ala Val Thr Leu Asp Glu Ser Gly Gly Gly Leu Gln Thr Pro Gly Gly
1 5 10 15

Gly Leu Ser Leu Val Cys Lys Ala Ser Gly Phe Thr Phe Ser Ser Phe
20 25 30

Asp Met Gly Trp Val Arg Gln Ala Pro Gly Lys Gly Leu Glu Phe Val
35 40 45

Ala Gln Ile Asn Asp Ala Gly Ser Arg Thr Trp Tyr Ala Thr Ala Val
50 55 60

Lys Gly Arg Ala Thr Ile Ser Arg Asp Asn Gly Gln Thr Thr Val Arg
65 70 75 80

Leu Gln Leu Asn Asn Leu Arg Ala Glu Asp Thr Gly Thr Tyr Tyr Cys
85 90 95

Thr Arg Gly Ser Gly Tyr Val Gly Ala Gly Ala Ile Asp Ala Trp Gly
100 105 110

His Gly Thr Glu Val Ile Val Ser
115 120

<210> SEQ ID NO 43

<211> LENGTH: 8
<212> TYPE: PRT
<213> ORGANISM: Gallus gallus

<400> SEQUENCE: 43

Ser Gly Gly Ser Gly Tyr Tyr Gly
1               5

<210> SEQ ID NO 44
<211> LENGTH: 7
<212> TYPE: PRT
<213> ORGANISM: Gallus gallus

<400> SEQUENCE: 44

Asn Asp Lys Arg Pro Ser Asp
1               5

<210> SEQ ID NO 45
<211> LENGTH: 10
<212> TYPE: PRT
<213> ORGANISM: Gallus gallus

<400> SEQUENCE: 45

Arg Tyr Asp Ser Thr Asp Ser Gly Ile Phe
1               5                   10

<210> SEQ ID NO 46
<211> LENGTH: 105
<212> TYPE: PRT
<213> ORGANISM: Gallus gallus

<400> SEQUENCE: 46

Ala Ala Leu Thr Gln Pro Ser Ser Val Ser Ala Asn Pro Gly Glu Thr
1               5                   10                  15

Val Lys Ile Thr Cys Ser Gly Gly Ser Gly Tyr Tyr Gly Trp Tyr Gln
            20                  25                  30

Gln Gln Lys Ser Pro Gly Ser Ala Pro Val Thr Val Ile Tyr Gln Asn
        35                  40                  45

Asp Lys Arg Pro Ser Asp Ile Pro Ser Arg Phe Ser Gly Ser Gly Ser
    50                  55                  60

Gly Ser Thr Asn Thr Leu Thr Ile Thr Gly Val Gln Ala Glu Asp Glu
65                  70                  75                  80

Ala Val Tyr Phe Cys Gly Arg Tyr Asp Ser Thr Asp Ser Gly Ile Phe
                85                  90                  95

Gly Ala Gly Thr Thr Leu Thr Val Leu
            100                 105

<210> SEQ ID NO 47
<211> LENGTH: 15
<212> TYPE: DNA
<213> ORGANISM: Artificial
<220> FEATURE:
<223> OTHER INFORMATION: primer

<400> SEQUENCE: 47
agtcacgacg ttgta                                                        15

<210> SEQ ID NO 48
<211> LENGTH: 17
<212> TYPE: DNA
<213> ORGANISM: Artificial
<220> FEATURE:
<223> OTHER INFORMATION: primer

<400> SEQUENCE: 48
caggaaacag ctatgac 17

<210> SEQ ID NO 49
<211> LENGTH: 363
<212> TYPE: DNA
<213> ORGANISM: Gallus gallus

<400> SEQUENCE: 49
gccgccgtga cgttggacga gtccgggggc ggcctccaga cgcccggagg agggctcagc 60
ctcgtctgca aggcctccgg gttcaccttc agcagtttcg acatgggttg ggtgcgacag 120
gcgcctggca aggggctgga attcgtcgct caaattaatg atgctggtag taggacatgg 180
tacgcgacag cggtgaaggg ccgtgccacc atctcgaggg acaacgggca gaccacagtg 240
aggctgcagc tgaacaacct cagggctgag gacaccggca cctactactg caccagaggt 300
agtggttatg ttggtgctgg tgcgatcgac gcatggggcc acgggaccga agtcatcgtg 360
tcg 363

<210> SEQ ID NO 50
<211> LENGTH: 315
<212> TYPE: DNA
<213> ORGANISM: Gallus gallus

<400> SEQUENCE: 50
gccgcgctga ctcagccgtc ctcggtgtca gcaaacccag gagaaaccgt caagatcacc 60
tgctccgggg gtagtggcta ctatggctgg taccagcagc agaagtctcc tggcagtgcc 120
cctgtcactg tgatctatca aaacgacaag agaccctcgg acatcccttc acgattctcc 180
ggttctggat caggctccac aaacacatta accatcactg gggtccaagc cgaggacgag 240
gctgtctatt tctgtggtcg ttacgacagc actgatagtg gtatatttgg ggccgggaca 300
accctgaccg tccta 315

<210> SEQ ID NO 51
<211> LENGTH: 240
<212> TYPE: DNA
<213> ORGANISM: Gallus gallus

<400> SEQUENCE: 51
accatgagcc cactcgtctc ctccctcctg ctcctggccg ccctgccagg tgagggcgct 60
gtggggctct atggggctct atggggtctc agcggggctc tgcgggctca atgggggcca 120
aagggggggt ctgcgggctc tatggggggg tcaacggggg gtctcacggg gggccggctc 180
cgcgaggccg tgtggcggcg gctccgtcag cgctttctgt ccttccccac agggcgcgcc 240

<210> SEQ ID NO 52
<211> LENGTH: 1807
<212> TYPE: DNA
<213> ORGANISM: Homo sapiens

<400> SEQUENCE: 52
ctttctgggg caggccaggc ctgaccttgg ctttggggca gggagggggc taaggtgagg 60
caggtggcgc cagccaggtg cacacccaat gcccatgagc ccagacactg gacgctgaac 120
ctcgcggaca gttaagaacc caggggcctc tgcgccctgg gcccagctct gtcccacacc 180
gcggtcacat ggcaccacct ctcttgcagc ctccaccaag ggcccatcgg tcttccccct 240
ggcaccctcc tccaagagca cctctggggg cacagcggcc ctgggctgcc tggtcaagga 300

```
ctacttcccc gaaccggtga cggtgtcgtg gaactcaggc gccctgacca gcggcgtgca    360
caccttcccg gctgtcctac agtcctcagg actctactcc ctcagcagcg tggtgaccgt    420
gccctccagc agcttgggca cccagaccta catctgcaac gtgaatcaca agcccagcaa    480
caccaaggtg gacaagaaag ttggtgagag gccagcacag ggagggaggg tgtctgctgg    540
aagccaggct cagcgctcct gcctggacgc atcccggcta tgcagcccca gtccagggca    600
gcaaggcagg ccccgtctgc ctcttcaccc ggaggcctct gcccgcccca ctcatgctca    660
gggagagggt cttctggctt tttccccagg ctctgggcag gcacaggcta ggtgccccta    720
acccaggccc tgcacacaaa ggggcaggtg ctgggctcag acctgccaag agccatatcc    780
gggaggaccc tgcccctgac ctaagcccac cccaaaggcc aaactctcca ctccctcagc    840
tcggacacct tctctcctcc cagattccag taactcccaa tcttctctct gcagagccca    900
aatcttgtga caaaactcac acatgcccac cgtgcccagg taagccagcc caggcctcgc    960
cctccagctc aaggcgggac aggtgcccta gagtagcctg catccaggga caggccccag   1020
ccgggtgctg acacgtccac ctccatctct tcctcagcac ctgaactcct ggggggaccg   1080
tcagtcttcc tcttcccccc aaaacccaag gacaccctca tgatctcccg gacccctgag   1140
gtcacatgcg tggtggtgga cgtgagccac gaagaccctg aggtcaagtt caactggtac   1200
gtggacggcg tggaggtgca taatgccaag acaaagccgc gggaggagca gtacaacagc   1260
acgtaccgtg tggtcagcgt cctcaccgtc ctgcaccagg actggctgaa tggcaaggag   1320
tacaagtgca aggtctccaa caaagccctc ccagccccca tcgagaaaac catctccaaa   1380
gccaaaggtg ggacccgtgg ggtgcgaggg ccacatggac agaggccggc tcggcccacc   1440
ctctgccctg agagtgaccg ctgtaccaac ctctgtccct acagggcagc cccgagaacc   1500
acaggtgtac accctgcccc catcccggga tgagctgacc aagaaccagg tcagcctgac   1560
ctgcctggtc aaaggcttct atcccagcga catcgccgtg gagtgggaga gcaatgggca   1620
gccggagaac aactacaaga ccacgcctcc cgtgctggac tccgacggct ccttcttcct   1680
ctacagcaag ctcaccgtgg acaagagcag gtggcagcag gggaacgtct tctcatgctc   1740
cgtgatgcat gaggctctgc acaaccacta cacgcagaag agcctctccc tgtctccggg   1800
taaatga                                                               1807
```

<210> SEQ ID NO 53
<211> LENGTH: 567
<212> TYPE: DNA
<213> ORGANISM: Homo sapiens

<400> SEQUENCE: 53

```
cagaatggct gcaaagagct ccaacaaaac aatttagaac tttattaagg aataggggga     60
agctaggaag aaactcaaaa catcaagatt ttaaatacgc ttcttggtct ccttgctata    120
attatctggg ataagcatgc tgttttctgt ctgtccctaa catgccctgt gattatccgc    180
aaacaacaca cccaagggca gaactttgtt acttaaacac catcctgttt gcttctttcc    240
tcaggaactg tggctgcacc atctgtcttc atcttcccgc catctgatga gcagttgaaa    300
tctggaactg cctctgttgt gtgcctgctg aataacttct atcccagaga ggccaaagta    360
cagtggaagg tggataacgc cctccaatcg ggtaactccc aggagagtgt cacagagcag    420
gacagcaagg acagcaccta cagcctcagc agcaccctga cgctgagcaa agcagactac    480
gagaaacaca aagtctacgc ctgcgaagtc acccatcagg gcctgagctc gcccgtcaca    540
aagagcttca acaggggaga gtgttag                                        567
```

PHARMACEUTICAL COMPOSITION FOR TREATING CAPRIN-1 EXPRESSING CANCER

TECHNICAL FIELD

The present invention relates to a novel pharmaceutical use of an antibody against CAPRIN-1 or a fragment thereof, as an agent, for treating and/or preventing a cancer.

BACKGROUND ART

Cancer is the leading cause of death. Currently conducted therapy comprises mainly surgical therapy in combination with radiation therapy and chemotherapy. In spite of the development of new operative procedures and the discovery of new anticancer agents in recent years, cancer treatment results have not been much improved recently, excluding that for some types of cancer. Recent advances in molecular biology or cancer immunology lead to identification of antibodies specifically reacting with cancer, cancer antigens to be recognized by cytotoxic T cells, genes encoding cancer antigens, and the like. Demands on specific cancer therapies targeting cancer antigens are increasing (Non-patent Literature 1).

In cancer therapy, it is desirable that peptides, polypeptides, or proteins recognized as antigens be almost absent in normal cells, but they be present specifically in cancer cells, in order to alleviate side effects. In 1991, Boon et al., (Ludwig Institute for Cancer Research, Belgium) isolated a human melanoma antigen MAGE1 recognized by CD8-positive T cells by the cDNA expression cloning method using autologous cancer cell lines and cancer-reactive T cells (Non-patent Literature 2). Thereafter, the SEREX (serological identification of antigens by recombinant expression cloning) method that comprises identifying tumor antigens recognized by antibodies that are produced in vivo in response to autologous cancer of a cancer patient by gene expression cloning techniques was reported (Non-patent Literature 3 and Patent Literature 1). With the use of this method, some cancer antigens, which are almost never expressed in normal cells but are specifically expressed in cancer cells, were isolated (Non-patent Literatures 4-9). Furthermore, clinical trials were conducted with cell therapies targeting some cancer antigens using immunocytes specifically reactive with cancer antigens, or cancer-specific immunotherapies using vaccines or the like containing cancer antigens.

Meanwhile, in recent years, various antibody medicines which target antigenic proteins on cancer cells for cancer treatment have appeared throughout the world. Antibody medicines exhibit some pharmacological effects as cancer specific therapeutic agents and are thus attracting attention. However, most antigen proteins to be targeted are also expressed in normal cells, so that not only cancer cells, but also normal cells expressing antigens are also damaged as a result of antibody administration. The resulting side effects cause for concern. Therefore, it is expected that identification of cancer antigens that are specifically expressed on the surface of a cancer cell and use of antibodies targeting the cancer antigens as pharmaceuticals will realize treatment with antibody medicines with lower side effects.

Cytoplasmic- and proliferation-associated protein 1 (CAPRIN-1) is expressed when normal cells at the resting phase are activated or undergo cell division, and it is an intracellular protein known to form intracellular stress granules with RNA within cells, so as to be involved in mRNA transport and translational regulation. Meanwhile, many other names that represent CAPRIN-1 exist, such as GPI-anchored membrane protein 1 or membrane component surface marker 1 protein (M11S1), as if such proteins had been known to be cell membrane proteins. These names originated from a report that the gene sequence of CAPRIN-1 is a membrane protein having a GPI-binding region and expressed in colorectal cancer cells (Non-patent Literature 10). However, the gene sequence of CAPRIN-1 provided in this report was later revealed to be wrong. The following has recently been reported; i.e., deletion of a single nucleotide in the gene sequence of CAPRIN-1 registered at GenBank or the like causes a frame shift, so that 80 amino acids are lost from the C-terminus, resulting in generation of an artifact (74 amino acids) which corresponds to the GPI-binding portion in the previous report, and additionally, another error is also present 5' of the gene sequence, so that 53 amino acids were lost from the N-terminus (Non-patent Literature 11). It has been also recently reported that the protein encoded by the gene sequence of CAPRIN-1 registered at GenBank or the like is not a cell membrane protein (Non-patent Literature 11).

In addition, on the basis of the report of Non-patent Literature 10 that CAPRIN-1 is a cell membrane protein, Patent Literatures 2 and 3 describe that CAPRIN-1 (as a cell membrane protein) under the name of M11S1 can be used as a target of an antibody medicine in cancer therapy, although working examples do not describe treatment using an antibody against the protein. However, as reported in Non-patent Literature 11, it has been commonly believed from the time of the filing of Patent Literature 2 to date that CAPRIN-1 is not expressed on the surface of a cell. The contents of Patent Literatures 2 and 3 based only on incorrect information that CAPRIN-1 is a cell membrane protein should not clearly be understood as common general knowledge for persons skilled in the art.

PRIOR ART LITERATURE

Patent Literature

Patent Literature 1: U.S. Pat. No. 5,698,396

Patent Literature 2: US2008/0075722

Patent Literature 3: WO2005/100998

Non-Patent Literature

Non-patent Literature 1: Tsuyoshi Akiyoshi, "Gan To Kagaku-Ryoho (Cancer and Chemotherapy)," 1997, Vol. 24, p 551-519 (Cancer and Chemotherapy Publishers, Inc., Japan)

Non-patent Literature 2: Bruggen P. et al., Science, 254: 1643-1647 (1991)

Non-patent Literature 3: Proc. Natl. Acad. Sci. U.S.A, 92: 11810-11813 (1995)

Non-patent Literature 4: Int. J. Cancer, 72: 965-971 (1997)

Non-patent Literature 5: Cancer Res., 58: 1034-1041 (1998)

Non-patent Literature 6: Int. J. Cancer, 29: 652-658 (1998)

Non-patent Literature 7: Int. J. Oncol., 14: 703-708 (1999)

Non-patent Literature 8: Cancer Res., 56: 4766-4772 (1996)

Non-patent Literature 9: Hum. Mol. Genet 6: 33-39, 1997

Non-patent Literature 10: J. Biol. Chem., 270: 20717-20723, 1995

Non-patent Literature 11: J. Immunol., 172: 2389-2400, 2004

SUMMARY OF THE INVENTION

Problem to be Solved by the Invention

Objects of the present invention are to identify a cancer antigen protein specifically expressed on the surface of a cancer cell and to provide the use of an antibody targeting the cancer antigen protein as an agent for treating and/or preventing a cancer.

Means for Solving the Problem

As a result of intensive studies, the present inventors have now obtained a cDNA encoding a protein that binds to an antibody existing in sera from dogs with breast cancer by the SEREX method using both cDNA libraries prepared from dog testis tissues and sera of dogs with breast cancer. The present inventors have now further prepared CAPRIN-1 proteins having the even-numbered amino acid sequences of SEQ ID NOS: 2 to 30 and antibodies against such CAPRIN-1 proteins based on the obtained dog gene and the corresponding human, cattle, horse, mouse, and chicken homologous genes. Thus, the present inventors have now found that CAPRIN-1 is specifically expressed in breast cancer, brain tumor, leukemia, lymphoma, lung cancer, uterine cervix cancer, bladder cancer, esophageal cancer, colorectal cancer, gastric cancer, and renal cancer cells, and that a portion of the CAPRIN-1 protein is specifically expressed on the surface of each cancer cell. The present inventors have thus now found that an antibody or antibodies against the portion of CAPRIN-1 expressed on the surface of each cancer cell is/are cytotoxic to the CAPRIN-1-expressing cancer cells. On the basis of these findings, the present invention as described below was completed.

The present invention has the following characteristics.

The present invention provides a pharmaceutical composition for treating and/or preventing a cancer, comprising an antibody that comprises a heavy chain variable region comprising SEQ ID NO: 39, 40, and 41 and a light chain variable region comprising SEQ ID NO: 43, 44, and 45 or a fragment thereof as an active ingredient and having immunological reactivity with a CAPRIN-1 protein.

In an embodiment, the above cancer is breast cancer, brain tumor, leukemia, lymphoma, lung cancer, uterine cervix cancer, bladder cancer, esophageal cancer, colorectal cancer, gastric cancer, or renal cancer.

In another embodiment, the above antibody is a human antibody, humanized antibody, chimeric antibody, single chain antibody, or bispecific antibody.

This description includes part or all of the contents as disclosed in the description and/or drawings of Japanese Patent Application No. 2010-023452, which is a priority literature of the present application.

Effects of the Invention

The antibody against CAPRIN-1 used in the present invention is cytotoxic to cancer cells. As such, the antibody against CAPRIN-1 is useful for treating or preventing cancers.

MODE FOR CARRYING OUT THE INVENTION

Figure 1:
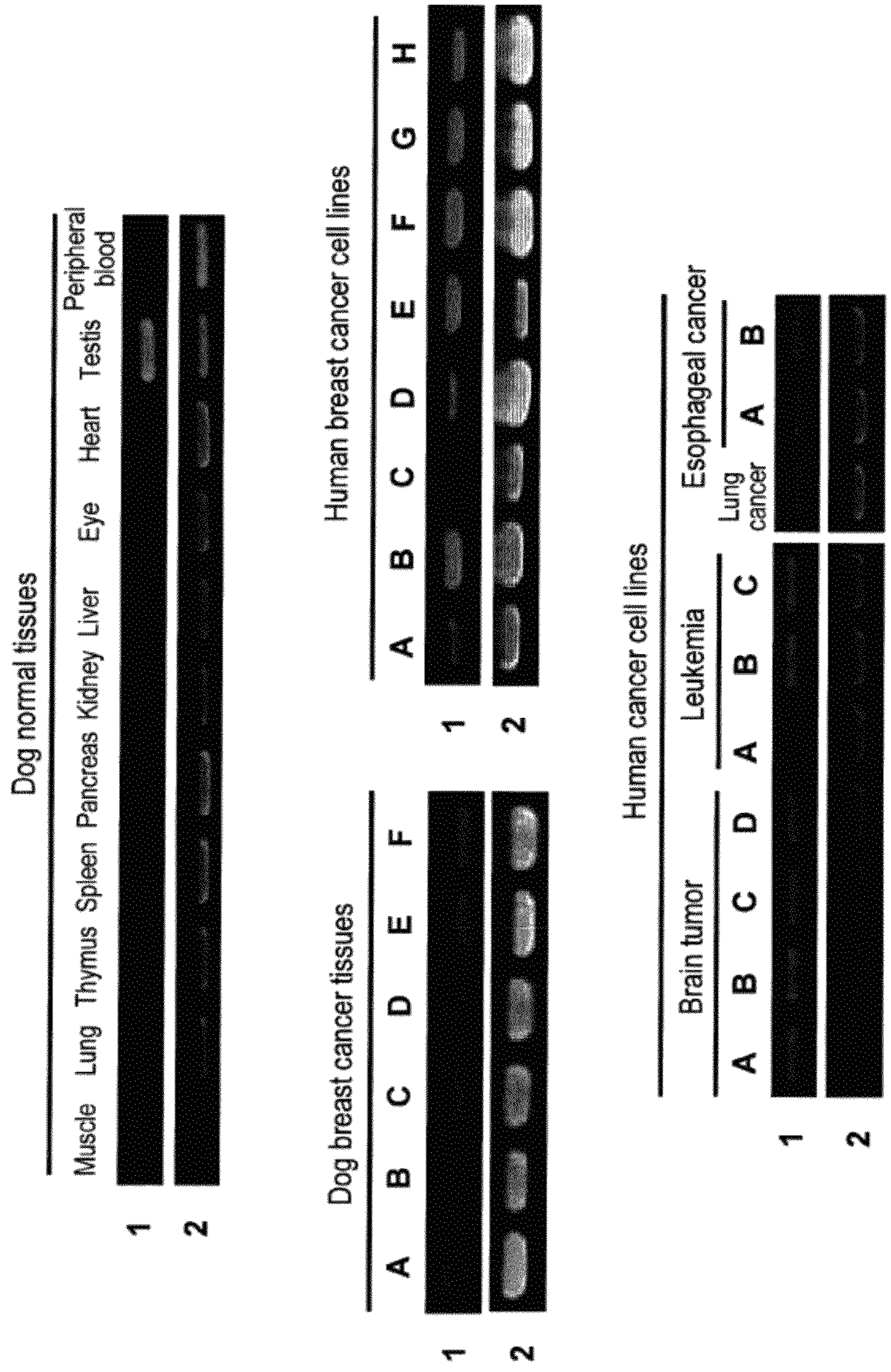
FIG. 1 shows the expression patterns of genes encoding CAPRIN-1 proteins in normal tissues and tumor cell lines. Reference No. 1 indicates the expression patterns of genes encoding CAPRIN-1 proteins, and Reference No. 2 indicates the expression patterns of GAPDH genes.

The anti-tumor activity of an antibody against a polypeptide represented by any of the even-numbered sequences of SEQ ID NOS: 2 to 30 used in the present invention can be evaluated by examining in vivo suppression of tumor growth in animals with cancer, or, examining whether or not the antibody exhibits cytotoxicity via immunocytes or complements to tumor cells expressing the polypeptide in vitro, as described later.

In the context, the nucleotide sequences of polynucleotides encoding proteins comprising the even-numbered amino acid sequences (i.e., SEQ ID NOS: 2, 4, 6 . . . 28, 30) of SEQ ID NOS: 2 to 30 are represented by the odd-numbered sequences (i.e., SEQ ID NOS: 1, 3, 5 . . . 27, 29) of SEQ ID NOS: 1 to 29.

The amino acid sequences that are represented by SEQ ID NOS: 6, 8, 10, 12, and 14 in the Sequence Listing disclosed herein are the amino acid sequences of CAPRIN-1 isolated as polypeptides, which bind to antibodies specifically existing in serum from a dog with cancer, through the SEREX method using a cDNA library from dog testis tissue and the serum of a dog with breast cancer. The amino acid sequences represented by SEQ ID NOS: 2 and 4 are the amino acid sequences of CAPRIN-1 isolated as human homologues. The amino acid sequence represented by SEQ ID NO: 16 is the amino acid sequence of CAPRIN-1 isolated as a cattle homologue. The amino acid sequence represented by SEQ ID NO: 18 is the amino acid sequence of CAPRIN-1 isolated as a horse homologue. The amino acid sequences represented by SEQ ID NOS: 20 to 28 are the amino acid sequences of CAPRIN-1 isolated as mouse homologues. The amino acid sequence represented by SEQ ID NO: 30 is the amino acid sequence of CAPRIN-1 isolated as a chicken homologue (see Example 1 described later). CAPRIN-1 is known to be expressed when normal cells in the resting phase are activated or give rise to cell division.

It was known that CAPRIN-1 was not expressed on cell surfaces. However, as a result of the examination by the present inventors, it has now been revealed that a portion of the CAPRIN-1 protein is expressed on the surfaces of various cancer cells. It has thus been revealed that an antibody having immunological reactivity with a partial region of a CAPRIN-1 protein that is expressed on cancer cell surfaces or specifically recognizing the region (that is, specifically binding to the region) and comprising a heavy chain variable region that comprises SEQ ID NO: 39, 40, and 41 and a light chain variable region that comprises SEQ ID NO: 43, 44, and 45 exhibits anti-tumor activity.

The above-described anti-CAPRIN-1 antibody used in the present invention may be any type of monoclonal antibody as long as it can exhibit anti-tumor activity. Examples of such an antibody include recombinant antibodies, such as a synthetic antibody, a multispecific antibody, a humanized antibody, a chimeric antibody, and a single chain antibody (scFv), a human antibody, and antibody fragments thereof, such as Fab, F(ab')$_2$, and Fv. These antibodies and fragments thereof can be prepared by methods known by persons skilled in the art. Also, when a subject is a human, human antibodies or humanized antibodies are desired in order to avoid or suppress rejection.

The term "specifically binding to a partial region of a CAPRIN-1 protein" as used herein means that "the antibody specifically binds to a specific region of a CAPRIN-1 protein without substantially binding to protein portions other than such a region."

The anti-tumor activity of an antibody that can be used in the present invention can be evaluated as described below by examining in vivo the suppression of the tumor growth in animals with cancer, or, by examining whether or not it exhibits in vitro an activity of cytotoxicity, which is mediated by immunocytes or complements, to tumor cells expressing the polypeptide.

Furthermore, examples of the subject for cancer treatment and/or prevention in the present invention include mammals, such as humans, pet animals, domestic animals, and animals for competition. A preferable subject is a human.

Preparation of antigens and antibodies and pharmaceutical compositions relating to the present invention are described below.

<Preparation of Antigens for Antibody Preparation>

Proteins or fragments thereof to be used as sensitizing antigens for obtaining anti-CAPRIN-1 antibodies used in the present invention may be derived from any animal species without particular limitation, such as humans, dogs, cattle, horses, mice, rats, and chickens. However, proteins or fragments thereof are preferably selected in consideration of compatibility with parent cells used for cell fusion. In general, mammal-derived proteins are preferred and, in particular, human-derived protein is preferred. For example, when CAPRIN-1 is human CAPRIN-1, the human CAPRIN-1 protein, a partial peptide thereof, or cells expressing human CAPRIN-1 can be used.

The nucleotide sequences and the amino acid sequences of human CAPRIN-1 and homologues thereof can be obtained by accessing GenBank (NCBI, U.S.A.) and using an algorithm such as BLAST or FASTA (Karlin and Altschul, Proc. Natl. Acad. Sci. U.S.A., 90: 5873-5877, 1993; Altschul et al., Nucleic Acids Res. 25: 3389-3402, 1997).

In the present invention, on the basis of the nucleotide sequence (SEQ ID NO: 1 or 3) or the amino acid sequence (SEQ ID NO: 2 or 4) of human CAPRIN-1, a target nucleic acid or a target protein comprises a sequence having 70% to 100%, preferably 80% to 100%, more preferably 90% to 100%, even more preferably 95% to 100% (e.g., 97% to 100%, 98% to 100%, 99% to 100%, or 99.5% to 100%) sequence identity with the nucleotide sequence or the amino acid sequence of the ORF or the mature portion of human CAPRIN-1. As use herein, the term "% sequence identity" refers to a percentage (%) of identical amino acids (or nucleotides) relative to the total number of amino acids (or nucleotides), when two sequences are aligned to achieve the highest similarity with or without introduction of gaps.

The length of a fragment of CAPRIN-1 protein ranges from the amino acid length of an epitope (antigenic determinant), which is the minimum unit recognized by an antibody, to a length less than the full length of the protein. The term "epitope" refers to a polypeptide fragment having antigenicity or immunogenicity in mammals, preferably in humans, and the minimum unit of the epitope consists of about 7 to 12 amino acids (e.g., 8 to 11 amino acids).

The polypeptides comprising the above-mentioned human CAPRIN-1 protein or partial peptides of the protein, can be synthesized by a chemical synthesis method, such as the Fmoc method (fluorenylmethyloxycarbonyl method) or the tBoc method (t-butyloxycarbonyl method) (Edited by The Japanese Biochemical Society, Seikagaku Jikken Koza (Biochemical Experimental Lecture Series) 1, Protein Chemistry IV, Chemical Modification and Peptide Synthesis, TOKYO KAGAKU DOZIN (Japan), 1981). Alternatively, the above-mentioned polypeptides may also be synthesized by conventional methods using various commercially available peptide synthesizers. Furthermore, with the use of known genetic engineering techniques (e.g., Sambrook et al., Molecular Cloning, 2$^{nd}$ Edition, Current Protocols in Molecular Biology (1989), Cold Spring Harbor Laboratory Press, Ausubel et al., Short Protocols in Molecular Biology, 3$^{rd}$ Edition, A compendium of Methods from Current Protocols in Molecular Biology (1995), John Wiley & Sons), a polynucleotide encoding the above polypeptide is prepared and then incorporated into an expression vector, which is subsequently introduced into a host cell in order to produce a polypeptide of interest in the host cell, and then recover it.

The polynucleotides encoding the above polypeptides can be easily prepared by known genetic engineering techniques or conventional techniques using a commercially available nucleic acid synthesizer. For example, DNA comprising the nucleotide sequence of SEQ ID NO: 1 can be prepared by PCR using a human chromosomal DNA or cDNA library, as a template, and a pair of primers designed to be able to amplify the nucleotide sequence represented by SEQ ID NO: 1. PCR conditions can be appropriately determined. For example, PCR conditions comprise conducting 30 cycles of the reaction cycle of: denaturation at 94° C. for 30 seconds; annealing at 55° C. for 30 seconds to 1 minute; and extension at 72° C. for 2 minutes, using a thermostable DNA polymerase (e.g., Taq polymerase or Pfu polymerase) and PCR buffer containing $Mg^{2+}$, followed by reacting at 72° C. for 7 minutes. However, the PCR conditions are not limited to the above example. PCR techniques, conditions, and the like are described in Ausubel et al., Short Protocols in Molecular Biology, 3$^{rd}$ Edition, A compendium of Methods from Current Protocols in Molecular Biology (1995), John Wiley & Sons (particularly Chapter 15).

Also, on the basis of the nucleotide sequence and amino acid sequence information represented by SEQ ID NOS: 1 to 30 in the Sequence Listing described herein, appropriate probes or primers are prepared, and then a cDNA library of a human or the like is screened using them, so that desired DNA can be isolated. A cDNA library is preferably constructed from cells, organs or tissues, which express proteins having even-numbered sequences of SEQ ID NOS: 2 to 30. Examples of such cells or tissues include cells or tissues derived from testis, and cancers or tumors, such as leukemia, breast cancer, lymphoma, brain tumor, lung cancer, colorectal cancer, and the like. Procedures such as the preparation of probes or primers, construction of a cDNA library, screening of a cDNA library, and cloning of target genes are known by a person skilled in the art and can be carried out by the methods described in Sambrook et al., Molecular Cloning, 2nd Edition, Current Protocols in Molecular Biology (1989), Ausbel et al., (above), and the like. DNA encoding a human CAPRIN-1 protein or a partial peptide thereof can be obtained from the thus obtained DNA.

The host cells may be any cells, as long as they can express the above-mentioned polypeptide. Examples of prokaryotic cells include, but are not limited to, *Escherichia coli* and the like. Examples of eukaryotic cells include, but are not limited to, mammalian cells, such as monkey kidney cells (COS1) and Chinese hamster ovary cells (CHO), human fetal kidney cell line (HEK293), fetal mouse skin cell line (NIH3T3), yeast cells such as budding yeast and fission yeast, silkworm cells, and *Xenopus* oocyte.

When prokaryotic cells are used as host cells, an expression vector used herein contains an origin replicable within prokaryotic cells, a promoter, a ribosome-binding site, a multiple cloning site, a terminator, a drug resistance gene, an auxotrophic complementary gene, and the like. Examples of *Escherichia coli* expression vector include a pUC-based vector, pBluescript II, a pET expression system, and a pGEX expression system. DNA encoding the above polypeptide is incorporated into such an expression vector, prokaryotic host cells are transformed with the vector, the thus obtained transformed cells are cultured, and thus the polypeptide encoded by the DNA can be expressed in prokaryotic host cells. At this time, the polypeptide can also be expressed as a fusion protein with another protein.

When eukaryotic cells are used as host cells, an expression vector used herein is an expression vector for eukaryotic cells, which contains a promoter, a splicing region, a poly(A) addition site, and the like. Examples of such an expression vector include pKA1, pCDM8, pSVK3, pMSG, pSVL, pBK-CMV, pBK-RSV, EBV vector, pRS, pcDNA3, and pYES2. In a manner similar to the above, DNA encoding the above polypeptide is incorporated into such an expression vector, eukaryotic host cells are transformed with the vector, the thus obtained transformed cells are cultured, and thus the polypeptide encoded by the DNA can be expressed in eukaryotic host cells. When pIND/V5-His, pFLAG-CMV-2, pEGFP-N1, pEGFP-C1, or the like is used as an expression vector, the above polypeptide can be expressed as a fusion protein to which a tag from among various tags such as a His tag (e.g., $(His)_6$-$(His)_{10}$), a FLAG tag, a myc tag, an HA tag, and GFP has been added.

For introduction of an expression vector into host cells, a known method can be employed, such as electroporation, a calcium phosphate method, a liposome method, a DEAE dextran method, microinjection, viral infection, lipofection, and binding to a cell membrane-permeable peptide.

The polypeptide of interest can be isolated and purified from host cells by a combination of known separation procedures. Examples of such procedures include, but are not limited to, treatment with a denaturing agent such as urea or a surfactant, ultrasonication, enzymatic digestion, salting-out or solvent fractionation and precipitation, dialysis, centrifugation, ultrafiltration, gel filtration, SDS-PAGE, isoelectric focusing, ion exchange chromatography, hydrophobic chromatography, affinity chromatography, and reverse phase chromatography.

<Antibody Structure>

An antibody is a heteromultimeric glycoprotein that generally contains at least two heavy chains and two light chains. Antibodies other than IgM is an about 150-kDa hetero tetramer glycoprotein composed of two identical light (L) chains and two identical heavy (H) chains. Typically, each light chain is connected to a heavy chain via one disulfide covalent bond, however, the number of disulfide bonds between heavy chains of various immunoglobulin isotypes is varied. Each heavy chain or each light chain also has an intrachain disulfide bond. Each heavy chain has a variable domain (VH region) on one end followed by several constant regions. Each light chain has a variable domain (VL region) and has one constant region on an end opposite to the other end. The constant region of a light chain is aligned with the first constant region of a heavy chain, and a light chain variable domain is aligned with a heavy chain variable domain. A specific region of an antibody variable domain exhibits specific variability that is referred to as a complementarity determining region (CDR), so that it imparts binding specificity to the antibody. A portion of a variable region, which is relatively conserved, is referred to as a framework region (FR). Complete heavy chain and light chain variable domains separately contains four FRs ligated via three CDRs. The three CDRs in a heavy chain are referred to as CDRH1, CDRH2, and CDRH3 in this order from the N-terminus. Similarly, in the case of a light chain, CDRLs are referred to as CDRL1, CDRL2, and CDRL3. CDRH3 is most important for the binding specificity of an antibody to an antigen. Also, the CDRs of each chain are retained together in a state of being adjacent to each other due to the FR regions, contributing to the formation of the antigen binding site of the antibody together with CDRs from the other chain. A constant region does not directly contribute to the binding of an antibody to an antigen, but exhibits various effector functions, such as involvement in antibody-dependent cell-mediated cytotoxicity (ADCC), phagocytosis via binding to an Fcγ receptor, the rate of half-life/clearance via a neonate Fc receptor (FcRn), and complement-dependent cytotoxicity (CDC) via a C1q constituent of the complement cascade.

<Preparation of Antibody>

The term "anti-CAPRIN-1 antibody" as used herein refers to an antibody having immunological reactivity with a full-length CAPRIN-1 protein or a fragment thereof.

As used herein, the term "immunological reactivity" refers to the property of in vivo binding of an antibody to a CAPRIN-1 antigen. Through such an in vivo binding, the function of damaging tumor (e.g., death, suppression, or degeneration) is exhibited. Specifically, an antibody used in the present invention may be any type of antibody, as long as it binds to a CAPRIN-1 protein so as to be able to damage tumor, such as leukemia, lymphoma, breast cancer, brain tumor, lung cancer, bladder cancer, uterine cervix cancer, esophageal cancer, gastric cancer, renal cancer, or colorectal cancer.

In the present invention, examples of an antibody include, but are not particularly limited to, as long as it is a monoclonal antibody, a synthetic antibody, a multispecific antibody, a human antibody, a humanized antibody, a chimeric antibody, a single chain antibody, and an antibody fragment (e.g., Fab and $F(ab')_2$). Also, an antibody may be an immunoglobulin molecule of any class such as IgG, IgE, IgM, IgA, IgD, and IgY, or any subclass such as IgG1, IgG2, IgG3, IgG4, IgA1, and IgA2.

The antibody may further be modified by, in addition to glycosylation, acetylation, formylation, amidation, phosphorylation, pegylation (PEG), or the like.

Preparation examples of various monoclonal antibodies are as described below.

When the antibody is a monoclonal antibody, for example, the breast cancer cell line SK-BR-3 expressing CAPRIN-1 is administered to a mouse for immunization, the spleen is removed from the mouse, cells are separated, and then the cells and mouse myeloma cells are fused. From among the thus obtained fusion cells (hybridomas), a clone producing an antibody having the effect of suppressing cancer cell proliferation is selected. A hybridoma producing a monoclonal antibody that has the effect of suppressing cancer cell proliferation is isolated, the hybridoma is cultured, and then an antibody is purified from the culture supernatant by general affinity purification, so that the antibody can be prepared.

The hybridoma producing a monoclonal antibody can also be prepared as described below, for example. First, an animal is immunized with a sensitizing antigen according to a known method. A general method is carried out by injecting a sensitizing antigen to a mammal intraperitoneally or subcutaneously. Specifically, a sensitizing antigen is diluted with PBS (Phosphate-Buffered Saline), saline, or the like to an appropriate amount, followed by suspension. The resultant is then mixed with an appropriate amount of a general adjuvant as necessary, such as Freund's complete adjuvant. After emulsification, the solution was administered to a mammal several times every 4 to 21 days. Furthermore, an appropriate carrier can also be used upon immunization with a sensitizing antigen.

A mammal is immunized as described above. After confirmation of a rise in a desired serum antibody level, immunized cells are collected from the mammal and then subjected to cell fusion. Preferable immunized cells are particularly splenocytes.

Mammalian myeloma cells are used as the other parent cells to be fused with the immunized cells. As the myeloma cells, various known cell lines are preferably used, such as P3U1 (P3-X63Ag8U1), P3 (P3x63Ag8. 653) (J. Immunol. (1979) 123, 1548-1550), P3x63Ag8U.1 (Current Topics in Microbiology and Immunology (1978) 81, 1-7), NS-1 (Kohler. G. and Milstein, C. Eur. J. Immunol. (1976) 6, 511-519), MPC-11 (Margulies. D. H. et al., Cell (1976) 8, 405-415), SP2/0 (Shulman, M. et al., Nature (1978) 276, 269-270), FO (deSt. Groth, S. F. et al., J. Immunol. Methods (1980) 35, 1-21), S194 (Trowbridge, I. S. J. Exp. Med. (1978) 148, 313-323), and R210 (Galfre, G. et al., Nature (1979) 277, 131-133).

Fusion of the immunized cell and the myeloma cell can be carried out according to basically a known method such as Kohler and Milstein's technique (Kohler, G. and Milstein, C. Methods Enzymol. (1981) 73, 3-46), for example.

More specifically, the above cell fusion is carried out, for example, in the presence of a cell fusion accelerator in a usual nutrient culture medium. As this fusion accelerator, polyethyleneglycol (PEG), Sendai virus (HVJ), or the like is used. If desired, an auxiliary agent such as dimethylsulfoxide may be added and used in order to enhance fusion efficiency.

The ratio of the immunized cells to the myeloma cells to be used herein can be arbitrarily set. For example, the number of immunized cells that are preferably used is one to ten times the number of myeloma cells. As a culture medium to be used for the above-mentioned cell fusion, an RPMI1640 culture medium suitable for proliferation of the above-mentioned myeloma cell line, an MEM culture medium, and other culture media usually used for culturing this kind of cell can be used. Further, liquid that is supplemental to serum such as fetal bovine serum (FCS) can be used together therewith.

Cell fusion can be performed by thoroughly mixing the predetermined amounts of the above immunized cells and the myeloma cells in the above culture medium, and a PEG solution (for example, having an average molecular weight ranging from about 1000 to 6000) prewarmed at about 37° C. is added usually at a concentration of 30%-60% (w/v) and mixed, thereby forming a culture containing hybridomas of interest. Next, a suitable culture medium is successively added to the thus-obtained culture, which is then centrifuged to remove the supernatant, and this procedure is repeated to remove the cell fusion agent or the like which is not preferable for the growth of hybridomas.

The thus obtained hybridomas are cultured for selection in a usual selection culture medium (e.g., a HAT culture medium containing hypoxanthine, aminopterin and thymidine). Culturing in this HAT culture medium is continued for a sufficient period of time (usually several days to several weeks) so that the cells (non-fused cells) other than the target hybridomas die. Subsequently, screening and single cloning of the hybridoma which produces an antibody of interest are performed using the general limiting dilution method.

The above hybridomas are obtained by an immunizing non-human animal with an antigen. In addition to this method, hybridomas that produce a human antibody having desired activity (e.g., activity of suppressing cell proliferation) can also be obtained by in vitro sensitizing human lymphocytes, such as human lymphocytes that have been infected with the EB virus, with a protein, a protein-expressing cell, or a lysate thereof, followed by fusing of the thus sensitized lymphocytes with human-derived myeloma cells having an ability to permanently divide, such as U266 (Accession No. TIB196).

The thus prepared hybridoma that produces a monoclonal antibody of interest can be passaged in a general culture medium and can be stored in liquid nitrogen over a long period of time.

Specifically, a hybridoma can be prepared by immunizing by a general immunization method using, as a sensitizing antigen, a desired antigen or a cell that expresses the desired antigen, fusing the thus obtained immunized cell with a known parent cell by a general cell fusion method, and then screening for a monoclonal antibody-producing cell (i.e., a hybridoma) by a general screening method.

As a human antibody-producing mouse, a KM mouse (Kirin Pharma/Medarex) and a Xeno mouse (Amgen) are known (e.g., International Patent Publications WO02/43478 and WO02/092812), for example. When such a mouse is immunized with a CAPRIN-1 protein or a fragment thereof, a complete human polyclonal antibody can be obtained from blood. Also, splenocytes are collected from the immunized mouse and then a human-type monoclonal antibody can be prepared by a method for fusion with myeloma cells.

An antigen can be prepared according to a method using animal cells (JP Patent Publication (Kohyo) No. 2007-530068) or baculovirus (e.g., International Patent Publication WO98/46777), for example. When an antigen has low immunogenicity, the antigen may be bound to a macromolecule having immunogenicity, such as albumin, and then immunization is carried out.

Furthermore, an antibody gene is cloned from said hybridoma and then incorporated into an appropriate vector. The vector is then introduced into a host, and then the genetically recombined antibody produced using gene recombination techniques can be used (e.g., see Carl, A. K. Borrebaeck, James, W. Larrick, THERAPEUTIC MONOCLONAL ANTIBODIES, Published in the United Kingdom by MACMILLAN PUBLISHERS LTD, 1990). Specifically, the cDNA of a variable region (V region) of an antibody is synthesized from the mRNA of the hybridoma using reverse transcriptase. When DNA encoding the V region of an antibody of interest can be obtained, this DNA is ligated to DNA encoding the constant region (C region) of a desired antibody, and then the resultant fusion product is incorporated into an expression vector. Alternatively, DNA encoding the V region of an antibody may be incorporated into an expression vector containing the DNA for the C region of an antibody. At this time, the DNA can be incorporated into an expression vector so that it is expressed under the control of expression control regions, such as enhancer and promoter. Next, host cells are transformed with the expression vector, so that the antibody can be expressed.

The anti-CAPRIN-1 antibody of the present invention is characterized by being a monoclonal antibody. Examples of a monoclonal antibody include human monoclonal antibodies, non-human animal monoclonal antibodies (e.g., a mouse monoclonal antibody, a rat monoclonal antibody, a rabbit monoclonal antibody, and a chicken monoclonal antibody), and chimeric monoclonal antibodies. A monoclonal antibody can be prepared by culturing a hybridoma obtained by cell fusion of a splenocyte from a non-human mammal (e.g., a mouse, a human antibody-producing mouse, a chicken, or a rabbit) immunized with a CAPRIN-1 protein, with a myeloma cell. A chimeric antibody is prepared by combining sequences from different animals, such as an antibody comprising heavy chain and light chain variable regions of a mouse antibody and heavy chain and light chain constant regions of a human antibody. A chimeric antibody can be prepared using a known method. For example, a chimeric antibody can be obtained by ligating DNA encoding an antibody V region to DNA encoding a human antibody C region, incorporating the resultant fusion product into an expression vector, and then introducing the vector into a host for production of the chimeric antibody. In Examples described later, human-chicken chimeric monoclonal antibodies were prepared and thus its anti-tumor effects were confirmed. These monoclonal antibodies comprise a heavy chain variable (VH) region comprising the amino acid sequence of SEQ ID NO: 42 and a light chain variable (VL) region comprising the amino acid sequence of SEQ ID NO: 46, wherein the VH region comprises CDR1 represented by the amino acid sequence of SEQ ID NO: 39, CDR2 represented by the amino acid sequence of SEQ ID NO: 40, and CDR3 represented by the amino acid sequence of SEQ ID NO: 41, and the VL region comprises CDR1 represented by the amino acid sequence of SEQ ID NO: 43, CDR2 represented by the amino acid sequence of SEQ ID NO: 44, and CDR3 represented by the amino acid sequence of SEQ ID NO: 45.

A humanized antibody is a modified antibody that is also referred to as a reshaped human antibody. A humanized antibody can be constructed by transplanting CDRs of an antibody from an immunized animal into the complementarity determining regions of a human antibody. General gene recombination techniques therefor are also known.

Specifically, DNA sequences designed to have each of the CDRs of a mouse or chicken antibody ligated to each of the framework regions (FRs) of a human antibody are synthesized by the PCR method from several oligonucleotides, which are prepared so as to have overlap portions at their terminal portions, for example. A humanized antibody can be obtained by ligating the thus obtained DNA to DNA encoding the constant region of a human antibody, incorporating the resultant fusion product into an expression vector, introducing the vector into a host, and thus causing the host to produce the gene product (see European Patent Publication No. 239400 and International Patent Publication WO96/02576). As the FRs of a human antibody, which is ligated via CDRs, FRs that allow the formation of an antigen-binding site with good complementarity determining regions are selected. If necessary, for the formation of an antigen-binding site having the appropriate complementarity determining regions of a reshaped human antibody, the amino acids of the framework regions of an antibody variable region may be substituted (Sato, K. et al., Cancer Research, 1993, 53: 851-856). Also, the amino acids of FRs may be substituted with those of framework regions from various human antibodies (see International Patent Publication WO99/51743).

As the framework regions (FRs) of a human antibody, which are ligated via CDRs, FRs that allows the formation of an antigen-binding site with good complementarity determining regions are selected. If necessary, for the formation of an antigen-binding site having the appropriate complementarity determining regions of a reshaped human antibody, the amino acids of the framework regions of an antibody variable region may be substituted (Sato K. et al., Cancer Research 1993, 53: 851-856).

After preparation of a chimeric antibody or a humanized antibody, amino acids in a variable region (e.g., FR) or a constant region may be substituted with other amino acids.

Amino acid substitution is a substitution of, for example, less than 15, less than 10, 8 or less, 7 or less, 6 or less, 5 or less, 4 or less, 3 or less, or 2 or less amino acids and is preferably a substitution of 1 to 5 amino acids, and more preferably 1 or 2 amino acids. A substituted antibody should be functionally equivalent to an unsubstituted antibody. Substitution is desirably a substitution of a conservative amino acid(s) between amino acids having analogous properties such as electric charge, side chain, polarity, and aromaticity. Amino acids having analogous properties can be classified into basic amino acids (arginine, lysine, and histidine), acidic amino acids (aspartic acid and glutamic acid), uncharged polar amino acids (glycine, asparagine, glutamine, serine, threonine, cysteine, and tyrosine), nonpolar amino acids (leucine, isoleucine, alanine, valine, proline, phenylalanine, tryptophan, and methionine), branched-chain amino acids (threonine, valine, and isoleucine), and aromatic amino acids (phenylalanine, tyrosine, tryptophan, and histidine), for example.

Examples of a modified antibody product include antibodies bound to various molecules such as polyethylene glycol (PEG). Substances to be bound in the modified antibody product of the present invention are not limited. Such a modified antibody product can be obtained by subjecting the thus obtained antibody to chemical modification. Methods therefor have already been established in the art.

As used herein, the term "functionally equivalent" refers to that a subject antibody has biological or biochemical activity similar to that of the antibody of the present invention, and specifically refers to that a subject antibody has the function of impairing tumor without essentially causing rejection upon its application to a human, for example. An example of such activity includes an activity to suppress cell proliferation or a binding activity.

As a method well known by persons skilled in the art for preparation of a polypeptide functionally equivalent to a polypeptide, a method for introducing a mutation into a polypeptide is known. For example, persons skilled in the art can prepare an antibody functionally equivalent to the antibody of the present invention by appropriately introducing a mutation into the antibody using site-directed mutagenesis (Hashimoto-Gotoh, T. et al., (1995) Gene 152, 271-275; Zoller, M J., and Smith, M. (1983) Methods Enzymol. 100, 468-500; Kramer, W. et al., (1984) Nucleic Acids Res. 12, 9441-9456; Kramer, W. and Fritz, H J., (1987) Methods Enzymol. 154, 350-367; Kunkel, T A., (1985) Proc. Natl. Acad. Sci. U.S.A. 82, 488-492; Kunkel (1988) Methods Enzymol. 85, 2763-2766), for example.

An antibody that recognizes an epitope of a CAPRIN-1 protein recognized by the above anti-CAPRIN-1 antibody can be obtained by a method known by persons skilled in the art. For example, such an antibody can be obtained by a method that involves determining an epitope of a CAPRIN-1 protein recognized by an anti-CAPRIN-1 antibody, by a general method (e.g., epitope mapping) and then preparing an antibody using a polypeptide having an amino acid sequence contained in the epitope as an immunogen, or a method that involves determining an epitope of such an antibody prepared by a general method, and then selecting an antibody having the epitope identical with that of an anti-CAPRIN-1 antibody. As used herein, the term "epitope" refers to, in a mammal and preferably a human, a polypeptide fragment having antigenicity or immunogenicity. The minimum size unit thereof consists of about 7 to 12 amino acids, and preferably 8 to 11 amino acids.

The affinity constant $Ka(k_{on}/k_{off})$ of the antibody of the present invention is preferably at least $10^7$ $M^{-1}$, at least $10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, or at least $10^{13}$ $M^{-1}$.

The antibody of the present invention can be conjugated with an antitumor agent. Conjugation of the antibody with an antitumor agent can be carried out via a spacer having a group reactive with an amino group, a carboxyl group, a hydroxy group, a thiol group or the like (e.g., a succinimidyl succinate group, a formyl group, a 2-pyridyldithio group, a maleimidyl group, an alkoxy carbonyl group, and a hydroxy group).

Examples of the antitumor agent include the following known antitumor agents as in prior art literatures and the like, such as paclitaxel, doxorubicin, daunorubicin, cyclophosphamide, methotrexate, 5-fluorouracil, thiotepa, busulfan, improsulfan, piposulfan, benzodopa, carboquone, meturedopa, uredopa, altretamine, triethylenemelamine, triethylenephosphoramide, triethilenethiophosphoramide, trimethylolomelamine, bullatacin, bullatacinone, camptothecin, bryostatin, callystatin, cryptophycin1, cryptophycin8, dolastatin, duocarmycin, eleutherobin, pancratistatin, sarcodictyin, spongistatin, chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, calicheamicin, dynemicin, clodronate, esperamicin, aclacinomycin, actinomycin, authramycin, azaserine, bleomycin, cactinomycin, carabicin, caminomycin, carzinophilin, chromomycin, dactinomycin, detorbicin, 6-diazo-5-oxo-L-norleucine, adriamycin, epirubicin, esorubicin, idarubicin, marcellomycin, mitomycinC, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, androgens (e.g., calusterone, dromostanolone propionate, epitiostanol, mepitiostane, and testolactone), aminoglutethimide, mitotane, trilostane, frolinic acid, aceglatone, aldophosphamideglycoside, aminolaevulinic acid, eniluracil, amsacrine, bestrabucil, bisantrene, edatraxate, defofamine, demecolcine, diaziquone, elformithine, elliptinium acetate, epothilone, etoglucid, lenthinan, lonidamine, maytansine, ansamitocine, mitoguazone, mitoxantrone, mopidanmol, nitraerine, pentostatin, phenamet, pirarubicin, losoxantrone, podophyllinic acid, 2-ethyl hydrazide, procarbazine, razoxane, rhizoxin, schizophyllan, spirogermanium, tenuazonic acid, triaziquone, roridine A, anguidine, urethane, vindesine, dacarbazine, mannomustine, mitobronitol, mitolactol, pipobroman, gacytosine, docetaxel, chlorambucil, gemcitabine, 6-thioguanine, mercaptopurine, cisplatin, oxaliplatin, carboplatin, vinblastine, etoposide, ifosfamide, mitoxanthrone, vincristine, vinorelbine, novantrone, teniposide, edatrexate, daunomycin, aminopterin, xeloda, ibandronate, irinotecan, topoisomerase inhibitor, difluoromethylolnitine (DMFO), retinoic acid, capecitabine, and pharmaceutically acceptable salts or derivatives thereof.

Through administration of the antibody of the present invention in combination with an antitumor agent, even higher therapeutic effects can be obtained. This technique is applicable to both before and after surgery of a cancer patient with the expression of CAPRIN-1. Particularly after surgery, more effective prevention of cancer recurrences or prolonged survival period can be obtained against cancer with the expression of CAPRIN-1, which has been conventionally treated with an antitumor agent alone.

Examples of the antitumor agent to be administered in combination with the antibody of the present invention include the following known antitumor agents as in prior art literatures or the like, such as paclitaxel, doxorubicin, daunorubicin, cyclophosphamide, methotrexate, 5-fluorouracil, thiotepa, busulfan, improsulfan, piposulfan, benzodopa, carboquone, meturedopa, uredopa, altretamine, triethylenemelamine, triethylenephosphoramide, triethilenethiophosphoramide, trimethylolomelamine, bullatacin, bullatacinone, camptothecin, bryostatin, callystatin, cryptophycin1, cryptophycin8, dolastatin, duocarmycin, eleutherobin, pancratistatin, sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, calicheamicin, dynemicin, clodronate, esperamicin, aclacinomycin, actinomycin, authramycin, azaserine, bleomycin, cactinomycin, carabicin, caminomycin, carzinophilin, chromomycin, dactinomycin, detorbicin, 6-diazo-5-oxo-L-norleucine, adriamycin, epirubicin, esorubicin, idarubicin, marcellomycin, mitomycinC, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, calusterone, dromostanolone propionate, epitiostanol, mepitiostane, testolactone, aminoglutethimide, mitotane, trilostane, frolinic acid, aceglatone, aldophosphamideglycoside, aminolaevulinic acid, eniluracil, amsacrine, bestrabucil, bisantrene, edatraxate, defofamine, demecolcine, diaziquone, elfornithine, elliptinium acetate, epothilone, etoglucid, lenthinan, lonidamine, maytansine, ansamitocine, mitoguazone, mitoxantrone, mopidanmol, nitraerine, pentostatin, phenamet, pirarubicin, losoxantrone, podophyllinic acid, 2-ethyl hydrazide, procarbazine, razoxane, rhizoxin, schizophyllan, spirogermanium, tenuazonic acid, triaziquone, roridine A, anguidine, urethane, vindesine, dacarbazine, mannomustine, mitobronitol, mitolactol, pipobroman, gacytosine, docetaxel, chlorambucil, gemcitabine, 6-thioguanine, mercaptopurine, cisplatin, oxaliplatin, carboplatin, vinblastine, etoposide, ifosfamide, mitoxanthrone, vincristine, vinorelbine, novantrone, teniposide, edatrexate, daunomycin, aminopterin, xeloda, ibandronate, irinotecan, topoisomerase inhibitor, difluoromethylolnitine (DMFO), retinoic acid, capecitabine, and pharmaceutically acceptable (known) salts or (known) derivatives thereof. Of the above examples, particularly cyclophosphamide, paclitaxel, docetaxel, and vinorelbine are preferably used.

Alternatively, a known radio isotope as in prior art literatures or the like, such as $^{211}At$, $^{131}I$, $^{125}I$, $^{90}Y$, $^{186}Re$, $^{188}Re$, $^{153}Sm$, $^{212}Bi$, $^{32}P$, $^{175}Lu$, or $^{176}Lu$ can be bound to the antibody of the present invention. A desired radio isotope is effective for treatment or diagnosis of tumor.

The antibody of the present invention is an antibody having immunological reactivity with CAPRIN-1, or, an antibody specifically binding to CAPRIN-1, which exhibits cytotoxic activity against cancer or the effect of suppressing tumor growth. The antibody should have a structure such that rejection is almost or completely avoided in a subject animal to which the antibody is administered. Examples of such an antibody include, when a subject animal is a human, a human antibody, a humanized antibody, a chimeric antibody (e.g., a human-mouse chimeric antibody), a single chain antibody, and a bispecific antibody. These antibodies are: recombinant antibodies in which heavy chain and light chain variable regions are from a human antibody; recombinant antibodies in which heavy chain and light chain variable regions comprise complementarity determining regions (CDRs) (CDR1, CDR2, and CDR3) from a non-human animal antibody and framework regions from a human antibody; or recombinant antibodies in which heavy chain and light chain variable regions are from a non-human animal antibody, and, heavy chain and light chain constant regions are from a human antibody. Preferable antibodies are the former two antibodies.

These recombinant antibodies can be prepared as follows by cloning DNA encoding an anti-human CAPRIN-1 monoclonal antibody (e.g., a human monoclonal antibody, a mouse monoclonal antibody, a rat monoclonal antibody, a rabbit monoclonal antibody, or a chicken monoclonal antibody) from an antibody-producing cell such as a hybridoma, preparing DNA encoding a light chain variable region and a heavy chain variable region of the antibody by an RT-PCR method using it as a template, and then determining the sequence of each variable region of light chain and heavy chain or each sequence of CDR1, CDR2, and CDR3 based on a Kabat EU numbering system (Kabat et al., Sequences of Proteins of Immunological Interest, $5^{th}$ Ed. Public Health Service, National Institute of Health, Bethesda, Md. (1991)).

Furthermore, DNA encoding each of these variable regions or DNA encoding each CDR is prepared using gene recombination techniques (Sambrook et al., Molecular Cloning: A Laboratory Manual, Cold Spring Harbor Laboratory Press (1989)) or a DNA synthesizer. Here, the above human monoclonal antibody-producing hybridoma can be prepared by immunizing a human antibody-producing animal (e.g., a mouse) with human CAPRIN-1 and then fusing splenocytes excised from the immunized animal to myeloma cells. Alternatively, DNAs encoding a light chain or heavy chain variable region and a constant region from a human antibody are prepared as necessary using gene recombination techniques or a DNA synthesizer.

In the case of humanized antibody, DNA is prepared by substituting a CDR coding sequence in DNA encoding a variable region of light chain or heavy chain derived from a human antibody, with a CDR coding sequence corresponding thereto of an antibody derived from a non-human animal (e.g., a mouse, a rat, or a chicken) and then ligating the DNA thus obtained to DNA encoding a constant region of light chain or heavy chain derived from a human antibody. Thus, DNA encoding humanized antibody can be prepared.

In the case of chimeric antibody, DNA encoding a chimeric antibody can be prepared by ligating DNA encoding a light chain or heavy chain variable region of an antibody from a non-human animal (e.g., a mouse, a rat, and a chicken) to DNA encoding a light chain or heavy chain constant region from a human antibody.

In the case of single chain antibody, this antibody is an antibody prepared by linearly ligating a heavy chain variable region to a light chain variable region via a linker. Thus, DNA encoding a single chain antibody can be prepared by binding DNA encoding a heavy chain variable region, DNA encoding a linker, and DNA encoding a light chain variable region. Herein, a heavy chain variable region and a light chain variable region are both from a human antibody, or, only CDRs are substituted with CDRs of an antibody from a non-human animal (e.g., a mouse, a rat, and a chicken) although the other regions are from a human antibody. Also, a linker comprises 12 to 19 amino acids, such as $(G_4S)_3$ of 15 amino acids (G. -B. Kim et al., Protein Engineering Design and Selection 2007, 20 (9): 425-432).

In the case of bispecific antibody (diabody), this antibody is capable of specifically binding to two different epitopes. For example, DNA encoding a bispecific antibody can be prepared by linking DNA encoding a heavy chain variable region A, DNA encoding a light chain variable region B, DNA encoding a heavy chain variable region B, and DNA encoding a light chain variable region A in this order (here, DNA encoding a light chain variable region B is bound to DNA encoding a heavy chain variable region B via DNA encoding the above linker). Here, a heavy chain variable region and a light chain variable region are both from a human antibody, or, only CDRs are substituted with CDRs of an antibody from a non-human animal (e.g., a mouse, a rat, or a chicken) although the other regions are from a human antibody.

The above-prepared recombinant DNA is incorporated into one or a plurality of appropriate vectors, they are introduced into host cells (e.g., mammalian cells, yeast cells, or insect cells), and then (co)expression is caused, so that a recombinant antibody can be prepared (P. J. Delves., ANTIBODY PRODUCTION ESSENTIAL TECHNIQUES., 1997 WILEY, P. Shepherd and C. Dean., Monoclonal Antibodies., 2000 OXFORD UNIVERSITY PRESS; J. W. Goding., Monoclonal Antibodies: principles and practice., 1993 ACADEMIC PRESS).

Examples of the antibody of the present invention prepared by the above method include an antibody comprising a heavy chain variable region comprising SEQ ID NOS: 39, 40, and 41 and a light chain variable region comprising SEQ ID NOS: 43, 44, and 45 (e.g., the antibody composed of the heavy chain variable region of SEQ ID NO: 42 and the light chain variable region of SEQ ID NO: 46).

The amino acid sequences represented by SEQ ID NOS: 39, 40, and 41 are CDR1, CDR2, and CDR3 of a chicken antibody heavy chain variable region. Also, the amino acid sequences represented by SEQ ID NOS: 43, 44, and 45 are CDR1, CDR2, and CDR3 of a chicken antibody light chain variable region, respectively.

Also, the humanized antibody, the chimeric antibody, the single chain antibody, or the bispecific antibody of the present invention is the following antibody, for example:

(i) an antibody wherein a heavy chain variable region comprises the amino acid sequences of SEQ ID NOS: 39, 40, and 41 and the amino acid sequences of framework regions from a human antibody, and, a light chain variable region comprises the amino acid sequences of SEQ ID NOS: 43, 44, and 45 and the amino acid sequences of framework regions from a human antibody (e.g., the antibody wherein the heavy chain variable region comprises the amino acid sequence of SEQ ID NO: 42, and, the light chain variable region comprises the amino acid sequence of SEQ ID NO: 46); and (ii) an antibody wherein a heavy chain variable region comprises the amino acid sequences of SEQ ID NOS: 39, 40, and 41 and the amino acid sequences of framework regions from a human antibody, and, a heavy chain constant region comprises an amino acid sequence from a human antibody, and, a light chain variable region comprises the amino acid sequences of SEQ ID NOS: 43, 44, and 45 and the amino acid sequences of framework regions from a human antibody, and a light chain constant region comprises an amino acid sequence from a human antibody (e.g., the antibody wherein a heavy chain variable region comprises the amino acid sequence of SEQ ID NO: 42, and, a heavy chain constant region comprises an amino acid sequence from a human antibody, as well as, a light chain variable region comprises the amino acid sequence of SEQ ID NO: 46, and, a light chain constant region comprises an amino acid sequence from a human antibody).

In addition, the sequences of human antibody heavy chain and light chain constant regions and variable regions can be obtained from NCBI (e.g., U.S.A.: GenBank, UniGene), for example. For example, the sequence of Accession No. J00228 can be referred to as a human IgG1 heavy chain constant region, the sequence of Accession No. J00230 can be referred to as a human IgG2 heavy chain constant region, the sequence of Accession No. X03604 can be referred to as a human IgG3 heavy chain constant region, the sequence of Accession No. K01316 can be referred to as a human IgG4 heavy chain constant region, the sequences of Accession No. V00557, X64135, X64133, and the like can be referred to as human light chain κ constant regions, and the sequences of registration nos. X64132, X64134, and the like can be referred to as human light chain λ constant regions.

The above antibodies preferably have cytotoxic activity and thus can exhibit anti-tumor effects.

Also, the specific sequences of heavy chain and light chain variable regions or CDRs in the above antibodies are given simply for illustrative purposes, and thus are clearly not limited to such specific sequences. A hybridoma capable of producing another human antibody or non-human animal antibody (e.g., a mouse antibody) against human CAPRIN-1 is prepared, a monoclonal antibody that is produced by the hybridoma is collected, and then whether or not it is a target antibody is determined by immunological binding property with human CAPRIN-1 and cytotoxic activity as indicators. After identification of a hybridoma producing the target monoclonal antibody in this manner, DNA encoding heavy chain and light chain variable regions of the target antibody is prepared from the hybridoma as described above, sequencing is carried out, and then the DNA is used for preparation of another antibody.

Furthermore, the above antibody of the present invention, the sequence of each of the above antibodies, particularly the sequence of the framework region and/or the sequence of the constant region may have a substitution, a deletion, or an addition of one or several (preferably, 1 or 2) amino acids, as long as it has specificity for specific recognition of CAPRIN-1. Here the term “several” refers to 2 to 5, and preferably 2 or 3.

The present invention further provides DNA encoding the above antibody of the present invention, or, DNA encoding the above antibody heavy chain or light chain, or, DNA encoding the above antibody heavy chain or light chain variable region. Examples of such DNA include, DNA encoding a heavy chain variable region comprising the nucleotide sequences encoding the amino acid sequences of SEQ ID NOS: 39, 40, and 41 and DNA encoding a light chain variable region comprising the nucleotide sequences encoding the amino acid sequences of SEQ ID NOS: 43, 44, and 45.

Complementarity determining regions (CDRs) encoded by the sequences of DNA are regions for determining the specificity of an antibody. Thus, sequences encoding regions in an antibody other than CDRs (specifically, a constant region and a framework region) may be from other antibodies. Here, examples of such “other antibodies” include antibodies from non-human organisms, and are preferably from a human in view of reduction of side effects. Thus, in the case of the above DNA, regions encoding each framework region and each contact region of heavy chains and light chains preferably comprise nucleotide sequences encoding corresponding amino acid sequences from a human antibody.

Further alternative examples of DNA encoding the antibody of the present invention include DNA encoding a heavy chain variable region comprising the nucleotide sequence encoding the amino acid sequence of SEQ ID NO: 42 and DNA in which the region encoding a light chain variable region comprises the nucleotide sequence encoding the amino acid sequence of SEQ ID NO: 46. Here, an example of the nucleotide sequence encoding the amino acid sequence of SEQ ID NO: 42 is the nucleotide sequence of SEQ ID NO: 49. Also, an example of the nucleotide sequence encoding the amino acid sequence of SEQ ID NO: 46 is the nucleotide sequence of SEQ ID NO: 50. In these DNAs, regions encoding each constant region of heavy chains and light chains preferably comprise nucleotide sequences encoding the corresponding amino acid sequences from a human antibody.

The DNA of the present invention can be obtained by the above methods or the following method, for example. First, total RNA is prepared from a hybridoma relating to the antibody of the present invention using a commercially available RNA extraction kit, and then cDNA is synthesized with reverse transcriptase using random primers, and the like. Subsequently, cDNA encoding an antibody is amplified by a PCR method using as primers the oligonucleotides of sequences conserved in each variable region of known mouse antibody heavy chain and light chain genes. The sequence encoding a constant region can be obtained by amplifying a known sequence by a PCR method. The nucleotide sequence of DNA can be determined by a conventional method such as insertion of it into a plasmid or a phage for sequencing.

An anti-CAPRIN-1 antibody to be used in the present invention is considered to exhibit the anti-tumor effects against CAPRIN-1-expressing cancer cells through the following mechanism.

Antibody-dependent cytotoxic activity (ADCC) of effector cells against CAPRIN-1-expressing cells, and the complement-dependent cytotoxicity (CDC) against CAPRIN-1-expressing cells.

Therefore, the activity of an anti-CAPRIN-1 antibody to be used in the present invention can be evaluated by, as specifically described in Examples below, measuring ex vivo the above ADCC activity or CDC activity against CAPRIN-1-expressing cancer cells.

An anti-CAPRIN-1 antibody to be used in the present invention binds to a CAPRIN-1 protein on a cancer cell and exhibits anti-tumor effects due to the above activity, and thus it is useful for treating or preventing cancer. Specifically, the present invention provides a pharmaceutical composition for treating and/or preventing a cancer, which comprises an anti-CAPRIN-1 antibody as an active ingredient. When the anti-CAPRIN-1 antibody is used for administration thereof to a human body (antibody therapy), it is preferably human antibody or humanized antibody in order to decrease immunogenicity.

In addition, the higher the binding affinity between an anti-CAPRIN-1 antibody and a CAPRIN-1 protein on the cancer cell surfaces, the stronger the anti-tumor activity of the anti-CAPRIN-1 antibody that can be obtained. Therefore, when an anti-CAPRIN-1 antibody having high binding affinity with a CAPRIN-1 protein can be acquired, stronger anti-tumor effects can be expected and such antibody's application as a pharmaceutical composition for the purpose of cancer treatment and/or prevention becomes possible. Such high binding affinity is desirably as follows. As described above, binding constant (affinity constant) Ka ($k_{on}/k_{off}$) is preferably at least $10^7$ $M^{-1}$, at least $10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, or, at least $10^{13}$ $M^{-1}$.

<Binding to Antigen-expressing Cell>

The capacity of an antibody to bind to CAPRIN-1 can be specified by binding assay using ELISA, a Western blot method, immuno-fluorescence and flow cytometric analysis, or the like as described in Examples.

<Immunohistochemical Staining>

An antibody that recognizes CAPRIN-1 can be tested for reactivity to CAPRIN-1 by a method for immunohistochemistry known by persons skilled in the art using paraformaldehyde- or acetone-fixed frozen sections or paraformaldehyde-fixed paraffin-embedded tissue sections, which is prepared from tissue samples obtained from a patient during surgery, or tissue samples obtained from an animal having heterotransplant tissue inoculated with a cell line expressing CAPRIN-1, naturally or after transfection.

An antibody reactive with CAPRIN-1 can be stained by various methods for immunohistochemical staining. For example, a horseradish peroxidase-conjugated goat anti-mouse antibody or goat anti-chicken antibody is caused to undergo reaction, a target antibody can be visualized.

<Pharmaceutical Composition>

A target of the pharmaceutical composition for treating and/or preventing a cancer of the present invention is not particularly limited, as long as it is a cancer (cell) expressing a CAPRIN-1 gene.

The term "tumor" and "cancer" as used herein refers to malignant neoplasm and is used interchangeably.

Cancer to be subjected to the present invention is cancer expressing genes encoding CAPRIN-1 proteins having amino acid sequences of even-numbered SEQ ID NOS: 2 to 30. Examples of such cancer include preferably breast cancer, brain tumor, leukemia, lung cancer, lymphoma, mastocytoma, renal cancer, uterine cervix cancer, bladder cancer, esophageal cancer, gastric cancer, and colorectal cancer.

Examples of such specific cancer include, but are not limited to, breast adenocarcinoma, composite type breast adenocarcinoma, mammary gland malignant mixed tumor, intraductal papillary adenocarcinoma, lung adenocarcinoma, squamous cell carcinoma, small cell carcinoma, large cell carcinoma, glioma that is neural epithelial tissue tumor, ependymoma, neurocytoma, fetal neuroectodermal tumor, schwannoma, neurofibroma, meningioma, chronic lymphocytic leukemia, lymphoma, gastrointestinal lymphoma, digestive lymphoma, small-cell to medium-cell lymphoma, cancer of cecum, ascending colon cancer, descending colon cancer, transverse colon cancer, sigmoid colon cancer, and rectal cancer.

Moreover, preferable subjects are mammals including primates, pet animals, domestic animals, animals for race, and the like and are particularly preferably humans, dogs, and cats.

When an antibody to be used in the present invention is used as a pharmaceutical composition, it can be formulated by a method known by persons skilled in the art. For example, the antibody can be used parenterally in the form of an injection preparation such as an aseptic solution or a suspension prepared with water or a pharmacologically acceptable solution other than water. For example, it can be formulated by mixing in a unit dosage form required by generally accepted pharmaceutical practice in appropriate combination with a pharmacologically acceptable carrier or medium, specifically, sterile water or saline, vegetable oil, an emulsifier, a suspension, a surfactant, a stabilizer, a flavoring compound, an excipient, a vehicle, an antiseptic, a binder, and the like. The amounts of active ingredients in these preparations are determined so that an appropriate dose within the indicated range can be obtained.

An aseptic composition for injection can be prescribed according to general pharmaceutical practice using a vehicle such as distilled water for injection.

Examples of an aqueous solution for injection include saline, an isotonic solution containing dextrose or other adjuvants, such as D-sorbitol, D-mannose, D-mannitol, and sodium chloride. These examples may be used in combination with an appropriate solubilizing agent such as alcohol, specifically ethanol and polyalcohol (e.g., propylene glycol and polyethylene glycol), and nonionic surfactant (e.g., polysorbate 80 (TM) and HCO-60).

Examples of the oil include sesame oil and soybean oil, which can be used in combination with a solubilizing agent such as benzyl benzoate or benzyl alcohol. Also, a buffering agent such as phosphate buffer or sodium acetate buffer, a soothing agent such as procaine hydrochloride, a stabilizer such as benzyl alcohol or phenol, and an antioxidant may be combined therewith. An appropriate amplus is generally filled with the thus prepared injection solution.

Administration is peroral or perenteral administration and is preferably perenteral administration. Specific examples of the route of administration include injection, transnasal administration, pulmonary administration, and transdermal administration. Examples of injection include intravenous injection, intramuscular injection, intraperitoneal injection, and subcutaneous injection, so that systemic or local administration is possible.

Also, administration methods can be appropriately selected depending on a patient's age, body weight, gender, symptoms, and the like. The dosage per administration of a pharmaceutical composition containing an antibody or a polynucleotide encoding the antibody can be selected from the range between 0.0001 mg and 1000 mg per kg of body weight, for example. Alternatively, for example, dosage can be selected from the range between 0.001 mg/body and 100000 mg/body per patient. However, the dosage range is not always limited to these numerical values. The dosage and administration method are varied depending on a patient's body weight, age, gender, symptoms, and the like, but can be appropriately selected by persons skilled in the art.

The above pharmaceutical composition containing the antibody or a fragment thereof of the present invention is administered to a subject, so that cancer, preferably, breast cancer, brain tumor, leukemia, lung cancer, lymphoma, mastocytoma, renal cancer, uterine cervix cancer, bladder cancer, esophageal cancer, gastric cancer, and colorectal cancer can be treated and/or prevented.

The present invention further encompasses a method for treating and/or preventing a cancer, comprising administering to a subject the pharmaceutical composition of the present invention in combination with the above exemplified antitumor agent or pharmaceutical composition containing such antitumor agent. The antibody or a fragment thereof of the present invention and an antitumor agent may be administered simultaneously or separately to a subject. They can be separately administered regardless of the order of administration. The administration intervals, dosage, the route of administration, and the frequency of administration can be appropriately selected by a specialist. Examples of the other pharmaceutical formulation to be administered simultaneously include pharmaceutical compositions obtained by mixing the antibody or a fragment thereof of the present invention with an antitumor agent in a pharmacologically acceptable carrier (or a medium) followed by formulation. Furthermore, about either the above pharmaceutical composition containing an antitumor agent and formulation, explanations concerning prescription, formulation, the route of administration, dose, cancer, and the like for administering a pharmaceutical composition containing the antibody of the present invention and formulation are applicable.

Therefore, the present invention also provides a pharmaceutical combination for treating and/or preventing a cancer, comprising the pharmaceutical composition of the present invention, and the above exemplified pharmaceutical composition containing an antitumor agent.

Also, the present invention provides a pharmaceutical composition for treating and/or preventing a cancer, comprising the antibody or a fragment thereof of the present invention and an antitumor agent together with a pharmacologically acceptable carrier.

<Polypeptide and DNA>

The present invention further provides the following polypeptides and DNAs relating to the above antibodies.

(i) A polypeptide comprising the amino acid sequence of SEQ ID NO: 42 and DNA encoding the polypeptide, wherein the DNA comprises the nucleotide sequence of SEQ ID NO: 49.

(ii) A polypeptide comprising the amino acid sequence of SEQ ID NO: 46 and DNA encoding the polypeptide, wherein the DNA comprises the nucleotide sequence of SEQ ID NO: 50.

(iii) A heavy chain CDR polypeptide consisting of the amino acid sequences represented by SEQ ID NOS: 39, 40, and 41, and DNA encoding the polypeptide.

(iv) A light chain CDR polypeptide consisting of the amino acid sequences represented by SEQ ID NOS: 43, 44, and 45, and DNA encoding the polypeptide.

These polypeptides and DNAs can be prepared using gene recombination techniques as described above.

<Summary of the Present Invention>

The above-explained present invention is as summarized as follows.

(1) A pharmaceutical composition for treating and/or preventing a cancer, comprising an antibody that comprises a heavy chain variable region comprising SEQ ID NOS: 39, 40, and 41 and a light chain variable region comprising SEQ ID NOS: 43, 44, and 45 or a fragment thereof as an active ingredient and has immunological reactivity with a CAPRIN-1 protein.

(2) The pharmaceutical composition according to (1) above, wherein the cancer is breast cancer, brain tumor, leukemia, lymphoma, lung cancer, mastocytoma, renal cancer, uterine cervix cancer, esophageal cancer, gastric cancer, bladder cancer, or colorectal cancer.

(3) The pharmaceutical composition according to (1) or (2) above, wherein the antibody is a human antibody, humanized antibody, chimeric antibody, single chain antibody, or bispecific antibody.

(4) An antibody, which comprises a heavy chain variable region comprising SEQ ID NOS: 39, 40, and 41 and a light chain variable region comprising SEQ ID NOS: 43, 44, and 45, and has immunological reactivity with a CAPRIN-1 protein.

(5) The antibody according to (4) above, which is a human antibody, humanized antibody, chimeric antibody, single chain antibody, or bispecific antibody.

(6) A pharmaceutical combination for treating and/or preventing a cancer, comprising the pharmaceutical composition of any one of (1) to (3) above and a pharmaceutical composition containing an antitumor agent.

(7) A method for treating and/or preventing a cancer, comprising administering to a subject the pharmaceutical composition according to any one of (1) to (3) above or the antibody of any one of (3) to (5) above or a fragment thereof.

(8) A method for treating and/or preventing a cancer, comprising using pharmaceutical compositions of the pharmaceutical combination of (6) above in combination in a subject.

EXAMPLES

The present invention is described more specifically based on Examples, but the scope of the present invention is not limited by these specific examples.

Example 1

Identification of Novel Cancer Antigen Protein by SEREX Method (1) Preparation of cDNA Library Total RNA was extracted from a testis tissue of a healthy dog by an acid guanidium-phenol-chloroform method. PolyA RNA was purified according to protocols included with an Oligotex-dT30 mRNA purification Kit (Takara Shuzo Co., Ltd.) using the kit.

A dog testis cDNA phage library was synthesized using the thus obtained mRNA (5 μg). For preparation of the cDNA phage library, a cDNA synthesis kit, a ZAP-cDNA synthesis kit, and a ZAP-cDNA gigapack III gold cloning kit (STRATAGENE) were used and the library was prepared according to protocols included with the kit. The size of the thus prepared cDNA phage library was $7.73\times10^5$ pfu/ml.

(2) Screening of cDNA Library Using Serum

Immunoscreening was carried out using the above-prepared dog testis cDNA phage library. Specifically, host *Escherichia coli* (XL1-Blue MRF') was infected with the phage so that 2210 clones were present on a φ90×15 mm NZY agarose plate. Cells were cultured at 42° C. for 3 to 4 hours, so as to cause plaque formation. The plate was covered with a nitrocellulose membrane (Hybond C Extra: GE HealthCare Bio-Sciences) impregnated with IPTG (isopropyl-β-D-thiogalactoside) at 37° C. for 4 hours. Proteins were induced, expressed, and then transferred to the membrane. Subsequently, the membrane was recovered, immersed, and shaken in TBS (10 mM Tris-HCl, 150 mM NaCl pH 7.5) containing 0.5% powdered skim milk at 4° C. overnight, so that nonspecific reaction was suppressed. The filter was caused to react with 500-fold diluted sera of dogs with cancer at room temperature for 2 to 3 hours.

As the above sera from dogs with cancer, sera collected from dogs with breast cancer were used. The sera were stored at −80° C. and then subjected to pretreatment immediately before use. Pretreatment for sera was performed by the following method. Specifically, host *Escherichia coli* (XL1-Blure MRF') was infected with λ ZAP Express phage into which no foreign gene had been inserted, and then cultured on NZY plate medium at 37° C. overnight. Subsequently, a 0.2 M $NaHCO_3$ buffer (pH 8.3) containing 0.5 M NaCl was added to the plate and then the plate was left to stand at 4° C. for 15 hours. The supernatants were collected as *Escherichia coli*/phage extracts. Next, the collected *Escherichia coli*/phage extract was passed through a NHS-column (GE HealthCare Bio-Sciences), so as to immobilize the *Escherichia coli*.phage-derived protein. The serum of a dog with cancer was passed through the column to which the protein had been immobilized for reaction, thereby removing *Escherichia coli* and antibodies adsorbed to the phage from the serum. Each serum fraction that had passed through the column was diluted 500-fold with TBS containing 0.5% powdered skim milk, and the resultant was used as an immunoscreening material.

A membrane, to which the thus treated serum and the fusion protein had been blotted, was washed 4 times with TBS-T (0.05% Tween20/TBS). The membrane was reacted with goat anti-dog IgG (Goat anti Dog IgG-h+I HRP conjugated: BETHYL Laboratories) diluted 5000-fold as a secondary antibody with TBS containing 0.5% powdered skim milk at room temperature for 1 hour. Detection was carried out by enzyme color reaction using an NBT/BCIP reaction solution (Roche). Colonies corresponding to the color reaction positive site were collected from the φ90×15 mm NZY agarose plate, and then dissolved in 500 μl of SM buffer (100 mM NaCl, 10 mM $MgClSO_4$, 50 mM Tris-HCl, 0.01% gelatin, pH 7.5). Until unification of color reaction positive colonies, secondary screening and tertiary screening were repeated by a method similar to the above. Thus, 30940 phage clones that had reacted with serum IgG were screened so that 5 positive clones were isolated.

(3) Homology Search for Isolated Antigen Gene

A procedure for conversion of phage vectors to plasmid vectors was performed for the 5 positive clones isolated by the above method for the purpose of subjecting the clones to nucleotide sequence analysis. Specifically, 200 μl of a solution of host *Escherichia coli* (XL1-Blue MRF') prepared to give an absorbance $OD_{600}$ of 1.0, 250 μl of a purified phage solution, and 1 μl of ExAssist helper phage (STRATAGENE) were mixed and allowed to react at 37° C. for 15 minutes. After that, 3 ml of LB medium was added, cells were cultured at 37° C. for 2.5 to 3 hours, and then the resultant was immediately put in water bath at 70° C. for incubation for 20 minutes. Centrifugation was carried out at 4° C., 1000×g for 15 minutes, and then the supernatant was collected as a phagemid solution. Subsequently, 200 μl of a solution prepared from phagemid host *Escherichia coli* SOLR to give an absorbance $OD_{600}$ of 1.0 and 10 μl of the purified phage solution were mixed, followed by 15 minutes of reaction at 37° C. 50 μl of the resultant was plated on LB agar medium containing ampicillin (at final concentration of 50 μg/ml) and then cultured overnight at 37° C. A single colony of transformed SOLR was collected and then cultured on LB medium containing ampicillin (at final concentration of 50 μg/ml) at 37° C. After culture, plasmid DNA carrying an insert of interest was purified using a QIAGEN plasmid Miniprep Kit (QIAGEN).

The purified plasmid was subjected to the analysis of the entire sequence of the insert by the primer walking method using the T3 primer of SEQ ID NO: 31 and the T7 primer of SEQ ID NO: 32. The gene sequences of SEQ ID NOS: 5, 7, 9, 11, and 13 were obtained by the sequence analysis. With the use of the nucleotide sequences of the genes and the amino acid sequences thereof (SEQ ID NOS: 6, 8, 10, 12, and 14), homology search program BLAST search (http://www.ncbi.nlm.nih.gov/BLAST/) was conducted for searching homology with known genes. As a result, it was revealed that all the five obtained genes were genes encoding CAPRIN-1. The sequence identities among the five genes were 100% at the nucleotide sequence level and 99% at the amino acid sequence level in the regions to be translated into proteins. The sequence identities of these genes and the human homologue-encoding gene were 94% at the nucleotide sequence level and 98% at the amino acid sequence level in the regions to be translated into proteins. The nucleotide sequences of the human homologues are represented by SEQ ID NOS: 1 and 3 and the amino acid sequences of the same are represented by SEQ ID NOS: 2 and 4. Also, the sequence identities of the obtained dog genes and the cattle homologue-encoding gene were 94% at the nucleotide sequence level and 97% at the amino acid sequence level in the regions to be translated into proteins. The nucleotide sequence of the cattle homologue is represented by SEQ ID NO: 15 and the amino acid sequence of the same is represented by SEQ ID NO: 16. In addition, the sequence identities of the human homologue-encoding genes and the cattle homologue-encoding gene were 94% at the nucleotide sequence level and 93% to 97% at the amino acid sequence level in the regions to be translated into proteins. Also, the sequence identities of the obtained dog genes and the horse homologue-encoding gene were 93% at the nucleotide sequence level and 97% at the amino acid sequence level in the regions to be translated into proteins. The nucleotide sequence of the horse homologue is represented by SEQ ID NO: 17 and the amino acid sequence of the same is represented by SEQ ID NO: 18. In addition, the sequence identities of the human homologue-encoding genes and the horse homologue-encoding gene were 93% at the nucleotide sequence level and 96% at the amino acid sequence level in the regions to be translated into proteins. Also, the sequence identities of the obtained dog genes and the mouse homologue-encoding genes were 87% to 89% at the nucleotide sequence level and 95% to 97% at the amino acid sequence level in the regions to be translated into proteins. The nucleotide sequences of the mouse homologues are represented by SEQ ID NOS: 19, 21, 23, 25, and 27 and the amino acid sequences of the same are represented by SEQ ID NOS: 20, 22, 24, 26, and 28. In addition, the sequence identities of the human homologue-encoding genes and the mouse homologue-encoding genes were 89% to 91% at the nucleotide sequence level and were 95% to 96% at the amino acid sequence level in the regions to be translated into proteins. Also, the sequence identities of the obtained dog genes and the chicken homologue-encoding gene were 82% at the nucleotide sequence level and 87% at the amino acid sequence level in the regions to be translated into proteins. The nucleotide sequence of the chicken homologue is represented by SEQ ID NO: 29 and the amino acid sequence of the same is represented by SEQ ID NO: 30. In addition, the sequence identities of the human homologue-encoding genes and the chicken homologue-encoding gene were 81% to 82% at the nucleotide sequence level and 86% at the amino acid sequence level in the regions to be translated into proteins.

(4) Gene Expression Analysis in Each Tissue

The expression of genes obtained by the above method was examined in dog and human normal tissues and various cell lines by an RT-PCR method. Reverse transcription reaction was performed as follows. Specifically, total RNA was extracted from 50 mg to 100 mg of the tissue or 5 to $10\times10^6$ cells of the cell line using a TRIZOL reagent (Invitrogen) according to the accompanying protocols. cDNA was synthesized with the total RNA using a Superscript First-Strand Synthesis System for RT-PCR (Invitrogen) according to the accompanying protocols. PCR was performed as follows using primers of SEQ ID NOS: 33 and 34 specific to the obtained genes. Specifically, reagents and an accompanying buffer were added to 0.25 μl of the sample prepared by the reverse transcription reaction to a total volume of 25 μl, so that the resultant contained the above primers of 2 μM each, dNTPs of 0.2 mM each, and 0.65 U ExTaq polymerase (Takara Shuzo Co., Ltd.). PCR was carried out by repeating a cycle of 94° C. for 30 seconds, 60° C. for 30 seconds, and 72° C. for 30 seconds 30 times using a Thermal Cycler (BIO RAD). The above gene-specific primers are capable of amplifying the region ranging from nucleotides 206 to 632 in the nucleotide sequence of SEQ ID NO: 5 (dog CAPRIN-1 gene) and the region ranging from nucleotides 698 to 1124 in the nucleotide sequence of SEQ ID NO: 1 (human CAPRIN-1 gene). As a control for comparison, GAPDH-specific primers of SEQ ID NOS: 35 and 36 were also used concurrently. As a result, as shown in FIG. 1, strong expression was observed in testis among normal dog tissues, while expression was observed in dog breast cancer and adenocarcinoma tissues. Moreover, the observation of the expression of the human homologues from the obtained genes was also carried out. As a result, similarly to the case of the dog CAPRIN-1 gene, expression could be observed in only testis among normal tissues. However, in the case of cancer cells, expression was detected in many types of cancer cell lines, including breast cancer, brain tumor, leukemia, lung cancer, and esophageal cancer cell lines. Expression was observed particularly in many breast cancer cell lines. It was confirmed by the results that the expression of CAPRIN-1 is not observed in normal tissues other than testis, while CAPRIN-1 was expressed in many cancer cells and particularly in breast cancer cell lines.

In FIG. 1, reference number 1 on each vertical axis indicates the expression patterns of genes identified above and reference number 2 indicates the expression patterns of the GAPDH gene as a control.

(5) Immunohistochemical Staining (5)-1 CAPRIN-1 Expression in Mouse and Dog Normal Tissues Mice (Balb/c, female) and dogs (beagles, female) were exsanguinated under ether anesthesia and ketamine/isoflurane anesthesia. After laparotomy, each organ (stomach, liver, eyeball, thymus gland, muscle, bone marrow, uterus, small bowel, esophagus, heart, kidney, salivary gland, large bowel, mammary gland, brain, lung, skin, adrenal gland, ovary, pancreas, spleen, and bladder) was transferred to a 10-cm dish containing PBS. Each organ was cut open in PBS and then subjected to perfusion fixation overnight in 0.1 M phosphate buffer (pH 7.4) containing 4% paraformaldehyde (PFA). The perfusion solution was discarded, the tissue surface of each organ was rinsed with PBS, a PBS solution containing 10% sucrose was added to a 50-ml centrifuge tube, each tissue was added to the tube, and then the tube was shaken using a rotor at 4° C. for 2 hours. The solution was replaced by a PBS solution containing 20% sucrose, and then left to stand at 4° C. until the tissue sank. The solution was replaced by a PBS solution containing 30% sucrose and then left to stand at 4° C. until the tissue sank. The tissue was removed and then needed portions were excised with a surgical scalpel. Next, an OCT compound (Tissue Tek) was added to the tissue so that it was thoroughly applied to the tissue surface, and then the tissue was placed in a cryomold. The cryomold was placed on dry ice for quick freezing. Thereafter, the tissue was sliced to 10 μm to 20 μm using a cryostat (LEICA). Slices were air-dried on slide glasses using a hair dryer for 30 minutes, to prepare the sliced tissue mounted on a slide glass. Next, each sample was placed in a staining bottle filled with PBS-T (saline containing 0.05% Tween20) and then subjected to replacement with PBS-T being repeated three times every 5 minutes. Excess water around the sections was removed with Kimwipes, and then the sections were circled using a DAKOPEN (DAKO). As blocking solutions, an MOM mouse Ig blocking reagent (VECTASTAIN) and a PBS-T solution containing 10% FBS were overlaid on mouse tissue and dog tissue, respectively, and then left to stand in a moist chamber at room temperature for 1 hour. Next, a solution of the anti-CAPRIN-1 monoclonal antibody (monoclonal antibody #1 prepared in Example 4) of 10 μg/ml adjusted with a blocking solution, which reacts with cancer cell surfaces and comprises the heavy chain variable region of SEQ ID NO: 42 and the light chain variable region of SEQ ID NO: 46, was placed on and then left to stand overnight in a moist chamber at 4° C. 10 minutes of washing with PBS-T was performed 3 times, and then an MOM biotin-labeled anti-IgG antibody (VECTASTAIN) diluted 250-fold with the blocking solution was placed and then left to stand at room temperature for 1 hour in a moist chamber. After ten (10) minutes of washing with PBS-T was performed 3 times, an avidin-biotin ABC reagent (VECTASTAIN) was placed on, and then the sample was left to stand in a moist chamber at room temperature for 5 minutes. After ten (10) minutes of washing with PBS-T was performed 3 times, a DAB coloring solution (DAB 10 mg+30% $H_2O_2$ 10 μl/0.05 M Tris-HCl (pH 7.6) 50 ml) was placed on, and then the sample was left to stand in a moist chamber at room temperature for 30 minutes. After rinsing with distilled water, a hematoxylin reagent (DAKO) was placed on, the sample was left to stand at room temperature for 1 minute, and then rinsed with distilled water. The slide glass was immersed in 70%, 80%, 90%, 95%, and then 100% ethanol solutions in such order for 1 minute each and then left to stand overnight in xylene. The slide glass was removed, sealed in Glycergel Mounting Medium (DAKO), and then observed. As a result, the expression of CAPRIN-1 was slightly observed within cells of each tissue of salivary gland, kidney, colon, and stomach, but the expression of the same was not observed on cell surfaces. Furthermore, no expression was observed in tissues from other organs.

(5)-2 CAPRIN-1 Expression in Dog Breast Cancer Tissue

Frozen section slides were prepared by a method similar to the above using 108 frozen breast cancer tissue specimens of dogs pathologically diagnosed as having malignant breast cancer, and immunohistochemical staining was performed using the monoclonal antibody #1 prepared in Example 4. As a result, the expression of CAPRIN-1 was observed in 100 out of 108 specimens (92.5%) and CAPRIN-1 was strongly expressed on the surfaces of cancer cells with a particularly high grade of atypism.

(5)-3 CAPRIN-1 Expression in Human Breast Cancer Tissues

Immunohistochemical staining was performed using 188 breast cancer tissue specimens on a paraffin-embedded human breast cancer tissue array (BIOMAX). After 3 hours of treatment of the human breast cancer tissue array at 60° C., the array was placed in a staining bottle filled with xylene, followed by xylene replacement being repeated three times every 5 minutes. Next, a similar procedure was performed with ethanol and PBS-T instead of xylene. The human breast cancer tissue array was placed in a staining bottle filled with 10 mM citrate buffer (pH 6.0) containing 0.05% Tween20. After 5 minutes of treatment at 125° C., the array was left to stand at room temperature for 40 minutes or more. Excess water around the sections was removed with Kimwipes, the sections were circled with a DAKOPEN, and Peroxidase Block (DAKO) was added dropwise in appropriate amounts. After left to stand at room temperature for 5 minutes, the array was placed in a staining bottle filled with PBS-T, followed by PBS-T replacement being repeated three times every 5 minutes. As a blocking solution, a PBS-T solution containing 10% FBS was placed on the array, and then the array was left to stand in a moist chamber at room temperature for 1 hour. Next, a solution of the monoclonal antibody #1 of 10 μg/ml adjusted with a PBS-T solution containing 5% FBS, which reacts with cancer cell surfaces and had been prepared in Example 4, was placed on, and the array was left to stand overnight in a moist chamber at 4° C. After ten (10) minutes of washing with PBS-T was performed 3 times, Peroxidase Labeled Polymer Conjugated (DAKO) was added dropwise in appropriate amounts and then the array was left to stand in a moist chamber at room temperature for 30 minutes. After ten (10) minutes of washing with PBS-T was performed 3 times, a DAB coloring solution (DAKO) was placed on and then it was left to stand at room temperature for about 10 minutes. The coloring solution was discarded, 10 minutes of washing with PBS-T was performed 3 times, and then it was rinsed with distilled water. The array was immersed in 70%, 80%, 90%, 95%, and then 100% ethanol solutions in such order for 1 minute each, and then left to stand in xylene overnight. The slide glass was removed, sealed in Glycergel Mounting Medium (DAKO), and then observed. As a result, the strong expression of CAPRIN-1 was observed in 138 out of a total of 188 breast cancer tissue specimens (73%).

(5)-4 CAPRIN-1 Expression in Human Malignant Brain Tumor

Immunohistochemical staining was performed according to a method similar to that used in (5)-3 above with 247 malignant brain tumor tissue specimens on a paraffin-embedded human malignant brain tumor tissue array (BIOMAX), using the monoclonal antibody #1 prepared in Example 4. As a result, the strong expression of CAPRIN-1 was observed in 227 out of a total of 247 malignant brain tumor tissue specimens (92%).

(5)-5 CAPRIN-1 Expression in Human Breast Cancer Metastasized Lymph Node

Immunohistochemical staining was performed according to a method similar to that in (5)-3 above with 150 breast cancer metastasized lymph node tissue specimens on a paraffin-embedded human breast cancer metastasized lymph node tissue array (BIOMAX), using the monoclonal antibody #1 prepared in Example 4. As a result, the strong expression of CAPRIN-1 was observed in 136 out of a total of 150 breast cancer metastasized lymph node tissue specimens (90%). Specifically, it was revealed that CAPRIN-1 was strongly expressed also in cancer tissues that had metastasized from breast cancer.

(5)-6 CAPRIN-1 Expression in Various Human Cancer Tissues

Immunohistochemical staining was performed according to a method similar to the above with specimens on various paraffin-embedded human cancer tissue arrays (BIOMAX), using the monoclonal antibody #1 prepared in Example 4. As a result, the strong expression of CAPRIN-1 was observed in esophageal cancer, colon cancer, rectal cancer, lung cancer, renal cancer, bladder cancer, and uterine cervix cancer.

Example 2

Preparation of Novel Human Cancer Antigen Protein (1) Preparation of Recombinant Protein Based on the gene of SEQ ID NO: 1 obtained in Example 1, a recombinant protein from the human homologous gene was prepared by the following method. PCR was performed in a total volume of 50 μl with 1 μl of cDNA, two primers (SEQ ID NOS: 37 and 38 comprising Sac I and Xho I restriction enzyme cleavage sequences) of 0.4 μM each, 0.2 mM dNTP, and 1.25U PrimeSTAR HS polymerase (Takara Shuzo Co., Ltd.), prepared by adding the reagents and an accompanying buffer. The expression had been confirmed by an RT-PCR method for the cDNA used herein from among various tissue.or cell-derived cDNAs prepared in Example 1. PCR was preformed by repeating a cycle of 98° C. for 10 seconds and 68° C. for 2.5 minutes 30 times using a Thermal Cycler (BIO RAD). The above two primers are capable of amplifying a region encoding the entire amino acid sequence of SEQ ID NO: 2. After PCR, the thus amplified DNA was subjected to electrophoresis on 1% agarose gel, and then an about 2.1 kbp DNA fragment was purified using a QIAquick Gel Extraction Kit (QIAGEN).

The thus purified DNA fragment was ligated to a cloning vector PCR-Blunt (Invitrogen). After transformation of *Escherichia coli* with it, plasmid was collected. It was verified by sequencing that the thus amplified gene fragment has the sequence of interest. The plasmid having a matched sequence with the sequence of interest was treated with Sac I and Xho I restriction enzymes and then purified with a QIAquick Gel Extraction Kit. The gene sequence of interest was inserted into an *Escherichia coli* expression vector pET30a (Novagen) treated with Sac I and Xho I restriction enzymes. A His-tag fused recombinant protein can be produced using the vector. The plasmid was transformed into *Escherichia coli* for expression, BL21(DE3), and then expression was induced with 1 mM IPTG, so that the protein of interest was expressed in *Escherichia coli*.

(2) Purification of Recombinant Protein

The above-obtained recombinant *Escherichia coli* expressing the gene of SEQ ID NO: 1 was cultured in LB medium containing 30 μg/ml kanamycin at 37° C. until absorbance at 600 nm reached around 0.7, isopropyl-β-D-1-thiogalactopyranoside was added at a final concentration of 1 mM, and then cells were cultured at 37° C. for 4 hours. Subsequently, centrifugation was performed at 4800 rpm for 10 minutes and then cells were collected. The resulting cell pellet was suspended in phosphate buffered saline and centrifuged at 4800 rpm for 10 minutes, and then cells were washed.

The cells were suspended in phosphate buffered saline and then disrupted by ultrasonication on ice. The resulting lysate of the ultrasonicated *Escherichia coli* was subjected to centrifugation at 6000 rpm for 20 minutes, and then the resulting supernatant was regarded as a soluble fraction and the precipitate was regarded as an insoluble fraction.

The soluble fraction was added to a nickel chelate column adjusted according to a conventional method (carrier: Chelating Sepharose™ Fast Flow (GE HealthCare); column capacity of 5 ml; and equilibration buffer: 50 mM hydrochloride buffer (pH 8.0)). Unadsorbed fractions were washed off with 50 mM hydrochloride buffer (pH 8.0) in an amount 10 times the column capacity and 20 mM phosphate buffer (pH 8.0) containing 20 mM imidazole. Immediately after washing, 6 beds were eluted with 20 mM phosphate buffer (pH 8.0) containing 100 mM imidazole. The elution of the protein of interest was confirmed by Coomassie staining on the elution fraction with 20 mM phosphate buffer (pH 8.0) containing 100 mM imidazole, and then the elution fraction was added to a strong anion exchange column (carrier: Q Sepharose™ Fast Flow (GE HealthCare); column capacity of 5 ml; and 20 mM phosphate buffer (pH 8.0) as an equilibration buffer). An unadsorbed fraction was washed off with 20 mM phosphate buffer (pH 7.0) in an amount 10 times the column capacity and 20 mM phosphate buffer (pH 7.0) containing 200 mM sodium chloride. Immediately after washing, 5 beds were eluted with 20 mM phosphate buffer (pH 7.0) containing 400 mM sodium chloride, and thus the purified fraction of the protein having the amino acid sequence represented by SEQ ID NO: 2 was obtained.

200 μl of each purified sample obtained by the above method was dispensed into 1 ml of reaction buffer (20 mM Tris-Hcl, 50 mM, NaCl, 2 mM $CaCl_2$ pH 7.4), followed by addition of 2 μl of enterokinase (Novagen). After that, the resultant was left to stand overnight at room temperature for reaction so that His-tag was cleaved off, and then purification was performed using an Enterokinase Cleavage Capture Kit (Novagen) according to the accompanying protocols. Next, 1.2 ml of the purified sample obtained by the above method was subjected to the buffer replacement with physiological phosphate buffer (Nissui Pharmaceutical Co., Ltd.) using an ultrafiltration NANOSEP 10K OMEGA (PALL). Further, sterile filtration was performed using HT Tuffryn Acrodisc 0.22 μm (PALL) and then the resultant was used for the following experiment.

Example 3

Preparation of Chicken Monoclonal Antibody Against CAPRIN-1

300 μg of the antigen protein (human CAPRIN-1) 0 shown by SEQ ID NO: 2 prepared in Example 2 was mixed with an equivalent amount of Freund's complete adjuvant, and then this was used as an antigen solution for one chicken. The antigen solution was intraperitoneally administered to 7-week-old chickens, and then the administration was performed 7 times every 4 weeks, and thus immunization was completed. Each spleen was excised on day 4 after the final immunization, and sandwiched between two sterilized slide glasses and then crushed. The resultant was washed with PBS(−) (Nissui) and then centrifuged at 1500 rpm for 10 minutes to remove the supernatant. This procedure was repeated 3 times, so that splenocytes were obtained. The thus obtained splenocytes and chicken myeloma cells deficient in light chain were mixed at a ratio of 5:1. The used chicken myeloma cells had been established from a chicken by a transformation using an avian reticuloendotheliosis virus. A PEG solution prepared by mixing 200 μl of IMDM medium containing 10% FBS heated at 37° C. and 800 μl of PEG1500 (Boehringer) was added to the mixture, left to stand for 5 minutes for cell fusion, and then subjected to centrifugation at 1700 rpm for 5 minutes. After removal of the supernatant, cells were suspended in 300 ml of IMDM medium containing 10% FBS, supplemented with a HAT solution (Gibco) (2% equivalent) (HAT selective medium), and then the cell suspension was plated on thirty 96-well plates (Nunc) at 100 μl per well. Cells were cultured for 7 days at 37° C. under conditions of 5% $CO_2$, so that hybridoma prepared by fusion of splenocytes and chicken myeloma cells were obtained.

Hybridomas were selected using as a marker the binding affinity of the antibody produced by the prepared hybridomas to the CAPRIN-1 protein. The CAPRIN-1 protein solution (1 μg/ml) prepared in Example 2 was added to a 96-well plate at 100 μl per well and then left to stand at 4° C. for 18 hours. Each well was washed 3 times with PBS-T, 400 μl of a 0.5% Bovine Serum Albumin (BSA) solution (Sigma) was added per well, and then the plate was left to stand at room temperature for 3 hours. The solution was removed, and then the wells were washed three times with 400 μl of PBS-T per well. The culture supernatant of the above-obtained hybridomas was added at 100 μl per well, and then left to stand at room temperature for 2 hours. After washing each well three times with PBS-T, an HRP-labeled anti-chicken IgY antibody (SIGMA) diluted 5000-fold with PBS was added at 100 μl per well and the resultant was then left to stand at room temperature for 1 hour. After washing the wells three times with PBS-T, 100 μl of a TMB substrate solution (Thermo) was added per well and then left to stand for 15 to 30 minutes for coloring reaction. After color development, 100 μl of 1N sulfuric acid was added per well to stop the reaction, and then absorbances at 450 nm and 595 nm were measured using an absorption spectrometer. As a result, several hybridomas producing antibodies with high absorbance values were selected.

The thus selected hybridomas were added to a 96-well plate at 0.5 cells per well and then cultured. After 1 week, hybridomas that had formed single colonies in wells were observed. These cells in the wells were further cultured, and then hybridomas were selected using as a marker the binding affinity of antibodies produced by the cloned hybridomas to the CAPRIN-1 protein. The CAPRIN-1 protein solution (1 μg/ml) prepared in Example 2 was added to a 96-well plate at 100 μl per well, and then left to stand at 4° C. for 18 hours. Each well was washed with PBS-T three times, 400 μl of a 0.5% BSA solution was added per well, and then the resultant was left to stand at room temperature for 3 hours. The solution was removed, and then the wells were washed three times with 400 μl of PBS-T per well. 100 μl of each culture supernatant of the above-obtained hybridomas was added per well, and then the plate was left to stand at room temperature for 2 hours. After washing each well three times with PBS-T, 100 μl of an HRP-labeled anti-chicken IgY antibody (SIGMA) diluted 5000-fold with PBS was added per well and then left to stand at room temperature for 1 hour. After washing the wells three times with PBS-T, 100 μl of a TMB substrate solution (Thermo) was added per well, and then left to stand for 15 to 30 minutes for coloring reaction. After color development, 100 μl of 1N sulfuric acid was added per well to stop the reaction and then absorbances at 450 nm and 595 nm were measured using an absorption spectrometer. As a result, several hybridoma cell lines producing monoclonal antibodies reactive with the CAPRIN-1 protein were obtained.

Next, of those monoclonal antibodies, antibodies reactive with the cell surfaces of breast cancer cells expressing CAPRIN-1 were selected. Specifically, $5\times10^5$ cells of the human breast cancer cell line MDA-MB-231V were subjected to centrifugation in a 1.5-ml microcentrifuge tube, and 100 μl of the culture supernatant of each of the above hybridomas was added to the tube, and then the tube was left to stand on ice for 1 hour. After washing with PBS, an FITC-labeled goat anti-chicken IgG (H+L) antibody (SouthernBiotech) diluted 30-fold with PBS containing 0.1% FBS was added, and then the resultant was left to stand on ice for 1 hour. After washing with PBS, fluorescence intensity was measured using a FACS caliber (Becton, Dickinson and Company). Meanwhile, procedures similar to the above were performed for medium for culturing hybridomas, so that a control sample was obtained. As a result, one monoclonal antibody (monoclonal antibody #1) that had exhibited fluorescence intensity stronger than that of the control, and that is, that reacted with the cell surfaces of CAPRIN-1-expressing breast cancer cells, was selected.

Example 4

Characterization of Selected Antibody (1) Cloning of Genes of Anti-CAPRIN-1 Monoclonal Antibody Variable Regions mRNA was extracted from a chicken-derived hybridoma cell line producing monoclonal antibodies (selected in Example 3) reactive with the surfaces of CAPRIN-1-expressing breast cancer cells. An RT-PCR method using primers specific to the chicken FR1-derived sequence and the chicken FR4-derived sequence was performed therefor, and the gene of the heavy chain variable (VH) region and the gene of the light chain variable (VL) region of the antibody were obtained. mRNA was also extracted from two mouse-derived hybridoma cell lines producing monoclonal antibodies reactive with the surfaces of CAPRIN-1-expressing breast cancer cells. An RT-PCR method using primers specific to the mouse FR1-derived sequence and the mouse FR4-derived sequence was performed therefor, and the gene of the heavy chain variable (VH) region and the gene of the light chain variable (VL) region of each antibody were obtained. For sequence determination, these genes were cloned into a pCR2.1 vector (Invitrogen).

(1)-1 RT-PCR

After extraction of total RNA from $10^6$ cells of each hybridoma cell line using a High Pure RNA Isolation Kit (Roche), cDNA was synthesized using a PrimeScriptII 1st strand cDNA Synthesis Kit (Takara). These procedures were performed according to protocols attached to each kit.

The gene of the chicken antibody heavy chain variable region and the gene of the chicken antibody light chain variable region, and the gene of the mouse antibody heavy chain variable region and the gene of the mouse antibody light chain variable region were each amplified by a PCR method according to a conventional method using the thus synthesized cDNA as a template and KOD-Plus-DNA Polymerase (TOYOBO).

To obtain the gene of the chicken antibody VH region, a primer specific to the chicken heavy chain FR1 sequence and a primer specific to the chicken heavy chain FR4 sequence were used. Furthermore, to obtain the gene of the VL region, a primer specific to the chicken light chain FR1 sequence and a primer specific to the chicken light chain FR4 were used. The genes of mouse antibody VH and VL regions were obtained in a manner similar to the above. Specifically, a primer specific to the mouse heavy chain FR1 sequence, a primer specific to the mouse heavy chain FR4 sequence, a primer specific to the mouse light chain FR1 sequence, and a primer specific to the mouse light chain FR4 were used.

The thus obtained PCR products were each subjected to agarose gel electrophoresis, and DNA bands of the VH region and the VL region were excised. DNA fragments were purified using a QIAquick Gel purification kit (QIAGEN) according to the accompanying protocols. The purified DNA was cloned into a pCR2.1 vector using a TA cloning kit (Invitrogen). The ligated vector was transformed into DH5 competent cells (TOYOBO) according to a conventional method. 10 clones of each transformant were cultured overnight in medium (100 μg/ml ampicillin) at 37° C., and then plasmid DNA was purified using a Qiaspin Miniprep kit (QIAGEN).

(1)-2 Sequence Determination

The gene sequences of the VH region and the VL region in each plasmid obtained above were analyzed with an M13 forward primer (SEQ ID NO: 47) and an M13 reverse primer (SEQ ID NO: 48) on a fluorescence sequencer (DNA sequencer 3130XL; ABI), using a Big Dye Terminator Ver3.1 Cycle Sequencing Kit (ABI) according to the accompanying protocols. As a result, each gene sequence was determined. The sequences were identical among the 10 clones.

The thus obtained gene sequence encoding the heavy chain variable region of the chicken-derived monoclonal antibody is represented by SEQ ID NO: 49 and the amino acid sequence thereof is represented by SEQ ID NO: 42, and the thus obtained gene sequence encoding the light chain variable region is represented by SEQ ID NO: 50 and the amino acid sequence thereof is represented by SEQ ID NO: 46.

Specifically, it was revealed that the monoclonal antibody #1 comprises the heavy chain variable region of SEQ ID NO: 42 and the light chain variable region of SEQ ID NO: 46, wherein CDR1, CDR2, and CDR3 in the heavy chain variable region consist of the amino acid sequences of SEQ ID NOS: 39, 40, and 41, respectively, and the CDR1, CDR2, and CDR3 in the light chain variable region consist of the amino acid sequences of SEQ ID NOS: 43, 44, and 45, respectively.

(2) Preparation of Human-chicken Chimeric Recombinant Antibody and Mouse-Chicken Chimeric Antibody An amplification fragment of the gene of the heavy chain variable region (SEQ ID NO: 42) of the chicken monoclonal antibody #1 obtained in (1) above was treated at both ends with restriction enzymes and then purified. The resulting fragment was inserted into a pcDNA4/myc-His (Invitrogen) vector according to a conventional method, into which a chicken antibody-derived leader sequence comprising SEQ ID NO: 51 and a human IgG1 H-chain constant region comprising SEQ ID NO: 52 had already been inserted. Furthermore, an amplification fragment of the gene of the chicken monoclonal antibody #1 light chain variable region (SEQ ID NO: 46) was treated at both ends with restriction enzymes and then purified. The resulting fragment was inserted into a pcDNA3.1/myc-His (Invitrogen) vector according to a conventional method, into which a chicken antibody-derived leader sequence comprising SEQ ID NO: 51 and a human IgG1 L-chain constant region comprising SEQ ID NO: 53 had already been inserted.

Next, the above recombinant vector into which the heavy chain variable region (SEQ ID NO: 42) of the chicken monoclonal antibody #1 had been inserted, and the above recombinant vector into which the chicken monoclonal antibody #1 light chain variable region (SEQ ID NO: 46) had been inserted, were introduced into CHO-K1 cells (obtained from RIKEN Cell Bank). Specifically, $2\times10^5$ CHO-K1 cells cultured in 1 ml of Ham's F12 medium (Invitrogen) containing 10% FBS per well of a 12-well culture plate were washed with PBS(−). 1 ml of Ham's F12 medium containing 10% FBS was further added per well and then a mixture of 250 ng of each of the above vectors dissolved in 30 μl of OptiMEM (Invitrogen) and 30 μl of a Polyfect transfection reagent (QIAGEN) was added to each well. CHO-K1 cells into which the above recombinant vector had been introduced were cultured in Ham's F12 medium containing 10% FBS, supplemented with 200 μg/ml Zeocin (Invitrogen) and 200 μg/ml geneticin (Roche). CHO-K1 cells into which the above recombinant vector had been introduced were plated in a 96-well plate at 0.5 cells per well. Thus, a cell line stably producing a human-chicken chimeric antibody #1 (also referred to as #1) having the chicken monoclonal antibody #1 variable region was prepared. The thus prepared cell line was cultured in a 150 $cm^2$ flask containing 30 ml of serum-free OptiCHO medium (Invitrogen) at $5\times10^5$ cells/ml for 5 days. Then, a culture supernatant containing #1 was obtained.

With a method similar to the above, an amplification fragment of the gene of the heavy chain variable region (SEQ ID NO: 42) of the chicken monoclonal antibody #1 was treated at both ends with restriction enzymes and then purified. The resultant was inserted according to a conventional method into a pcDNA4/myc-His (Invitrogen) vector into which a chicken antibody-derived leader sequence and a mouse IgG1 H-chain constant region had already been inserted. Furthermore, an amplification fragment of the gene of the light chain variable region (SEQ ID NO: 46) of the chicken monoclonal antibody #1 was treated at both ends with restriction enzymes and then purified. The resultant was then inserted according to a conventional method into a pcDNA3.1/myc-His (Invitrogen) vector into which a chicken antibody-derived leader sequence and the mouse IgG1 L-chain constant region had already been inserted. The resultant was introduced into CHO-K1 cells in a manner similar to the above and thus a cell line stably producing a mouse-chicken chimeric antibody #1 comprising the chicken monoclonal antibody #1 variable region was prepared. The cells were cultured at $5\times10^5$ cells/ml using a 150 $cm^2$ flask and 30 ml of serum free OptiCHO medium (Invitrogen) for 5 days, so that a culture supernatant containing the mouse-chicken chimeric antibody #1 was obtained.

(3) CAPRIN-1 Expression on Various Cancer Cell Surfaces Using Anti-CAPRIN-1 Antibody #1

Next, 7 breast cancer cell lines (MDA-MB-157, T47D, MRK-nu-1, MDA-MB-231V, BT20, SK-BR-3, and DA-MB-231T) for which CAPRIN-1 gene expression had been observed, and the other 3 breast cancer cell lines (MDA-MB-231C, MCF-7, and ZR75-1), 5 glioma cell lines (T98G SNB19, U251, U87MG, and U373), 4 renal cancer cell lines (Caki-1, Caki-2, A498, and ACHN), 2 gastric cancer cell lines (MNK28 and MNK45), 5 colorectal cancer cell lines (HT29, LoVo, Caco2, SW480, and HCT116), 3 lung cancer cell lines (A549, QG56, and PC8), 4 leukemia cell lines (AML5, Namalwa, BDCM, RPI1788), one lymphoma cell line (Ramos), one uterine cervix cancer cell line (SW756), one bladder cancer cell line (T24), and one esophageal cancer cell line (KYSE180) were examined for CAPRIN-1 protein expression on the cell surfaces of each cell line using the culture supernatants of CHO-K1 cells containing #1 obtained in (2) above. $10^6$ cells of each cell line were centrifuged in a 1.5 ml microcentrifuge tube. Each cell culture supernatant (100 μl) of CHO-K1 cells containing #1 obtained in (2) above was added and then left to stand on ice for 1 hour. After washing with PBS, a FITC-labeled goat-anti human IgG (H+L) antibody (SouthernBiotech) and a FITC-labeled anti-mouse IgG (H+L) antibody (Invitrogen) diluted 500-fold with PBS containing 0.1% FBS were added and then left to stand on ice for 1 hour. After washing with PBS, fluorescence intensity was measured using a FACS Calibur (Becton, Dickinson and Company). Meanwhile, procedures similar to the above were performed using a culture supernatant of CHO-K1 cells into which no antibody gene had been introduced and medium for culturing hybridomas, so that a negative control sample was prepared. As a result, cells to which the antibody #1 had been added exhibited fluorescence intensity stronger by 20% or more than that of the control. Specifically, fluorescence intensity was enhanced to 4900% in the case of SK-BR-3 and 5000% in the case of MDA-MB-231V. It was revealed by these results that the CAPRIN-1 protein was expressed on the cell membrane surfaces of the above human cancer cell lines. The percentage of enhancement in the above fluorescence intensity was expressed as percentage of increase in mean fluorescence intensity (MFI level) in each type of cell and calculated by the following formula.

Percentage of increase in mean fluorescence intensity (percentage of enhancement in fluorescence intensity)(%)=((MFI level in cells having reacted with anti-human CAPRIN-1 antibody)−(MFI level of the control))/(MFI level of control)×100.

Figure 2:
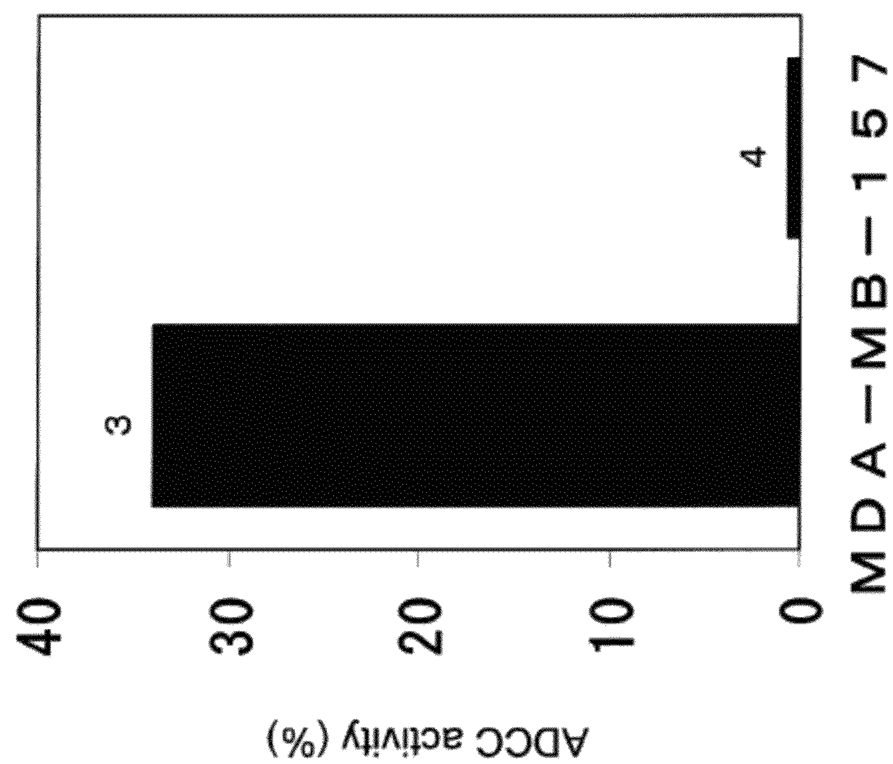
FIG. 2 shows the cytotoxicity of an anti-CAPRIN-1 monoclonal antibody #1 (that is reactive with the surfaces of the cancer cells) against the MDA-MB-157 breast cancer cell line expressing CAPRIN-1. Reference No. 3 indicates the activity exhibited when the anti-CAPRIN-1 monoclonal antibody #1 was added. Reference No. 4 indicates the activity exhibited when PBS was added instead of the antibodies.

(4) Anti-tumor Effects (ADCC Activity) of Anti-CAPRIN-1 Antibody #1 Against Cancer Cells Next, the anti-CAPRIN-1 antibody #1 was evaluated for the cytotoxic activity (ADCC activity) against cancer cells. Each cell culture supernatant producing #1 obtained in (2) above was purified using Hitrap ProteinA Sepharose FF (GE HealthCare), subjected to buffer replacement with PBS(−), and then filtered with a 0.22 μm filter (Millipore). The resultants were used as antibodies for activity measurement. $10^6$ cells of MDA-MB-157 human breast cancer cell line were collected in a 50-ml centrifuge tube, 100 μCi chromium-51 was added, and then incubation was performed at 37° C. for 2 hours. Subsequently, the resultant was washed three times with RPMI1640 medium containing 10% FBS. Cells were added to a 96-well V-bottom plate at $5\times10^3$ cells per well for use as target cells. The above purified antibodies were added to the cells at a final concentration of 1 μg/ml. $2.5\times10^5$ cells of lymphocytes separated from human peripheral blood according to a conventional method were further added and then cultured for 4 hours at 37° C. under conditions of 5% $CO_2$. After culture, the amount of chromium-51 released from damaged cancer cells in a culture supernatant was measured, and the ADCC activity of each anti-CAPRIN-1 antibody against cancer cells was calculated. As negative control samples, a sample prepared by adding PBS instead of the anti-CAPRIN-1 antibodies and a sample prepared by adding an isotype control antibody instead of anti-CAPRIN-1 antibodies were used. As a result, the antibody #1 exhibited 30% or more cytotoxic activity against MDA-MB-157 (see FIG. 2). In contrast, the activity in the sample prepared by adding PBS as a negative control and the activity in the sample prepared by adding the isotype control antibody as a negative control were 1.1% and 2.0%, respectively. Similarly, the antibody #1 was examined for the ADCC activity against other cancer cells including glioma cell lines T98G and U373, lung cancer cell lines A549 and QG56, renal cancer cell lines Caki-1 and ACHN, a uterine cervix cancer cell line SW756, a bladder cancer cell line T24, an esophageal cancer cell line KYSE180, gastric cancer cell lines MNK28 and MNK45, a colorectal cancer cell line SW480, a leukemia cell line AML5, and a lymphoma cell line Ramos. As a result, the anti-CAPRIN-1 antibody #1 exhibited 16.4% activity against T98G (1.2% in the case of the isotype control), 23.1% against U373 (3.2% in the case of the isotype control), 36.1% against A549 (3.0% in the case of the isotype control), 33.5% against QG56 (0.5% in the case of the isotype control), 28.3% against Caki-1 (2.6% in the case of the isotype control), 25.1% against ACHN (1.6% in the case of the isotype control), 27.9% against SW756 (2.2% in the case of the isotype control), 25.8% against T24 (2.0% in the case of the negative control), 26.7% against KYSE180 (3.0% in the case of the isotype control), 21.5% against MNK28 (1.9% in the case of the isotype control), 23.0% against MNK45 (3.0% in the case of the isotype control), 24.0% against SW480 (1.8% in the case of the isotype control), 8.3% against AML5 (1.8% in the case of the isotype control), and 8.0% against Ramos (2.2% in the case of the isotype control). It was demonstrated by the above results that the thus obtained anti-CAPRIN-1 antibody #1 damages various human cancer cells expressing CAPRIN-1.

(5) Anti-tumor Effects (CDC Activity) of Anti-CAPRIN-1 Antibody #1 Against Cancer Cell Next, anti-CAPRIN-1 antibody #1 was evaluated for its cytotoxic activity (CDC activity) against cancer cells. Blood collected from a rabbit was added to an Eppendorf tube, left to stand at room temperature for 60 minutes, and then subjected to 5 minutes of centrifugation at 3000 rpm. Thus, serum for measurement of CDC activity was prepared. $10^6$ cells of human breast cancer cells MDA-MB-231V were collected in a 50-ml centrifuge tube, 100 μCi chromium-51 was added, and then incubation was performed at 37° C. for 2 hours. The resultant was washed three times with RPMI medium containing 10% FBS. Subsequently, the cells were suspended in RPMI medium containing the above-prepared rabbit serum (50%), and then added to a 96-well V-bottom plate at $5\times10^3$ cells per well. The antibody #1 obtained in (5) above was added to the cells at a final concentration of 1 μg/ml and then cells were cultured for 4 hours at 37° C. under conditions of 5% $CO_2$. After culture, the amount of chromium-51 released from damaged tumor cells in a culture supernatant was measured, and then the CDC activity against MDA-MB-231V was calculated. As a result, the antibody #1 exhibited 25% or more CDC activity. Therefore, it was revealed that #1 can damage cancer cells expressing CAPRIN-1 also by CDC activity.

Example 5

In vivo Anti-tumor Effects of Anti-CAPRIN-1 Antibody #1 in Mice

Next, the thus obtained anti-CAPRIN-1 antibody #1 was evaluated for its in vivo anti-tumor effects in tumor-bearing mice. Antibodies used herein were prepared by column purification of the culture supernatant of each cell producing #1 in the same manner as described above.

Figure 3:
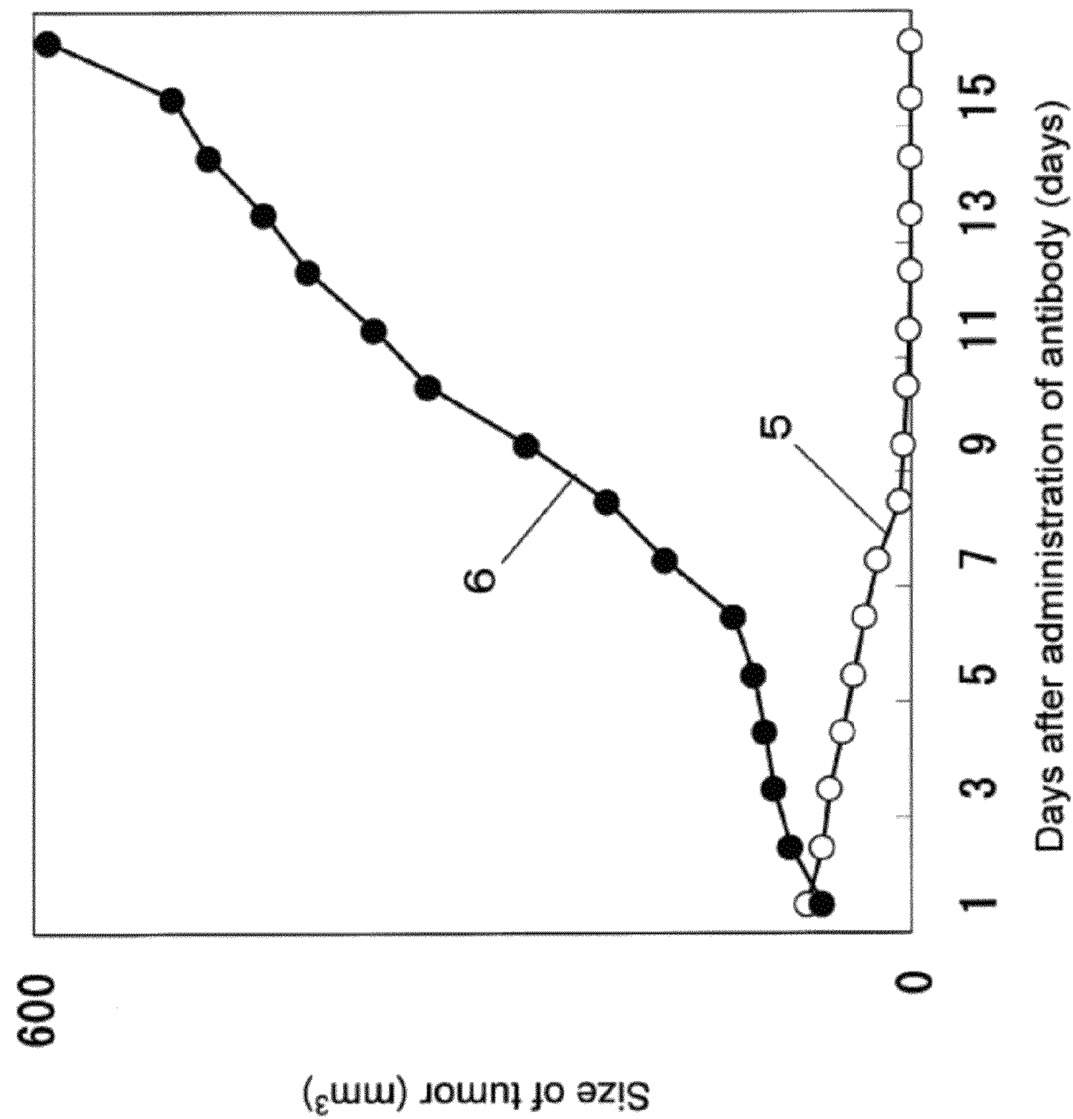
FIG. 3 shows the anti-tumor effects of the anti-CAPRIN-1 monoclonal antibody #1 (that is reactive with the surfaces of cancer cells) against Balb/c mice into which the 4T1 mouse breast cancer cell line expressing CAPRIN-1 was transplanted. Reference No. 5 indicates the tumor size of a mouse to which the anti-CAPRIN-1 monoclonal antibody #1 was administered. Reference No. 6 indicates the tumor size of a mouse to which PBS was administered instead of the antibodies.

The anti-tumor effects of the antibody #1 was examined using tumor-bearing mice into which a mouse-derived cancer cell line expressing CAPRIN-1 had been transplanted. 4T1 cells (purchased from ATCC) were transplanted subcutaneously to the dorsal region of 20 Balb/c mice (Japan SLC Inc.) at $5\times10^5$ cells/mouse. Cancers were allowed to grow to reach a size of about 5 mm in diameter. The antibody #1 was administered intraperitoneally to 10 tumor-bearing mice from among the 20 mice in an amount of 200 μg (in 200 μl) for one mouse. Subsequently, the same amount of the antibody was administered intraperitoneally to each tumor-bearing mouse 3 times in total within 2 days. Cancer sizes were measured every day and anti-tumor effects were examined by observation. Meanwhile, as a control group, PBS (−) was administered instead of the antibodies to the remaining 10 tumor-bearing mice. As a result of the observation of the anti-tumor effects, in the test group to which the anti-CAPRIN-1 antibody #1 had been administered, cancers were found to have regressed to about 55% on day 4, about 32% on day 6, about 7% on day 8, and cancers were found to have almost completely regressed before days 10 to 14, when the tumor volume at the initiation of the antibody administration was designated 100% (see FIG. 3). In the control group to which PBS(−) had been administered, the tumor size was increased to about 170%, 270%, 440%, and 670% on days 4, 6, 8, and 11, respectively (see FIG. 3). It was demonstrated by the results that the obtained antibody #1 exhibits strong anti-tumor effects in vivo against cancer cells expressing CAPRIN-1. The tumor (cancer) size was calculated as a volume using the formula: length of major axis×length of minor axis×length of minor axis×0.5.

Industrial Applicability

The antibodies of the present invention are useful for treating and/or preventing a cancer.

All publications, patents, and patent applications cited herein are incorporated herein by reference in their entirety.

Sequence Listing Free Text

SEQ ID NOS: 31-38, 47, and 48: primers

The invention claimed is:

1. A pharmaceutical composition for the treatment of a CAPRIN-1-expressing cancer or preventing the recurrence of a CAPRIN-1-expressing cancer, comprising an antibody or a fragment thereof as an active ingredient that has immunological reactivity with a CAPRIN-1 protein, wherein the antibody comprises a heavy chain variable region comprising SEQ ID NOS: 39, 40, and 41 and a light chain variable region comprising SEQ ID NOS: 43, 44, and 45 or a fragment thereof having anti-tumor activity.

2. The pharmaceutical composition according to claim 1, wherein the cancer is breast cancer, brain tumor, leukemia, lymphoma, lung cancer, mastocytoma, renal cancer, uterine cervix cancer, esophageal cancer, gastric cancer, bladder cancer, or colorectal cancer.

3. The pharmaceutical composition according to claim 1, wherein the antibody is a human antibody, humanized antibody, chimeric antibody, single chain antibody, or bispecific antibody.

4. An antibody, which comprises a heavy chain variable region comprising SEQ ID NOS: 39, 40, and 41 and a light chain variable region comprising SEQ ID NOS: 43, 44, and 45, and has immunological reactivity with a CAPRIN-1 protein.

5. The antibody according to claim 4, which is a human antibody, humanized antibody, chimeric antibody, single chain antibody, or bispecific antibody.

6. A pharmaceutical combination for treating cancer, comprising the pharmaceutical composition of claim 1 and a pharmaceutical composition containing an antitumor agent.

7. A method for the treatment of a CAPRIN-1-expressing cancer or preventing the recurrence of a CAPRIN-1-expressing cancer in a subject, comprising administering to the subject a therapeutically effective amount of the pharmaceutical composition of claim 1.

8. A method for the treatment of a CAPRIN-1-expressing cancer or preventing the recurrence of a CARRIN-1-expressing cancer in a subject with cancer, comprising administering a therapeutically effective amount of the pharmaceutical composition comprising the pharmaceutical combination of claim 6 to a subject in need thereof.

9. The method of claim 7, wherein the cancer is breast cancer, brain tumor, leukemia, lymphoma, lung cancer, mastocytoma, renal cancer, uterine cervix cancer, esophageal cancer, gastric cancer, bladder cancer, or colorectal cancer.

10. The method of claim 8, wherein the cancer is breast cancer, brain tumor, leukemia, lymphoma, lung cancer, mastocytoma, renal cancer, uterine cervix cancer, esophageal cancer, gastric cancer, bladder cancer, or colorectal cancer.

11. The method of claim 7, wherein the cancer is breast cancer.

12. The method of claim 8, wherein the cancer is breast cancer.

13. The method for treating a rancor in a subject with cancer according to claim 7, wherein the pharmaceutical composition is administered intraperitoneally.

14. The method for treating a cancer in a subject with cancer according to claim. 8, wherein the pharmaceutical compositions comprising, the pharmaceutical combination is administered intraperitoneally.

* * * * *